(12) United States Patent
Taghavi et al.

(10) Patent No.: US 10,375,964 B2
(45) Date of Patent: *Aug. 13, 2019

(54) MICROBIAL COMPOSITIONS AND METHODS OF USE FOR BENEFITING PLANT GROWTH AND TREATING PLANT DISEASE

(71) Applicant: FMC Corporation, Philadelphia, PA (US)

(72) Inventors: Safiyh Taghavi, Chapel Hill, NC (US); Daniel van der Lelie, Chapel Hill, NC (US); Roderick McLeod, Lethbridge (CA); Kevin R. Brost, Calgary (CA); John E. Kibbee, Guelph (CA)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/539,991

(22) PCT Filed: Dec. 28, 2015

(86) PCT No.: PCT/US2015/067668
§ 371 (c)(1),
(2) Date: Jun. 26, 2017

(87) PCT Pub. No.: WO2016/109424
PCT Pub. Date: Jul. 7, 2016

(65) Prior Publication Data
US 2017/0367347 A1    Dec. 28, 2017

Related U.S. Application Data

(60) Provisional application No. 62/097,287, filed on Dec. 29, 2014.

(51) Int. Cl.
| | |
|---|---|
| *A01N 63/00* | (2006.01) |
| *A01N 53/00* | (2006.01) |
| *C05F 11/08* | (2006.01) |
| *C05G 3/00* | (2006.01) |
| *C12R 1/07* | (2006.01) |
| *C12R 1/125* | (2006.01) |

(52) U.S. Cl.
CPC ............ *A01N 63/00* (2013.01); *A01N 53/00* (2013.01); *C05F 11/08* (2013.01); *C05G 3/0064* (2013.01); *C12R 1/07* (2013.01); *C12R 1/125* (2013.01); *Y02A 40/143* (2018.01); *Y02E 50/343* (2013.01); *Y02W 30/47* (2015.05)

(58) Field of Classification Search
None
See application file for complete search history.

(56) References Cited

U.S. PATENT DOCUMENTS

| | | |
|---|---|---|
| 3,004,774 A | 10/1961 | Marrone et al. |
| 4,931,398 A | 6/1990 | Kimura |
| 5,061,495 A | 10/1991 | Rossall |
| 5,215,747 A | 6/1993 | Hairston et al. |
| 5,344,647 A | 9/1994 | Rossall |
| 5,597,565 A | 1/1997 | Leifert et al. |
| 5,650,372 A | 7/1997 | Branly et al. |
| 5,667,779 A | 9/1997 | Kubo |
| 5,733,544 A | 3/1998 | Marrone et al. |
| 5,753,222 A | 5/1998 | Marrone et al. |
| 5,994,117 A | 11/1999 | Bacon et al. |
| 6,015,553 A | 1/2000 | Germida et al. |
| 6,060,051 A | 5/2000 | Heins et al. |
| 6,183,736 B1 | 2/2001 | Moyne et al. |
| 6,232,270 B1 | 5/2001 | Branly et al. |
| 6,291,426 B1 | 9/2001 | Heins et al. |
| 6,417,163 B1 | 7/2002 | Heins et al. |
| 6,524,998 B1* | 2/2003 | Kloepper .............. A01N 63/00 504/100 |
| 6,589,524 B1* | 7/2003 | Douillet ................ A01N 63/00 424/405 |

(Continued)

FOREIGN PATENT DOCUMENTS

| | | |
|---|---|---|
| EP | 0705807 B1 | 9/1999 |
| WO | 0049875 A1 | 8/2000 |

(Continued)

OTHER PUBLICATIONS

Borriss, R. In: "Bacteria in Agrobiology: Plant Growth Regulators", 2011, pp. 41-75.*

(Continued)

*Primary Examiner* — Vera Afremova
(74) *Attorney, Agent, or Firm* — Fox Rothschild LLP

(57) ABSTRACT

Compositions and methods are provided for a combination of a new strain of *Bacillus amyloliquefaciens* RTI301 and a new strain of *Bacillus subtilis* RTI477, the combination having growth promoting activity and activity against plant pathogens. The compositions containing the RTI301 and RTI477 strains are useful for benefiting plant growth and/or conferring protection against a pathogenic infection when applied to plant roots, seeds, callus tissue, grafts, and cuttings. Synergistic results are observed for the combination of the strains, and the combination of strains is useful to increase yield in crops including soybean and corn. The compositions containing the combination of strains can be applied alone or in combination with other microbial, biological, or chemical insecticides, fungicides, nematicides, bacteriocides, herbicides, plant extracts, plant growth regulators, and fertilizers.

28 Claims, 6 Drawing Sheets

Specification includes a Sequence Listing.

(56) References Cited

U.S. PATENT DOCUMENTS

| | | |
|---|---|---|
| 6,635,245 B1 | 10/2003 | Lehman et al. |
| 6,638,910 B2 | 10/2003 | Heins et al. |
| 6,808,917 B1 | 10/2004 | Johnson |
| 6,812,022 B1 | 11/2004 | Aonuma |
| 6,896,883 B2 | 5/2005 | Bergstrom et al. |
| 6,960,342 B2 | 11/2005 | Wu et al. |
| 7,097,830 B2 | 8/2006 | Nautiyal et al. |
| 7,615,366 B2 | 11/2009 | Kim et al. |
| 8,202,514 B2 | 6/2012 | Cho et al. |
| 8,518,428 B2 | 8/2013 | Shen et al. |
| 8,524,223 B2 | 9/2013 | Takayanagi et al. |
| 8,586,027 B2 | 11/2013 | Escobar Valdes et al. |
| 8,623,813 B2 | 1/2014 | Guilhabert-Goya et al. |
| 8,658,565 B2 | 2/2014 | Seitz et al. |
| 9,040,554 B2 * | 5/2015 | Hoffmann ............ C07D 471/04 514/300 |
| 9,232,800 B2 * | 1/2016 | Slomczynska ......... A01N 43/82 |
| 9,622,484 B2 | 4/2017 | Taghavi et al. |
| 2001/0004460 A1 | 6/2001 | Klittich et al. |
| 2003/0228679 A1 | 12/2003 | Smith et al. |
| 2004/0241098 A1 | 12/2004 | Labourdette et al. |
| 2005/0260293 A1 | 11/2005 | Bergstrom et al. |
| 2005/0266521 A1 | 12/2005 | Yoneda et al. |
| 2008/0070785 A1 | 3/2008 | Walter et al. |
| 2008/0076664 A1 | 3/2008 | Walter et al. |
| 2008/0160101 A1 | 7/2008 | Pujos et al. |
| 2008/0267937 A1 | 10/2008 | Yum et al. |
| 2008/0318777 A1 | 12/2008 | Lin et al. |
| 2009/0123445 A1 | 5/2009 | Saeki et al. |
| 2009/0175837 A1 | 7/2009 | Yuki et al. |
| 2009/0214503 A1 | 8/2009 | Ciampi Panno et al. |
| 2009/0308121 A1 | 12/2009 | Reddy et al. |
| 2010/0143316 A1 | 6/2010 | Hsieh et al. |
| 2010/0247706 A1 | 9/2010 | Knap et al. |
| 2010/0300166 A1 | 12/2010 | Mena Campos et al. |
| 2011/0033436 A1 | 2/2011 | Chen et al. |
| 2011/0110906 A1 | 5/2011 | Andersch et al. |
| 2011/0200571 A1 | 8/2011 | Bell et al. |
| 2011/0230345 A1 | 9/2011 | Snyder et al. |
| 2011/0257009 A1 | 10/2011 | Seitz et al. |
| 2012/0003199 A1 | 1/2012 | Scherer et al. |
| 2012/0070421 A1 | 3/2012 | Dietz et al. |
| 2012/0094834 A1 | 4/2012 | Frank et al. |
| 2012/0149571 A1 | 6/2012 | Kloepper et al. |
| 2012/0302442 A1 | 11/2012 | Grobler |
| 2012/0324604 A1 | 12/2012 | Dutton et al. |
| 2013/0017949 A1 | 1/2013 | Jabs et al. |
| 2013/0023412 A1 | 1/2013 | Gewehr et al. |
| 2013/0031673 A1 | 1/2013 | Grandlic et al. |
| 2013/0035229 A1 | 2/2013 | Muller et al. |
| 2013/0072384 A1 | 3/2013 | Pohlman et al. |
| 2013/0130898 A1 | 5/2013 | Gewehr et al. |
| 2013/0189227 A1 | 7/2013 | Royalty et al. |
| 2013/0236522 A1 | 9/2013 | Misumi |
| 2013/0252810 A1 | 9/2013 | Johnson |
| 2013/0261069 A1 | 10/2013 | Dutton et al. |
| 2013/0267415 A1 | 10/2013 | Renold et al. |
| 2013/0267418 A1 | 10/2013 | Kloepper et al. |
| 2013/0296271 A1 | 11/2013 | Sakai et al. |
| 2013/0331311 A1 | 12/2013 | Guilhabert-Goya et al. |
| 2013/0340123 A1 | 12/2013 | Pedersen et al. |
| 2014/0005047 A1 | 1/2014 | Hungenberg et al. |
| 2014/0056866 A1 | 2/2014 | Andersch et al. |
| 2014/0080709 A1 | 3/2014 | Bais et al. |
| 2014/0086875 A1 | 3/2014 | De Pontes et al. |
| 2014/0112899 A1 | 4/2014 | Jeschke et al. |
| 2014/0128256 A1 | 5/2014 | Asolkar et al. |
| 2014/0179528 A1 | 6/2014 | Amaki et al. |
| 2014/0228212 A1 | 8/2014 | Pedersen et al. |
| 2014/0274691 A1 | 9/2014 | Thompson et al. |
| 2014/0283443 A1 | 9/2014 | Werner et al. |
| 2014/0309107 A1 | 10/2014 | Wachendorff-Neumann et al. |
| 2014/0314718 A1 | 10/2014 | Hinarejos Esteve et al. |
| 2014/0315715 A1 | 10/2014 | Bais et al. |
| 2014/0364309 A1 | 12/2014 | Hellwege et al. |
| 2015/0141244 A1 | 5/2015 | Hellwege et al. |
| 2015/0148228 A1 | 5/2015 | Wachendorff-Neumann et al. |
| 2015/0250173 A1 | 9/2015 | Korber et al. |
| 2015/0264928 A1 | 9/2015 | Cristau et al. |
| 2015/0282488 A1 | 10/2015 | Riggs et al. |
| 2015/0289516 A1 | 10/2015 | Margolis et al. |
| 2015/0296799 A1 | 10/2015 | Margolis et al. |
| 2015/0342199 A1 | 12/2015 | Carrion Villanovo et al. |
| 2016/0186273 A1 | 6/2016 | Taghavi et al. |

FOREIGN PATENT DOCUMENTS

| | | |
|---|---|---|
| WO | 02072795 A2 | 9/2002 |
| WO | 2007/010459 | 1/2007 |
| WO | 2012064096 A2 | 5/2012 |
| WO | 2012076563 A1 | 6/2012 |
| WO | 2012130221 A2 | 10/2012 |
| WO | 2012143676 A2 | 10/2012 |
| WO | 2013029112 A1 | 3/2013 |
| WO | 2013034940 A2 | 3/2013 |
| WO | 2013100405 A1 | 7/2013 |
| WO | 2013152353 A1 | 10/2013 |
| WO | 2013165607 A1 | 11/2013 |
| WO | 2014076663 A1 | 5/2014 |
| WO | 2014079813 A1 | 5/2014 |
| WO | 2014086848 A1 | 6/2014 |
| WO | 2014086853 A1 | 6/2014 |
| WO | 2014086854 A1 | 6/2014 |
| WO | 2014086856 A1 | 6/2014 |
| WO | 2014118401 A1 | 8/2014 |
| WO | 2014129680 A1 | 8/2014 |
| WO | 2014147528 A1 | 9/2014 |
| WO | 2014147534 A1 | 9/2014 |
| WO | 2015023662 A1 | 2/2015 |

OTHER PUBLICATIONS

Magdalena Kröber et al: Non-target effects of bacterial biological control agents suppressing root pathogenic fungi, Frontiers in Microbiology, vol. 47, May 27, 2014, p. 129.

Mishra, Vijendra Kumar and Kumar, Ashok, Plant Growth Promoting and Phytostimulatory Potential of Bacillus Subtilis and Bacillus Amyloliquefaciens, ARPN Journal of Agricultural and Biological Science, vol. 7, No. 7, Jul. 2012, pp. 509-519.

Koumoutsi, Alexandra et al., Structural and Functional Characterization of Gene Clusters Directing Nonribosomal Synthesis of Bioactive Cyclic Lipopeptides in Bacillus amyloliquefaciens Strain FZB42, Jorunal of Bacteriology, Feb. 2004, 1084-1096.

Kröber, Magdalena et al, Effect of the strain Bacillus amyloliquefaciens FZB42 on the microbial community in the rhizosphere of lettuce under field conditions analyzed by whole metagenome sequencing, Frontiers in Microbiology, May 2014, vol. 5, Article 252, (16 pages).

Arguelles-Arias, Anthony et al., Bacillus amyloliquefaciens GA1 as a source of potent antibiotics and other secondary metabolites for biocontrol of plant pathogens, Microbiol Cell Factories 2009, 8:63 (12 pages).

Correa, Olga S. et al., Bacillus amyloliquefaciens BNM122, a potential microbial biocontrol agent applied on soybean seeds, causes a minor impact on rhizosphere and soil microbial communities, Applied Soil Ecology 41 (2009), 185-194.

Chen, X.H. et al., Genome analysis of Bacillus amyloliquefaciens FZB42 reveals its potential for biocontrol of plant pathogens, Journal of Biotechnology, 140 (2009), 27-37.

Priest, F.G. et al., Bacillus amyloliquefaciens sp. nov., nom. rev., International Journal of Systematic Bacteriology, Jan. 1987, pp. 69-71.

International Search Report and Written Opinion dated Mar. 29, 2016 in International Patent Application No. PCT/US2015/067608 (15 pages).

Stein, Torsten et al., Two Different Lantibiotic-Like Peptides Originate fromt he Ericin Gene Cluster of Bacillus subtilis A1/3, Journal of Bacteriology, vol. 184, No. 6, Mar. 2002, pp. 1703-1711.

(56) References Cited

OTHER PUBLICATIONS

Mariappan E. et al., Molecular mechanisms controlling cacilysin biosynthesis in plant growth promoting rhizobacterium—Bacillus amyloliquefacients FZB42, Dissertation from University of Berlin, 2012.
Alam, S. et al., Effect of Yeast Extract on alpha-Amylase Synthesis by Bacillus amyloliquefaciens, Biotechnology and Bioengineering, vol. 33, 1989, pp. 780-785.
Zhen Song, Isolation and characterization of a potential biocontrol Brevibacillus laterosporus, African Journal of Microbiology Research, Sep. 16, 2011, pp. 7 , vol. 5(18), pp. 2675-2681, Nigeria.
Ratul Saikia, Brevibacillus laterosporus strain BPM3, a potential biocontrol agent isolated from a natural hot water spring of Assam, India, Microbiological Research, Mar. 2011, pp. 11, 166(3):216-25, Biotechnology Division, North-EastInstitute of Science & Technology. (CSIR), Jorhat 785006, Assam, India.
Anita Khanafari, An investigation of rhizobacteria as biofertilizer on Mentha L. compounds change, Annals of Biological Research 2012, 3 (9):4293-4302, pp. 10, Scholars Research Library, Iran.
Bin Li, Inhibitory activity of Paenibacillus macerans and Paenibacillus polymyxa against Ralstonia solanacearum, African Journal of Microbiology Research, Oct. 2010, pp. 7, vol. 4(19), pp. 2048-2054, Academic Journals, Nigeria.
Rachel L. Melnick, Isolation of endophytic endospore-forming bacteria from Theobroma cacao as potential biological control agents of cacao diseases, Biological Control, 2011, pp. 10, 57 (2011) 236-245, Published by Elsevier Inc., Pennsylvania, United States.
Ling Ling Yang, Lysinibacillus mangiferahumi sp. nov., a new bacterium producing nematicidal volatile, Journal Antonie van Leeuwenhoek. vol. 102 No. 1 pp. 53-59, Feb. 2012, pp. 8, Springer, Netherlands.
Xiaomin Hu, Complete Genome Sequence of the Mosquitocidal Bacterium Bacillus sphaericus C3-41 and Comparison with Those of Closely Related Bacillus Species, Journal of Bacteriology, Apr. 2008, p. 2802-2902, vol. 190, No. 8, pp. 11, Washington.
Sonam Sharma, Isolation of Phosphate Solubilizing Microorganism (PSMs) From Soil, Journal of Microbiology and Biotechnology Research, J. Microbial. Biotech. Res., 2011, 1 (2): 90-95, pp. 6, Scholars Research Library, Iran.
N Murthy, Simplified Method of Preparing Colloidal Chitin Used for Screening of Chitinase—Producing Mircoorganisms, The Internet Journal of Microbiology, 2012 vol. 10, No. 2, pp. 5, United States.
Pamela A. Sokol, A More Sensitive Plate Assay for Detection at Protease Production by Pseudomonas aeruginosa, Journal of Clinical Microbiology, Apr. 1979, p. 536-540, vol. 9, No. 4, pp. 3, American Society for Microbiology, Washington DC.
Daniel Kaiser, Assessing fields for "pop up" starter fertilizer damage, Minnesota Crop News, Apr. 5, 2012, pp. 4, University of Minnesota, Minnesota, United States.
Peter Thomison, Be on the lookout for 'rootless corn', Progressive Forage Grower, Jun. 18, 2012, pp. 2, America.
O. Voges, Contribution to nutritional physiology and the differential diagnosis of bacterial hemorrhagic septicemia of Journal of Hygiene and Infectious Diseases, Dec. 1898, vol. 28, Issue 1, pp. 20-32.
Safiyah Taghavi, Genome Survey and Characterization of Endophytic Bacteria Exhibiting a Beneficial Effect on Growth and Development of Poplar Trees, Applied and Environmental Microbiology, Feb. 2009, p. 748-757, vol. 75, No. 3, pp. 10, AmericanSociety for Microbiology, America.
Pecci Y, Rivardo F, Martinotti MG, & Allegrone G.J, 2010. "LC/ESI-MS/MS characterization of lipopeptide biosurfactants produced by the Bacillus licheniformis V9T14 strain." Mass Spectrom. 45(7):772-778.
T. J. P. Smyth, A. Perfumo, S. McClean, R. Marchant, & I. M. Banat, 2010 "Isolation and Analysis of Lipopeptides and High Molecular Weight Biosurfactants." In: Handbook of Hydrocarbon and Lipid Microbiology, K. N. Timmis (Editor). pp. 3687-3704.
Ajesh K. & Sreejith K., 2013. "Purification and characterization of antifungal lipopeptide from a soil isolated strain of Bacillus cereus." In: Worldwide research efforts in the fighting against microbial pathogens: from basic research totechnological developments. A. Mendez-Vilas (editor). pp. 227-231.
Kim SH, Lim EJ, Lee SO, Lee JD: & Lee TH., 2000. "Purification and characterization of biosurfactants from Nocardia sp." L-417, Biotechnol Appl Biochem. 31 (Pt 3):249-253.
Kim PI, Bai H, Bai D, Chae H, Chung S, Kim Y, Park R, & Chi YT., 2004. "Purification and characterization of a popeptide produced by Bacillus thuringiensis CMB26." J Appl Microbiol. 97(5):942-949.
Baker SC & Chen CY, 2010. "Enrichment and purification of lipopeptide biosurfactants." Adv Exp Med Biol. 672:281-288.
Pablo Vinuesa, Genotypic Characterization of Bradyrhizobium Strains Nodulating Endemic Woody Legumes of the Canary Islands by PCR-Restrictions Fragment Length Polymorphism Analysis of Genes Encoding 16S rRNA (16S rDna) and 16S-23S rDNA IntergenicSpacers, Repetitive Extragenic Palindromic PCR Genomic Fingerprinting, and partial 16S rDNA Sequencing, Applied and Environmental Microbiology, Jun. 1998, p. 2096-2104, vol. 64, No. 6, pp. 9, American Society for Microbiology, America.
Calvo P. et al.: "Agricultural uses of plant biostimulants", Plant Soil, May 8, 2014.
Mohamedova, M. at al.: "Effect of the rhizobacterium Bacillus subtilis on the development of the root-knot nematode Meloidogyne arenaria at different temperatures", Agricultural Science and Technology, vol. 3, No. 4, pp. 78-383, 2011.
Wei, L. et al.: "Isolation and Characterization of a Rhizobacterial Antagonist of Root-Knot Nematodes", Plos One, Jan. 2014, vol. 9, Issue 1, e85988.
Korbel, M. et al.: "Bacillus and Streptomyces were selected as broad-spectrum antagonists against soilborne pathogens from arid areas in Egypt", FEMS Microbiol Lett 342 (2013) 168-178.
Borriss, R.: "Use of Plant-Associated Bacillus Strains as Biofertilizers and Biocontrol Agents in Agriculture", Bacteria in Agrobiology: Plant Growth Responses, Editors: Maheshwari, Dinesh K (Ed.) 2011, Chapter 3, Springer-Verlag Berlin Heidelberg2011, pp. 41-76.
Ongena, M. et al.: "Bacillus lipopeptides: versatile weapons for plant disease biocontrol", Trends in Microbiology, vol. 16 No. 3, 2007.
Salinas, K. A. et al.: "Effects of Kodiak (Bacillus subtilis Strain GBO3) on Soil-Inhabiting Nematodes Near the Rhizosphere of Treated versus Untreated Snap Bean Seeds In Situ", Journal of Sustainable Agriculture, vol. 29(3) 2006.
Wu, L. et al.: "Bacilysin from Bacillus amyloliquefaciens FZB42 Has Specific Bactericidal Activity against Harmful Algal Bloom Species", Applied and Environmental Microbiology, p. 7512-7520, Dec. 2014 vol. 80 No. 24.
Joshi, R. et al.: "Identification and Characterization of Novel Genetic Markers Associated with Biological Control Activities in Bacillus subtilis", The American Phytopathological Society, vol. 96, No. 2, 2006.
Li, X.-Y. et al.: "Diversity and Active Mechanism of Fengycin-Type Cyclopeptides from Bacillus subtilis XF-1 Against Plasmodiophora brassicae", J. Microbiol. Biotechnol. (2013); 23(3), 313-321.
Hu, L. B. et al.: "Fengycin antibiotics isolated from B-FS01 culture inhibit the growth of Fusarium moniliforme Sheldon ATCC 38932", FEMS Microbiol Lett 272 (2007) 91-98.
Vanittanakom, N. et al.: "Fengycin—A Novel Antifungal Lipopeptide Antibiotic Produced by Bacillus Subtilis F-29-3", The Journal of Antibiotics, Jul. 1986, vol. XXXIX No. 7.
Scholz, R. et al.: "Amylocyclicin, a novel circular 1 bacteriocin produced by Bacillus amyloliquelaciens FZB42" JB Accepts, published online ahead of print on Mar. 7, 2014, J. Bacteriol doi:10. 1128/JB.01474-14.
Kalyon: B. et al.: "Plantazolicin A and B: Structure Elucidation of Ribosomally Synthesized Thiazole/Oxazole Peptides from Bacillus amyloliquefaciens FZB42", Org. Lett. 2011, 13 (12), pp. 2996-2999.
Chen, X. H. et al.: "Comparative analysis of the complete genome sequence of the plant growth-promoting bacterium Bacillus amyloliquefaciens FZB42", Nature Biotechnology, vol. 25, No. 9, Sep. 2007.

(56) References Cited

OTHER PUBLICATIONS

Idriss, E. E. et al.: "Extracellular phytase activity of Bacillus amyloliquefaciens FZB45 contributes to its plant-growth-promoting effect", Microbiology (2002), 14.8, 2097-2109.

Adam, M. et al.: "Bacterial Antagonists of Fungal Pathogens Also Control Root-Knot Nematodes by Induced Systemic Resistance of Tomato Plants", Plos One, Feb. 2014, vol. 9, Issue 2. e90402.

Baruzzi, F. et al.: "Antimicrobial compounds produced by Bacillus spp. and applications infood", Formatex 2011. pp. 1102-1111.

Li, X.-Y. et al.: "ESI LC-MS and MS/MS Characterization of Antifungal Cyclic Lipopeptides Produced by Bacillus subtilis XF-1", J Mol Microbiol Biotechnol 2012;22183-93.

Pathak, K. V. et al.: "Identification of surfactins and iturins produced by potent fungal antagonist, Bacillus subtilis K1 isolated from aerial roots of banyan (Ficus benghalensis) tree using mass spectrometry", 3 Biotech (2014) 4:283-295.

Gong, A.-D. et al.: "Antagonistic Mechanism of Iturin A and Plipastatin A from Bacillus amyloliquefaciens S76-3 from Wheat Spikes against Fusarium graminearum", Plos One, DOI:10.1371/journal.pone.0116871, Feb. 17, 2015.

Niazi, A. et al.: "Genome Analysis of Bacillus amyloliquefaciens Subsp. plantarum UCMB5113: A Rhizobacterium That Improves Plant Growth and Stress Management", Plos One, Aug. 2014, vol. 9, Issue 8, e104651.

Arguelles-Arias, A. et al.: "Bacillus amyloliquefaciens GA1 as a source of potent antibiotics and other secondary metabolites for biocontrol of plant pathogens", Microbial Cell Factories 2009, 8:63.

Luo, C. et al.: "Nonribosomal Peptide Synthase Gene Clusters for Lipopeptide Biosynthesis in Bacillus subtilis 916 and Their Phenotypic Functions", Applied and Environmental Microbiology, Jan. 2015, vol. 81, No. 1.

Patel, H. et al,: "All-or-none membrane permeabilization by fengycin-type lipopeptides from Bacillus subtilis QST713", Biochimica et Biophysica Acta 1808 (2011) 2000-2008.

Cawoy, H. et al.: "Lipopeptides as main ingredients for inhibition of fungal phytopathogens by Bacillus subtilis/amyloliquefaciens", Microbial Biotechnology, 8, 281-295, 2014.

Abriouel, H. et al.: "Diversity and applications of Bacillus bacteriocins", FEMS Microbiol Rev 35 (2011) 201-232.

Chalterjee, C. et al.: "Biosynthesis and Mode of Action of Lantibiotics", Chem. Rev. 2005, 105, 633-683.

Stein, T.: "Bacillus subtilis antibiotics; structures, syntheses and specific functions", Molecular Microbiology (2005) 56 (4), 845-857.

Burkett-Cadena, M. et al.: "Suppressiveness of root-knot nematodes mediated by rhizobacteria", Biological Control 47 (2008) 55-59.

Lahlali, R. et al.: "Mechanisms of the biofungicide Serenade (Bacillus subtilis QST713) in suppressing clubroot", Biocontrol Science and Technology, vol. 21, No. 11, Nov. 2011, 1351-1362.

Edgecomb, D. W. et al.: "Bacillus subtilis, Strain QST 713 Use in Integrated Pest Management", Annual Biocontrol Industry Meeting, Oct. 24, 2006 (Oct. 24, 2006), pp. 1-16, XP055071249, Lucerne, Switzerland.

Kloepper, J. W. et al.: "Induced Systemic Resistance and Promotion of Plant Growth by Bacillus spp", Phytopathology, 2004, vol. 94, No. 11, 1259-1266.

Alley, M. et al.: "Pop-up and/or Starter Fertilizers for Corn", 2010, http://pubs.ext.vt.edu/3002/3002-1438/3002-1438.html.

Nielsen, R.L.: "Root development in Young Corn", 2013, http://www.agry.purdue.edu/ext/com/news/timeless/roots.html.

International Search Report and Written Opinion dated Apr. 11, 2016 in International Patent Application No. PCT/US2015/067668 (12 pages).

International Search Report and Written Opinion dated Mar. 11 2016 in International Patent Application No. PCT/US2015/067607 (12 pages).

ATCC Certificate of Deposit, Bacillus amyloliquefaciens RTI301 deposited as ATCC Deposit Accession No. PTA-121165, Bacillus subtilis RTI477, ATCC Deposit Accession No. PTA-121167. Apr. 17, 2014. (2 pages).

AgroNews, Certis' Double Nickel Fungicide Registered in California (http://news.agropages.com/news//newDetail) Jul. 25, 2012. (2 pages).

Crowe, G.: "BCS Biologics Product Overviews", Bayer CropScience, http://www.laca1.org/Presentations/2013/Product%20Overview%20La%20Crop%20-Consult. (Dec. 31, 2013).

Certis USA, L.L.C., DoubleNickel55 label, https://web.archive.org/web/20140916093341/http://certisusa.com/pest.sub.—management.sub.—products/biofungicides/doublenickel55.sub.—fungicide.htm (Sep. 16, 2014).

Bion Tech Inc., BIOBAC (Bacillus subtilis) label, http://www.biontech.com.tw/biopesticides/item/5-biobac-wp.html Jul. 17, 2013.

Agri Life, Bionemagon Material Safety Data Sheet, http://web.archive.org/web/20130814063124/http://argilife.in/pdf/biopesti-cides/biopesti.sub.—micro/msds/msds.sub.—bionemagon.sub.—liquid.pdf Aug. 14, 2013.

BASF—Becker Underwood, Inc., Subtilex NG label, https://web.archive.org/web/20140418120028/http://agproducts.basf.us/products/subtilex-ng-bio-fungicide.html Apr. 18, 2014.

Bayer, Nortica Material Safety Data Sheet, http://www.domyownpestcontrol.com/msds/Nortica.sub.—MSDS Jun. 1, 2010.

ABiTEP GmbH, RhizoVital 42 label, http://www.gardencityplastics.com/UserFiles/Documents/Product/Instruction-%20for%20use%20RhizoVital%C2%AE%2042%20liquid Jun. 18, 2007.

Bayer CropScience LP, Poncho / Votivo label. (2011).

Bayer CropScience LP, Sonata label. (2014).

Bayer CropScience LP, Yield Shield label. (2011).

Bayer CropScience LP, Serenade ASO label. (2013).

Bayer CropScience Inc., Serenade CPB label. (2010).

Bayer CropScience Inc., Serenade MAX label. (2011).

Bayer CropScience LP, Serenade Optimum label. (2013).

Bayer CropScience LP, Serenade Soil label. (2013).

Helena Chemical Company, System 3 Seed Treatment (contains Kodiak) specimen label. (2002).

AgraQuest Inc., Ballad Plus label. (2007).

JH Biotech, Inc., Fulzyme Jan. 10, 2012 Natural Activator label. (2012).

BASF Corporation, Xanthion In-furrow fungicide label. (2014).

* cited by examiner

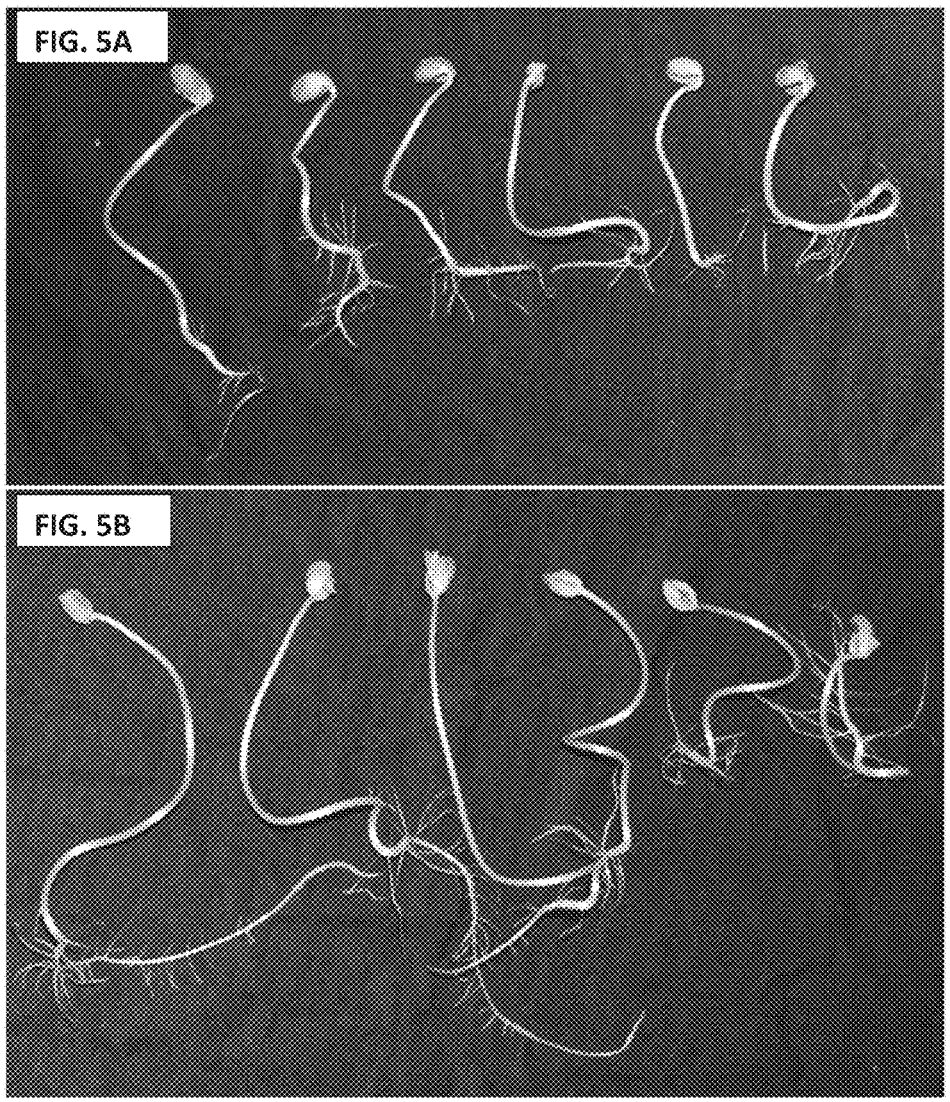

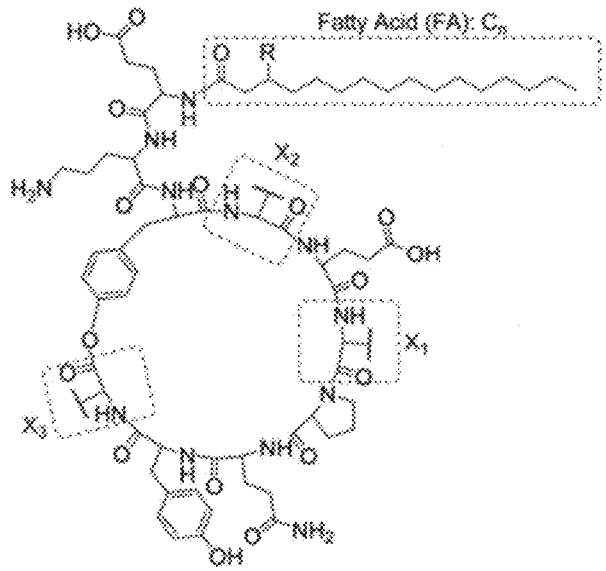

|  | $X_1$ | $X_2$ | $X_3$ | $X_4$ | R | Fatty Acid Observed for RTI301 | Fatty Acid Observed for RTI477 | Theoretical C16 [M+H]+ |
|---|---|---|---|---|---|---|---|---|
| Fengycin A | Ala | Thr | Ile | Tyr | OH | C15, C16, C17 | C14, C15, C16, C17 | 1463.8 |
| Fengycin B | Val | Thr | Ile | Tyr | OH | C14, C15, C16, C17 | C14, C15, C16, C17 | 1491.8 |
| Fengycin C | Aba | Thr | Ile | Tyr | OH | C14, C15, C16, C17 | C14, C15, C16, C17 | 1477.8 |
| Fengycin D | Val | Thr | Val | Tyr | OH | C14, C15, C16, C17 | C14, C15, C16, C17 | 1477.8 |
| Fengycin S | Val | Ser | Ile | Tyr | OH | C14, C15, C16, C17 | C14, C15, C16, C17 | 1477.8 |
| Fengycin I | Ile | Thr | Ile | Tyr | OH | C16, C17 | C16 | 1505.8 |
| Fengycin MA | Ala | Thr | Met | Tyr | OH | C15, C16, C17 | C15, C16, C17 | 1481.8 |
| Fengycin MB | Val | Thr | Met | Tyr | OH | C14, C15, C16 | C14, C15, C16, C17 | 1509.8 |
| Fengycin MC | Aba | Thr | Met | Tyr | OH | C14, C15, C16, C17 | C14, C15, C16, C17 | 1495.8 |
| Fengycin H | Val | Thr | Hcy | Tyr | OH | C14, C15, C16, C17 | C14, C15, C16, C17 | 1495.8 |
| Dehydroxyfengycin A | Ala | Thr | Ile | Tyr | H | C15, C16, C17 | C14, C15, C16, C17 | 1447.8 |
| Dehydroxyfengycin B | Val | Thr | Ile | Tyr | H | C14, C15, C16, C17 | C14, C15, C16, C17 | 1475.8 |
| Dehydroxyfengycin C | Aba | Thr | Ile | Tyr | H | C14, C15, C16, C17 | C14, C15, C16, C17 | 1461.8 |
| Dehydroxyfengycin D | Val | Thr | Val | Tyr | H | C14, C15, C16, C17 | C14, C15, C16, C17 | 1461.8 |
| Dehydroxyfengycin S | Val | Ser | Ile | Tyr | H | C14, C15, C16, C17 | C14, C15, C16, C17 | 1461.8 |
| Dehydroxyfengycin I | Ile | Thr | Ile | Tyr | H | C15, C16, C17 | C15, C16, C17 | 1489.9 |
| Dehydroxyfengycin MA | Ala | Thr | Met | Tyr | H | C14 | Not observed | 1465.8 |
| Dehydroxyfengycin MB | Val | Thr | Met | Tyr | H | C15 | Not observed | 1493.8 |
| Dehydroxyfengycin MC | Aba | Thr | Met | Tyr | H | C15 | Not observed | 1479.8 |
| Dehydroxyfengycin H | Val | Thr | Hcy | Tyr | H | C14, C15, C16 | Not observed | 1479.8 |

FIG. 6

SEQUENCE LISTING

<160> NUMBER OF SEQ ID NOS: 4

<210> SEQ ID NO 1
<211> LENGTH: 1556
<212> TYPE: DNA
<213> ORGANISM: Bacillus subtilis

<400> SEQUENCE: 1
atttatcgga gagtttgatc ctggctcagg acgaacgctg gcggcgtgcc taatacatgc     60
aagtcgagcg gacagatggg agcttgctcc ctgatgttag cggcggacgg gtgagtaaca    120

```
cgtgggtaac ctgcctgtaa gactgggata actccgggaa accggggcta ataccggatg    180
gttgtttgaa ccgcatggtt caaacataaa aggtggcttc ggctaccact tacagatgga    240
cccgcggcgc attagctagt tggtgaggta atggctcacc aaggcaacga tgcgtagccg    300
acctgagagg gtgatcggcc acactgggac tgagacacgg cccagactcc tacgggaggc    360
agcagtaggg aatcttccgc aatggacgaa agtctgacgg agcaacgccg cgtgagtgat    420
gaaggttttc ggatcgtaaa gctctgttgt tagggaagaa caagtaccgt tcgaataggg    480
cggtaccttg acggtaccta accagaaagc cacggctaac tacgtgccag cagccgcggt    540
aatacgtagg tggcaagcgt tgtccggaaa ttattgggcg taaagggctc gcaggcggtt    600
tcttaagtct gatgtgaaag cccccggctc aaccggggag ggtcattgga aactgggaa    660 cttgagtgca agaggagga gtggaattcc acgtgtagcg gtgaaatgcg tagagatgtg    720
gaggaacacc agtggcgaag gcgactctct ggtctgtaac tgacgctgag gagcgaaagc    780
gtggggagcg aacaggatta gataccctgg tagtccacgc cgtaaacgat gagtgctaag    840
tgttaggggg tttccgcccc ttagtgctgc agctaacgca ttaagcactc cgcctgggga    900
gtacggtcgc aagactgaaa ctcaaaggaa ttgacggggg cccgcacaag cggtggagca    960
tgtggtttaa ttcgaagcaa cgcgaagaac cttaccaggt cttgacatcc tctgacaatc    1020
ctagagatag gacgtcccct cggggggcag agtgacaggt ggtgcatggt tgtcgtcagc    1080
tcgtgtcgtg agatgttggg ttaagtcccg caacgagcgc aacccttgat cttagttgcc    1140
agcattcagt tgggcactct aaggtgactg ccggtgacaa accggaggaa ggtggggatg    1200
acgtcaaatc atcatgcccc ttatgacctg ggctacacac gtgctacaat ggacagaaca    1260
aagggcagcg aaaccgcgag gttaagccaa tcccacaaat ctgttctcag ttcggatcgc    1320
agtctgcaac tcgactgcgt gaagctgaa tcgctagtaa tcgcggatca gcatgccgcg    1380
gtgaatacgt tcccgggcct tgtacacacc gcccgtcaca ccacgagagt ttgtaacacc    1440
cgaagtcggt gaggtaacct tttaggagcc agccgccgaa ggtgggacag atgattgggg    1500
tgaagtcgta acaaggtagc cgtatcggaa ggtgcggctg gatcacctcc tttcta         1556
```

<210> SEQ ID NO 2
<211> LENGTH: 3441
<212> TYPE: DNA
<213> ORGANISM: Bacillus subtilis

<400> SEQUENCE: 2

```
atgtttcaag acatatcacc aattgaggat ttcactggta acctctctct tgagttcatt     60
gattatagtt taggtgagcc taaatatcct gtagaggaat caaaagaacg tgatgtgact    120
tactcagctc cgctaagagt gaaggttcgt ttaattaaca agaaactgg agaggtaaaa    180 gaccaagatg tcttcatggg tgatttccct attatgacag atacaggtac ttttatcatt    240
aacggtgcgg aacgtgttat cgtttcccag cttgttcggt ctccaagtgt atatttcagt    300
ggtaaagtag acaaaaacgg taaaaaaggt tttaccgcaa ctgtcattcc aaaccgtggc    360
gcatggttag aatacgaaac tgatgcgaaa gatgttgttt atgtccgcat tgatcgcaca    420
cgtaagttgc cggttacggt tcttttgcgt gctctcggct tcggctccga tcaagagatt    480
cttgatctca taggagaaaa cgaatacctg cgaaatacgc ttgataaaga taacacagaa    540
aacagcgaca aagcgttgct ggaaatttac gagcgtctcc gtcctggaga gccgcctaca    600
gtagaaaatg cgaaaagctt gcttgattct cgtttctttg atccgaaacg atacgatctt    660
gccaatgtag gacgctataa aattaataaa aaacttcata ttaagaatcg cctcttcaat    720
```

```
cagagacttg ctgaaacgct tgttgatcct gaaacaggag aaatccttgc tgaaaaggt      780 cagattcttg atagaagaac acttgataaa gtactgccat acttagaaaa cggaatcggt    840
tttagaaagc tgtatccgaa tggcggcgtt gttgaagatg aagtgactct tcaatcaatt    900
aaaatctttg ctccgactga tcaagaagga gaacaggtta ttaatgtaat cggcaatgct    960
tacatcgaag aagagattaa aaacatcacg cctgctgata ttatttcttc aatcagctac   1020
ttcttcaacc tgctgcacgg agtaggcgac acagatgata tcgatcatct tggaaaccgc   1080
cgtttacgtt ctgtaggtga gcttctccag aaccaattcc gtatcggttt aagccgtatg   1140
gagcgtgtgg ttcgtgagag aatgtcaatt caagatacga atacaattac gcctcagcag   1200
ctgatcaata ttcgtcctgt tattgcgtcc attaaagagt tctttggaag ctcacagctt   1260
tctcaattca tggatcagac gaacccgctt gctgaattaa cgcacaagcg tcgtctgtca   1320
gcattaggac cgggtggatt gacacgtgag cgtgccggaa tggaagtgcg tgacgttcac   1380
tactcccact atggccgtat gtgtccgatt gaaacgcctg agggcccgaa catcggtttg   1440
atcaactcac tatcatctta tgcaaaagta aaccgttttg ctttattga aacgccatat    1500 cgccgcgttg accctgaaac agggaaggta acgggcagaa tcgattactt aactgctgat   1560
gaagaggata actatgttgt cgctcaagcg aatgctcgtc ttgatgacga aggcgccttt   1620
attgatgaca gcatcgtagc tcgtttccgc ggggagaaca ccgttgtttc cagaaatcgt   1680
gtagactaca tggatgtatc gcctaagcag gttgtatctg ctgcgacagc atgtatcccg   1740
ttcttagaaa acgatgactc caaccgtgcc ctcatgggag cgaacatgca gcgtcaggct   1800
gtgcctttga tgcagccgga agcgccattt gttggaactg gtatggaata cgtatcagga   1860
aaagactctg gtgccgctgt tatttgtaaa caccctggta tcgttgaacg cgtagaagcg   1920
aaaaacgttt gggttcgccg ttatgaagaa gtagacggtc aaaaagtaaa aggaaacctg   1980
gataaataca gcctgctgaa atttgtccgc tctaaccaag gtacgtgcta caaccagcgt   2040
ccgatcgtaa gtgtcggcga tgaagtggta aaaggagaaa tccttgctga cggtccttct   2100
atggagcttg gtgaacttgc acttggccgt aacgtaatgg tcggcttcat gacatgggat   2160
ggctacaact atgaggatgc catcatcatg agtgaacgcc tagtgaagga tgatgtttat   2220
acatctatcc acattgaaga atacgaatca gaagcacgtg atacgaaact tggacctgaa   2280
gaaatcactc gcgatattcc aaacgtcggt gaagatgcgc ttcgcaatct tgatgaccgc   2340
ggaatcatcc gtattggggc agaagtaaaa gacggagatc ttcttgttgg taaagtaacg   2400
cctaaaggcg taactgaact gactgcagaa gaacgccttc ttcacgccat ctttggcgag   2460
aaagcccgcg aggttcgtga tacttctctt cgtgtgcctc atggcggcgg cggaattatc   2520
catgacgtta aagtcttcaa ccgtgaagac ggagacgaac ttcctccagg tgttaaccag   2580
ttagtacgcg tatatatcgt tcagaaacgt aagatttctg aagggggataa aatggccggt   2640 cgtcacggta acaaaggtgt tatctctaag attcttcctg aagaggatat gccttacctt   2700
cctgacggca caccaattga tatcatgctt aacccgctgg gcgtaccatc acgtatgaac   2760
atcgggcagg tattggaact tcacatgggt atggccgctc gttaccttgg cattcacatt   2820
gcatctcctg tatttgacgg agcgcgagaa gaggatgtct gggaaacact tgaagaagcc   2880
ggcatgtctc gtgacgccaa aacagtgctt tacgacggac gtactggaga gccgtttgat   2940
aaccgtgtat ctgtcggtat catgtacatg atcaaactag ctcacatggt tgacgataaa   3000
cttcatgcac gctctacagg cccttactca cttgttacgc agcagcctct tggcggtaaa   3060
```

```
gcgcaatttg gcggacagcg ttttggtgag atggaggttt gggcacttga agcttacggt   3120
gcggcttaca ctcttcaaga aattctgact gttaagtctg atgacgtggt tggacgtgtg   3180
aaaacatacg aagccatcgt taaaggcgac aatgttcctg aaccaggtgt tccggaatca   3240
ttcaaagtat taatcaaaga acttcaaagc ttaggtatgg atgtcaaaat cctttctggt   3300
gatgaagaag aaatagaaat gagagattta gaagacgaag aagatgcgaa acaagctgac   3360
ggcctggcat tatcaggtga tgaagagccg gaagaaacag catctgcaga cgttgaacgc   3420
gatgtagtaa caaaagaata a                                              3441

<210> SEQ ID NO 3
<211> LENGTH: 1554
<212> TYPE: DNA
<213> ORGANISM: Bacillus amyloliquefaciens

<400> SEQUENCE: 3
ctttatcgga gagtttgatc ctggctcagg acgaacgctg gcggcgtgcc taatacatgc     60
aagtcgagcg gacagatggg agcttgctcc ctgatgttag cggcggacgg gtgagtaaca    120
cgtgggtaac ctgcctgtaa gactgggata actccgggaa accggggcta ataccggatg    180
gttgtctgaa ccgcatggtt cagacataaa aggtggcttc ggctaccact tacagatgga    240
cccgcggcgc attagctagt tggtgaggta acggctcacc aaggcaacga tgcgtagccg    300
acctgagagg gtgatcggcc acactgggac tgagacacgg cccagactcc tacgggaggc    360
agcagtaggg aatcttccgc aatggacgaa agtctgacgg agcaacgccg cgtgagtgat    420
gaaggttttc ggatcgtaaa gctctgttgt tagggaagaa caagtgccgt tcaaataggg    480
cggcaccttg acggtaccta accagaaagc cacggctaac tacgtgccag cagccgcggt    540
aatacgtagg tggcaagcgt tgtccggaat tattgggcgt aaagggctcg caggcggttt    600
cttaagtctg atgtgaaagc ccccggctca accggggagg gtcattggaa actggggaac    660
ttgagtgcag aagaggagag tggaattcca cgtgtagcgg tgaaatgcgt agagatgtgg    720
aggaacacca gtggcgaagg cgactctctg gtctgtaact gacgctgagg agcgaaagcg    780
tggggagcga acaggattag ataccctggt agtccacgcc gtaaacgatg agtgctaagt    840 gttaggggt tccgccccct tagtgctgca gctaacgcat taagcactcc gcctggggag    900
kacggtcgca agactgaaac tcaaaggaat tgacggggc cgcacaagc ggkggagcat    960 gtggtttaat tcgaagcaac gcgaagaacc ttaccaggtc ttgacatcct ctgacaatcc    1020
tagagatagg acgtcccctt cggggcaga gtgacaggtg gtgcatggtt gtcgtcagct    1080
cgtgtcgtga tgttgggt taagtcccgc aacgagcgca acccttgatc ttagttgcca    1140
gcattcagtt gggcactcta aggtgactgc cggtgacaaa ccggaggaag gtggggatga    1200
cgtcaaatca tcatgcccct tatgacctgg gctacacacg tgctacaatg gacagaacaa    1260
agggcagcga aaccgcgagg ttaagccaat cccacaaatc tgttctcagt tcggatcgca    1320
gtctgcaact cgactgcgtg aagctggaat cgctagtaat cgcggatcag catgccgcgg    1380
tgaatacgtt cccgggcctt gtacacaccg cccgtcacac cacgagagtt tgtaacaccc    1440
gaagtcggtg aggtaacctt tatggagcca gccgccgaag gtgggacaga tgattggggt    1500
gaagtcgtaa caaggtagcc gtatcggaag gtgcggctgg atcacctcct ttct          1554

<210> SEQ ID NO 4
<211> LENGTH: 3246
<212> TYPE: DNA
<213> ORGANISM: Bacillus amyloliquefaciens
```

<400> SEQUENCE: 4

```
atgggtgatt tccctattat gacagatacc ggtactttta tcatcaacgg tgcagaacgt      60
gttatcgtat ctcagcttgt tcggtctcca agtgtatatt tcagtggtaa agtagacaag     120
aacggtaaaa aaggttttac cgcgactgtc attccaaacc gtggcgcatg gttagaatac     180
gaaactgatg cgaaagatgt tgtgtatgtc cgcattgatc gcacacgtaa gttgccggtt     240
acggttcttt tgcgtgctct cggcttcggt tccgaccaag agattctcga tctcattggt     300
gagaacgaat atctccgcaa tacactggat aaggacaaca ctgaaaacag tgacaaagcg     360
cttcttgaaa tctatgagcg ccttcgtccc ggagagccgc ctacagtaga aaacgcaaaa     420
agcttgctgg attcccgttt cttcgatccg aagcgatacg accttgcgaa tgtaggacgc     480
tataaaatta taaaaagct tcatatcaag aaccgcctgt taaccagcg ccttgcagaa      540
acactggtgg atccggaaac cggtgaaatt ctcgctgaaa aagggcagat tcttgacaga     600
agaacacttg ataagtact gccatactta gaaaatggaa tcggcttcag aaagctttat      660
cctaacggcg gcgttgtcga ggatgaagtg atgcttcaat ccattaaaat ctatgctcct     720
accgatgcag aaggagagca gacgatcaat gtgatcggca atgcttacat cgaagaggcg     780
attaaaaaca ttacgcctgc tgatattatt tcttctatca gctacttctt caacctcctg     840
cacggagtgg cgacactga tgatatcgac catctcggaa accgccgtct gcgttctgta      900
ggtgagctcc tgcaaaacca attccgtatc ggtttaagcc ggatggaacg tgtcgtacgt     960
gaaagaatgt ctattcaaga cacgaataca attcgccgc agcagctgat taacatcaga    1020
cctgttattg cgtctattaa agagttcttc ggaagctcac agctttctca attcatggat    1080
cagacgaacc cgcttgctga attgacgcac aaacgccgtc tgtcagctct cggaccgggc    1140
ggtttgacac gtgagcgcgc aggtatggaa gtacgtgacg ttcactactc tcactatggc    1200
cgtatgtgtc cgattgaaac gcctgagggc ccgaacatcg gtttgatcaa ctcattgtca    1260
tcatttgcga aagtaaaccg ctttggtttc attgagacgc cataccgccg cgttgatcct    1320
gaaacaggaa aagtaacgcc tagaatcgac tacctgactg ctgatgaaga ggataactat    1380
gtcgtagccc aagcgaatgc taagctgagc gatgacggtt cttctcttgga tgacagcatc    1440
gtagcgcgtt tcagagggga aaacaccgtt gtagcccgca accgcgtgga ttacatggac    1500
gtatctccta aacaggttgt atctgctgcg acagcatgta ttccgttctt ggaaaacgat    1560
gactcgaacc gcgccctcat gggagcgaac atgcagcgtc aggctgtgcc tttgatgcag    1620
ccggaagctc cgatcgtcgg aacgggtatg gaatacgtat ccggtaaaga ctccggtgca    1680
gccgttattt gtaaacaccc tggtatcgtt gaacgggtgg aagcgaaaaa cgtatgggtg    1740
cgccgctatg aagaaattga cggccaaaaa gtaaaggca acctggataa gtacagcttg     1800
ctgaaatttg tccgctccaa ccaaggtacg tgctacaacc agcgtccgat cgtcagtgtc    1860
ggcgatgaag tagtcaaagg agaaatcctt gctgacggac cttcaatgga gcttggtgaa    1920
cttgctctcg gccgcaacgt aatggtcggc ttcatgacat gggatggtta caactatgag    1980
gatgccatca tcatgagtga acgccttgtg aaagatgatg tatacacatc tattcacatt    2040
gaagaatatg aatcagaagc acgtgataca aagcttgggc cggaagagat cacccgcgat    2100
attccaaacg taggggaaga cgcgcttcgc aatcttgatg accgcggaat tatccgtatc    2160
ggtgcggaag tcaacgacgg agaccttctc gtaggtaaag taacgcctaa aggtgtaact    2220
gagcttacgg ctgaagaacg ccttctgcat gcgatctttg agaaaaagc gcgtgaagtc    2280
```

```
cgtgatactt ctctccgtgt gcctcacggc ggcggcggaa ttatccacga cgtaaaagtc    2340
ttcaaccgtg aagacggcga cgaacttcct ccgggagtga accagcttgt acgcgtatat    2400
atcgttcaga aacgtaagat ttctgaaggt gataaaatgg ccggacgtca cggaaacaaa    2460
ggggttatct cgaagattct tcctgaagaa gatatgcctt accttcctga cggcacgccg    2520
atcgatatca tgcttaaccc gctgggtgta ccatcacgta tgaatatcgg tcaggtatta    2580
gaacttcaca tgggtatggc tgcccgctac ctcggcattc acatcgcgtc acctgtattt    2640
gacggcgcgc gtgaagaaga tgtgtgggaa acacttgaag aagcaggcat gtcaagagac    2700
gctaaaacag ttctttatga cggccgtacg ggtgaaccgt ttgacaaccg tgtatctgtc    2760
ggaatcatgt acatgatcaa actggcacac atggttgatg ataaacttca tgcccgttct    2820
acaggtcctt actcacttgt tacgcagcag cctctcggcg gtaaagccca attcggcgga    2880
cagcgtttcg gtgagatgga ggtttgggcg cttgaagctt acggcgcagc ttacacgctt    2940
caagaaatcc tgactgtgaa gtccgatgac gtggtcggac gtgtgaaaac atatgaagcc    3000
atcgtcaaag gcgacaatgt tccagagcct ggtgttccgg aatcattcaa agtattgatc    3060
aaagagcttc aaagcttagg tatgacgtg aaaatccttt caggcgatga agaagaaata    3120
gaaatgagag atctagaaga cgaggaagat gcgaaacaag ctgacggcct tgcattatca    3180
ggtgatgaag cgccggaaga aacagcatct ccagacgttg aacgtgacgc agtaacgaaa    3240
gaatag                                                              3246
```

MICROBIAL COMPOSITIONS AND METHODS OF USE FOR BENEFITING PLANT GROWTH AND TREATING PLANT DISEASE

CROSS REFERENCE TO RELATED APPLICATIONS

This application is a national phase application of PCT/US15/67668, filed on Dec. 28, 2015, and claims the benefit of U.S. provisional application No. 62/097,287 filed Dec. 29, 2014. The contents of these applications are incorporated herein by reference in their entireties.

TECHNICAL FIELD

The presently disclosed subject matter relates to compositions comprising isolated microbial strains for application to plants, plant seeds, and the soil surrounding plants to benefit plant growth and to treat plant plant disease. In certain cases the microbial strains are delivered to the plants, plant seeds, and the soil surrounding plants in combination with a chemical active agent having antimicrobial properties.

BACKGROUND

A number of microorganisms having beneficial effects on plant growth and health are known to be present in the soil, to live in association with plants specifically in the root zone (Plant Growth Promoting Rhizobacteria "PGPR"), or to reside as endophytes within the plant. Their beneficial plant growth promoting properties include nitrogen fixation, iron chelation, phosphate solubilization, inhibition of non-beneficial microrganisms, resistance to pests, Induced Systemic Resistance (ISR), Systemic Acquired Resistance (SAR), decomposition of plant material in soil to increase useful soil organic matter, and synthesis of phytohormones such as indole-acetic acid (IAA), acetoin and 2,3-butanediol that stimulate plant growth, development and responses to environmental stresses such as drought. In addition, these microorganisms can interfere with a plant's ethylene stress response by breaking down the precursor molecule, 1-aminocyclopropane-1-carboxylate (ACC), thereby stimulating plant growth and slowing fruit ripening. These beneficial microorganisms can improve soil quality, plant growth, yield, and quality of crops. Various microorganisms exhibit biological activity such as to be useful to control plant diseases. Such biopesticides (living organisms and the compounds naturally produced by these organisms) are safer and more biodegradable than synthetic fertilizers and pesticides.

Fungal phytopathogens, including but not limited to *Botrytis* spp. (e.g. *Botrytis cinerea*), *Fusarium* spp. (e.g. *F. oxysporum* and *F. graminearum*), *Rhizoctonia* spp. (e.g. *R. solani*), *Magnaporthe* spp., *Mycosphaerella* spp., *Puccinia* spp. (e.g. *P. recondita*), *Phytopthora* spp. and *Phakopsora* spp. (e.g. *P. pachyrhizi*), are one type of plant pest that can cause servere economic losses in the agricultural and horticultural industries. Chemical agents can be used to control fungal phytopathogens, but the use of chemical agents suffers from disadvantages including high cost, lack of efficacy, emergence of resistant strains of the fungi, and undesirable environmental impacts. In addition, such chemical treatments tend to be indiscriminant and may adversely affect beneficial bacteria, fungi, and arthropods in addition to the plant pathogen at which the treatments are targeted. A second type of plant pest are bacterial pathogens, including but not limited to *Erwinia* spp. (such as *Erwinia chrysanthemi*), *Pantoea* spp. (such as *P. citrea*), *Xanthomonas* (e.g. *Xanthomonas campestris*), *Pseudomonas* spp. (such as *P. syringae*) and *Ralstonia* spp. (such as *R. soleacearum*) that cause servere economic losses in the agricultural and horticultural industries. Similar to pathogenic fungi, the use of chemical agents to treat these bacterial pathogens suffers from disadvantages. Viruses and virus-like organisms comprise a third type of plant disease-causing agent that is hard to control, but to which bacterial microorganisms can provide resistance in plants via induced systemic resistance (ISR). Thus, microorganisms that can be applied as biofertilizer and/or biopesticide to control pathogenic fungi, viruses, and bacteria are desirable and in high demand to improve agricultural sustainability. A final type of plant pathogen includes plant pathogenic nematodes and insects, which can cause severe damage and loss of plants.

Some members of the species *Bacillus* have been reported as biocontrol strains, and some have been applied in commercial products (Joseph W. Kloepper, et al. 2004, *Phytopathology* Vol. 94, No. 11, 1259-1266). For example, strains currently being used in commercial biocontrol products include: *Bacillus pumilus* strain QST2808, used as active ingredient in SONATA and BALLAD-PLUS, produced by BAYER CROP SCIENCE; *Bacillus pumilus* strain GB34, used as active ingredient in YIELDSHIELD, produced by BAYER CROP SCIENCE; *Bacillus subtilis* strain QST713, used as the active ingredient of SERENADE, produced by BAYER CROP SCIENCE; *Bacillus subtilis* strain GBO3, used as the active ingredient in KODIAK and SYSTEM3, produced by HELENA CHEMICAL COMPANY. Various strains of *Bacillus thuringiensis* and *Bacillus firmus* have been applied as biocontrol agents against nematodes and vector insects and these strains serve as the basis of numerous commercially available biocontrol products, including NORTICA and PONCHO-VOTIVO, produced by BAYER CROP SCIENCE. In addition, *Bacillus* strains currently being used in commercial biostimulant products include: *Bacillus amyloliquefaciens* strain FZB42 used as the active ingredient in RHIZOVITAL 42, produced by ABiTEP GmbH, as well as various other *Bacillus subtilus* species that are included as whole cells including their fermentation extract in biostimulant products, such as FULZYME produced by JHBiotech Inc.

The presently disclosed subject matter provides microbial compositions and methods for their use in benefiting plant growth and treating plant disease.

SUMMARY OF THE INVENTION

In one embodiment a composition is provided for benefiting plant growth and/or plant health, the composition comprising: a biologically pure culture of *Bacillus velezensis* RTI301 deposited as ATCC No. PTA-121165, or a mutant thereof having all the identifying characteristics thereof; and a biologically pure culture of *Bacillus subtilis* RTI477 deposited as ATCC No. PTA-121167, or a mutant thereof having all the identifying characteristics thereof, wherein application of the composition to seed of the plant, roots of the plant, or soil surrounding the plant benefits plant growth and/or plant health.

In one embodiment a method is provided for benefiting plant growth and/or plant health, the method comprising delivering to seed of a plant, roots of a plant, or soil surrounding a plant a composition comprising: a biologically pure culture of a *Bacillus velezensis* RTI301 deposited as ATCC No. PTA-121165, or a mutant thereof having all the identifying characteristics thereof; and a biologically pure culture of a *Bacillus subtilis* RTI477 deposited as ATCC No. PTA-121167, or a mutant thereof having all the identifying characteristics thereof, wherein delivery of the composition benefits the plant growth and/or plant health.

In one embodiment a method is provided for benefiting plant growth and/or plant health, the method comprising: delivering to seed of a plant, roots of a plant, or soil surrounding a plant a combination of: a first composition comprising a biologically pure culture of a *Bacillus velezensis* RTI301 deposited as ATCC No. PTA-121165, or a mutant thereof having all the identifying characteristics thereof; and a second composition comprising a biologically pure culture of a *Bacillus subtilis* RTI477 deposited as ATCC No. PTA-121167, or a mutant thereof having all the identifying characteristics thereof, wherein delivery of the combination benefits the plant growth and/or plant health.

In one embodiment a plant seed is provided, wherein the plant seed is coated with a composition for benefiting plant growth and/or plant health, the composition comprising: spores of a biologically pure culture of *Bacillus velezensis* RTI301 deposited as ATCC No. PTA-121165, or a mutant thereof having all the identifying characteristics thereof; and spores of a biologically pure culture of *Bacillus subtilis* RTI477 deposited as ATCC No. PTA-121167, or a mutant thereof having all the identifying characteristics thereof.

In one embodiment, a plant seed is provided, wherein the plant seed is coated with a composition for benefiting plant growth and/or plant health, the composition comprising: spores of a biologically pure culture of *Bacillus velezensis* RTI301 deposited as ATCC No. PTA-121165, or a mutant thereof having all the identifying characteristics thereof; spores of a biologically pure culture of *Bacillus subtilis* RTI477 deposited as ATCC No. PTA-121167, or a mutant thereof having all the identifying characteristics thereof; and a bifenthrin insecticide.

In one embodiment a method is provided for benefiting plant growth and/or plant health, the method comprising planting a seed of a plant in a suitable growth medium, wherein the seed has been coated with a composition comprising: spores of a biologically pure culture of *Bacillus velezensis* RTI301 deposited as ATCC No. PTA-121165, or a mutant thereof having all the identifying characteristics thereof; and spores of a biologically pure culture of *Bacillus subtilis* RTI477 deposited as ATCC No. PTA-121167, or a mutant thereof having all the identifying characteristics thereof, present in an amount suitable to benefit the plant growth and/or plant health.

In one embodiment a composition is provided for benefiting plant growth, the composition comprising: a biologically pure culture of *Bacillus velezensis* RTI301 deposited as ATCC No. PTA-121165, or a mutant thereof having all the identifying characteristics thereof; a biologically pure culture of *Bacillus subtilis* RTI477 deposited as ATCC No. PTA-121167, or a mutant thereof having all the identifying characteristics thereof; and a bifenthrin insecticide.

In one embodiment a composition is provided for benefiting plant growth, the composition comprising: a biologically pure culture of *Bacillus velezensis* RTI301 deposited as ATCC No. PTA-121165, or a mutant thereof having all the identifying characteristics thereof; a biologically pure culture of *Bacillus subtilis* RTI477 deposited as ATCC No. PTA-121167, or a mutant thereof having all the identifying characteristics thereof; and a bifenthrin insecticide, wherein the composition is in a formulation compatible with a liquid fertilizer.

In one embodiment, a composition is provided for benefiting plant growth, the composition comprising: a biologically pure culture of *Bacillus velezensis* RTI301 deposited as ATCC No. PTA-121165, or a mutant thereof having all the identifying characteristics thereof; a biologically pure culture of *Bacillus subtilis* RTI477 deposited as ATCC No. PTA-121167, or a mutant thereof having all the identifying characteristics thereof; and a fungicide comprising one or a combination of an extract from *Lupinus albus* doce, a BLAD polypeptide, or a fragment of a BLAD polypeptide.

In one embodiment, a product is provided, the product comprising: a first composition comprising a biologically pure culture of *Bacillus velezensis* RTI301 deposited as ATCC No. PTA-121165, or a mutant thereof having all the identifying characteristics thereof and a biologically pure culture of *Bacillus subtilis* RTI477 deposited as ATCC No. PTA-121167, or a mutant thereof having all the identifying characteristics thereof; a second composition comprising one or a combination of a microbial, a biological, or a chemical insecticide, fungicide, nematicide, bacteriocide, herbicide, plant extract, plant growth regulator, or fertilizer, wherein the first and second composition are separately packaged; and, optionally, instructions for delivering in an amount suitable to benefit plant growth, a combination of the first and second compositions to: foliage of the plant, bark of the plant, fruit of the plant, flowers of the plant, seed of the plant, roots of the plant, a cutting of the plant, a graft of the plant, callus tissue of the plant; soil or growth medium surrounding the plant; soil or growth medium before sowing seed of the plant in the soil or growth medium; or soil or growth medium before planting the plant, the plant cutting, the plant graft, or the plant callus tissue in the soil or growth medium.

BRIEF DESCRIPTION OF THE FIGURES

FIG. 5A shows control plants. FIG. 5B shows plants inoculated with RTI301 plus RTI477 (ratio 3:1) at $10^6$ cfu/ml. FIGS. 5A-5B are images showing the positive effect on early plant growth resulting from inoculation of soybean seed with the combination of *Bacillus velezensis* RTI301 plus *Bacillus subtilis* strain RTI477 and extracted after 8 days growth according to one or more embodiments of the present invention.

FIG. 6 is a schematic diagram showing both previously reported Fengycin-type and Dehydroxyfengycin-type cyclic lipopeptides produced by microbial species including *Bacillus amyloliquefaciens* and *Bacillus subtilis* and newly identified (shown in bold type) Fengycin- and Dehydroxyfengycin-type molecules produced by one or both of the *Bacillus velezensis* RTI301 and *Bacillus* subtilus RTI477 isolates according to one or more embodiments of the present invention.

DETAILED DESCRIPTION

Figure 1:
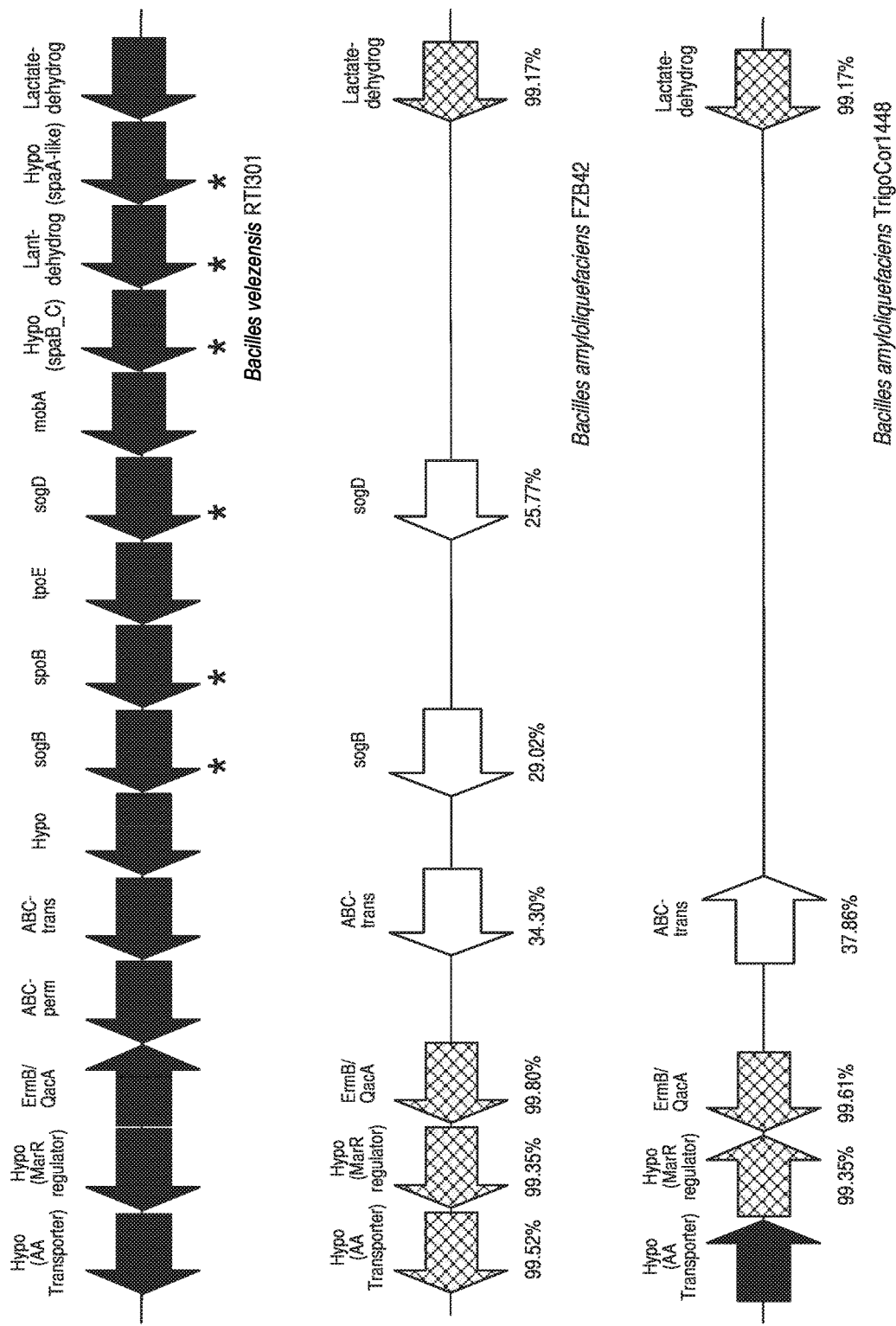
FIG. 1 shows a schematic diagram of the genomic organization surrounding and including the unique lantibiotic biosynthesis operon found in *Bacillus velezensis* strain RTI301 as compared to the corresponding regions for two *Bacillus amyloliquefaciens* reference strains, *Bacillus amyloliquefaciens* FZB42 and *Bacillus amyloliquefaciens* TrigoCor1448 according to one or more embodiments of the present invention.

The terms "a," "an," and "the" refer to "one or more" when used in this application, including the claims. Thus, for example, reference to "a plant" includes a plurality of plants, unless the context clearly is to the contrary.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

For the purposes of this specification and claims, the terms "metabolite" and "compound" are used interchangeably when used in connection with compounds having antimicrobial activity that are produced by the *Bacillus velezensis* RTI301 strain or other *Bacillus amyloliquefaciens* strains. In one or more embodiments of the present invention, compositions and methods are provided for benefiting plant growth and/or plant health. In one embodiment, a composition is provided for benefiting plant growth and/or plant health, the composition including two or more compatible microorganisms, where a first microorganism with antimicrobial properties is used to create a niche by inhibiting the growth and development of endogenous microorganisms present in the soil or living in association with the plant. The second microorganism has properties beneficial to plant growth and/or plant health and is compatible with growth of the first microorganism. The second microorganism is present in an amount sufficient to become established and to benefit the plant growth and/or plant health. Application of the composition to seed of the plant, roots of the plant, or soil surrounding the plant benefits plant growth and/or plant health. The properties of the second microorganism that are beneficial to plant growth and/or plant health include one of increased plant yield, improved seedling vigor, improved root development, improved plant growth, improved plant health, improved appearance, improved resistance to plant pathogens, reduced pathogenic infection, or a combination thereof. The plant pathogen can include one or a combination of insects, nematodes, plant pathogenic fungi, or plant pathogenic bacteria.

In another embodiment, a method is provided for benefiting plant growth and/or plant health, the method comprising delivering to seed of a plant, roots of a plant, or soil surrounding a plant, a composition that includes two or more compatible microorganisms. The composition includes at least one biologically pure culture of a first microorganism having antimicrobial properties and present in an amount suitable for inhibiting growth of endogenous microorganisms present in soil surrounding or living in association with the plant. This is to establish a niche for a second microorganism to become established. The composition also includes at least one biologically pure culture of a second microorganism having properties beneficial to plant growth and/or plant health, wherein growth of the second microorganism is compatible with growth of the first microorganism, and wherein the second microorganism is present in an amount suitable to become established and to benefit the plant growth and/or plant health. Delivery of the composition to seed of the plant, roots of the plant, or soil surrounding the plant benefits the plant growth and/or plant health.

To facilitate the process of establishment of the second microorganism, the growth of the second microorganism can be faster than that of the first microorganism and the second microorganism can be characterized by a swarming and high motility phenotype.

The compositions and methods include use with any type of plant including, for example, monocots, dicots, Cereals, Corn, Sweet Corn, Popcorn, Seed Corn, Silage Corn, Field Corn, Rice, Wheat, Barley, Sorghum, Asparagus, Berry, Blueberry, Blackberry, Raspberry, Loganberry, Huckleberry, Cranberry, Gooseberry, Elderberry, Currant, Caneberry, Bushberry, Brassica Vegetables, Broccoli, Cabbage, Cauliflower, Brussels Sprouts, Collards, Kale, Mustard Greens, Kohlrabi, Cucurbit Vegetables, Cucumber, Cantaloupe, Melon, Muskmelon, Squash, Watermelon, Pumpkin, Eggplant, Bulb Vegetables, Onion, Garlic, Shallots, Citrus, Orange, Grapefruit, Lemon, Tangerine, Tangelo, Pummelo, Fruiting Vegetables, Pepper, Tomato, Ground Cherry, Tomatillo, Okra, Grape, Herbs/Spices, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Coconut, Cotton, Flax, Oil Palm, Olive, Peanut, Rapeseed, Safflower, Sesame, Sunflower, Soybean, Pome Fruit, Apple, Crabapple, Pear, Quince, Mayhaw, Root/Tuber and Corn Vegetables, Carrot, Potato, Sweet Potato, Cassave, Beets, Ginger, Horseradish, Radish, Ginseng, Turnip, Stone Fruit, Apricot, Cherry, Nectarine, Peach, Plum, Prune, Strawberry, Tree Nuts, Almond, Pistachio, Pecan, Walnut, Filberts, Chestnut, Cashew, Beechnut, Butternut, Macadamia, Kiwi, Banana, (Blue) Agave, Grass, Turf grass, Ornamental plants, Poinsettia, Hardwood cuttings, Chestnuts, Oak, Maple, sugarcane, or sugarbeet.

The first microorganism having antimicrobial properties and the second microorganism having properties beneficial to plant growth and/or plant health for use in the compositions and methods of the present invention can be *Bacillus* spp. microorganisms. The terms "antagonistic" and "antimicrobial" are used interchangeably herein for the purposes of the specification and claims. The first microorganism can be a *Bacillus* spp. strain and the *Bacillus* spp. strain can be a *Bacillus* velezensis. The second microorganism having properties beneficial to plant growth and/or plant health can be a *Bacillus subtilis*. The properties beneficial to plant growth and/or plant health can be one or both of growth promoting properties and antagonistic properties to confer protection against plant pathogenic infections and/or to treat or control plant pathogenic infections.

Examples of the first microorganism having antimicrobial properties and the second microorganism having properties beneficial to plant growth and/or plant health for use in the compositions and methods of the present invention are described below. For example, a plant-associated bacterium, identified as belonging to the species *Bacillus subtilis*, was isolated from the root of Moringa oleifera grown in North Carolina and subsequently tested for plant growth promoting and plant pathogen antagonistic properties. More specifically, the isolated bacterial strain was identified as being a new strain of *Bacillus subtilis* through sequence analysis of highly conserved 16S rRNA and rpoB genes (see EXAMPLE 1). The 16S RNA sequence of the new bacterial isolate (designated "*Bacillus subtilis* RTI477") was determined to be identical to the 16S rRNA gene sequence of three other known strains of *Bacillus subtilis, Bacillus amyloliquefaciens* strain NS6 (KF177175), and *Bacillus subtilis* subsp. *subtilis* strain DSM 10 (NR_027552). In addition, it was determined that the rpoB sequence of RTI477 has the highest level of sequence similarity to the known *Bacillus subtilis* PY79 (CP006881) or *Bacillus subtilis* subsp. *subtilis* 6051-HGW (CP003329) strains (i.e., 99% sequence identity; 9 bp difference) or *Bacillus subtilis* subsp. *subtilis* BAB-la (CP004405) (i.e., 99% sequence identity; 10 bp difference). The differences in sequence for the rpoB gene at the DNA level indicate that RTI477 is a new strain of *Bacillus subtilis*. The strain of *Bacillus subtilis* RTI477 was deposited on 17 Apr. 2014 under the terms of the Budapest Treaty on the International Recognition of the Deposit of Microorganisms for the Purposes of Patent Procedure at the American Type Culture Collection (ATCC) in Manassas, Va., USA and bears the Patent Accession No. PTA-121167.

As an example of the first microorganism having antimicrobial properties, a plant-associated bacterium, identified as belonging to the species *Bacillus velezensis*, was isolated from the rhizosphere soil of grape vines growing at a vineyard in NY and subsequently tested for plant pathogen antagonistic properties. More specifically, the isolated bacterial strain was identified as being a new strain of *Bacillus amyloliquefaciens* through sequence analysis of highly conserved 16S rRNA and rpoB genes (see EXAMPLE 2). The 16S RNA sequence of the new bacterial isolate (designated "*Bacillus amyloliquefaciens* RTI301") was determined to be identical to the 16S rRNA gene sequence of three other known strains of *Bacillus amyloliquefaciens, Bacillus amyloliquefaciens* strain NS6 (KF177175), *Bacillus amyloliquefaciens* strain FZB42 (NR_075005), and *Bacillus subtilis* subsp. *subtilis* strain DSM 10 (NR_027552). It was also determined that the rpoB gene sequence of the RTI301 strain has sequence similarity to the same gene in *Bacillus amyloliquefaciens* subsp. *plantarum* TrigoCor1448 (CP007244) (99% sequence identity; 3 base pair difference); *Bacillus amyloliquefaciens* subsp. *plantarum* AS43.3 (CP003838) (99% sequence identity; 7 base pair difference); *Bacillus amyloliquefaciens* CC178 (CP006845) (99% sequence identity; 8 base pair difference), and *Bacillus amyloliquefaciens* FZB42 (CP000560) (99% sequence identity; 8 base pair difference). The RTI301 strain was identified as a *Bacillus amyloliquefaciens*. The differences in sequence for the rpoB gene at the DNA level indicate that RTI301 is a new strain of *Bacillus amyloliquefaciens*. The strain of *Bacillus amyloliquefaciens* RTI301 was deposited on 17 Apr. 2014 under the terms of the Budapest Treaty on the International Recognition of the Deposit of Microorganisms for the Purposes of Patent Procedure at the American Type Culture Collection (ATCC) in Manassas, Va., USA and bears the Patent Accession No. PTA-121165. [The strain was initially deposited under the name "*Bacillus amyloliquefaciens* RTI301", but reclassified as "*Bacillus velezensis* RTI301" on 10 Aug. 2017].

Further sequence analysis of the genome of the *Bacillus velezensis* RTI301 strain revealed that the strain has genes related to lantibiotic biosynthesis for which homologues are lacking in the other closely related *Bacillus velezensis* RTI301 strains (see EXAMPLE 3). This is illustrated in FIG. 1 which shows a schematic diagram of the genomic organization of the unique lantibiotic biosynthetic cluster found in *Bacillus velezensis* RTI301 and the corresponding region for two known *Bacillus amyloliquefaciens* reference strains, FZB42 (middle) and TrigoCor1448 (bottom), shown below the RTI301 strain. It can be observed from FIG. 1 that FZB42 and TrigoCor1448 strains lack many of the genes present in this cluster, and there is a low degree of sequence identity within a number of the genes that are present. BLASTn analysis of this cluster against the non-redundant (nr) nucleotide database at NCBI showed high homology to the 5' and 3' flanking regions (analogous to the high % similarity in FIG. 1) to *B. amyloliquefaciens* strains. However, the lantipeptide biosynthetic cluster was unique to RTI301, and no significant homology to any previously sequenced DNA in the NCBI nr database was observed. The data indicate that the newly identified RTI301 has a unique lantibiotic biosynthesis pathway.

In addition, further sequence analysis of the genome of the *Bacillus velezensis* RTI301 strain revealed that this strain has genes related to a large number of biosynthetic pathways for production of molecules having antimicrobial properties. These include the biosynthetic pathways for subtilosin, surfactin, iturin, fengycins, amylocyclicin, difficidin, bacilysin, bacillomycin, and bacillaene. In contrast to the RTI301 strain with its wide range of antimicrobial biosynthetic pathways, further sequence analysis of the RTI477 strain revealed that this strain has genes related to biosynthetic pathways for a more limited group of molecules having antimicrobial properties. The RTI477 strain has biosynthetic pathways for subtilosin, fengycins, surfactin, difficidin, bacillaene, bacilysin, and bacillomycin, but complete biosynthetic pathways for iturins, lantibiotics, and amylocyclicins were not observed.

Figure 2A:
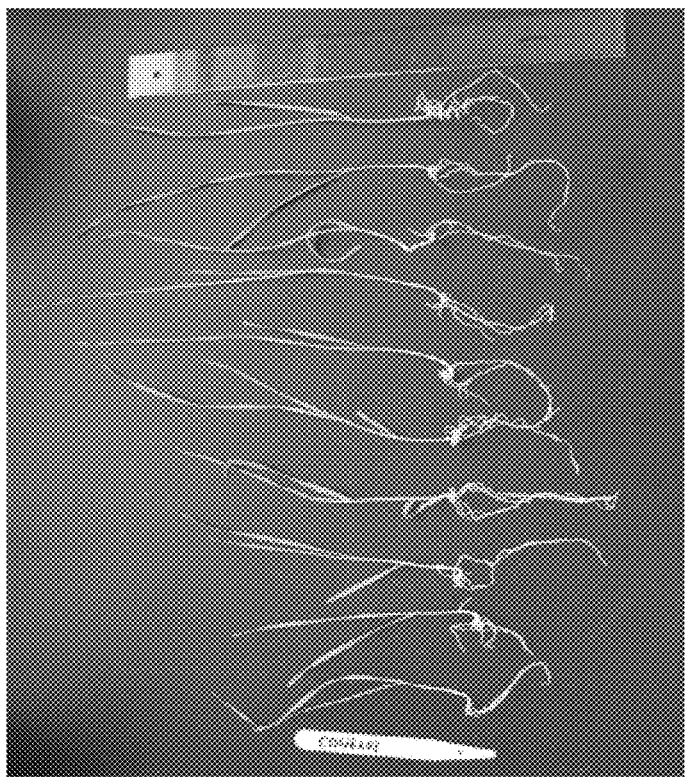
FIG. 2A is an image of extracted wheat plants after 13 days growth showing control plants.
Figure 2B:
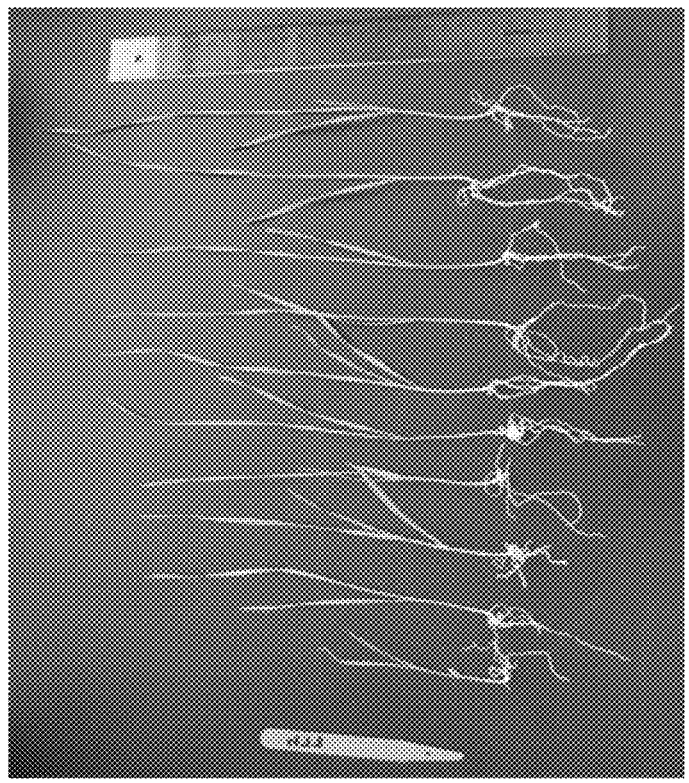
FIG. 2B is an image of extracted wheat plants after 13 days growth showing plants inoculated with the RTI477 strain. These images show the positive effects of *Bacillus subtilis* strain RTI477 on early plant growth in wheat according to one or more embodiments of the present invention.

Experiments were performed to determine the growth promoting and antagonisitic activities of the RTI301 and RTI477 strains. Experiments performed to determine the growth promoting and antagonisitic activities of the *Bacillus subtilis* RTI477 strain in various plants and under varying conditions are described herein at EXAMPLEs 4-6. EXAMPLE 4 describes the antagonistic activity of the *Bacillus subtilis* RTI477 isolate against major plant pathogens as measured in plate assays. EXAMPLE 5 describes measurement of various phenotypic traits of the *Bacillus subtilis* RTI477 isolate and shows that this isolate has a fast growing and strong swarming phenotype. EXAMPLE 6 describes the growth promoting activity of the RTI477 isolate in wheat. Germinated wheat seeds were inoculated for 2 days in a suspension of ~2×10$^7$ CFU/ml of the RTI477 strain and subsequently planted in pots. Photographs of the extracted plants after 13 days growth are shown in FIG. 2. FIG. 2A shows control plants and FIG. 2B shows plants inoculated with RTI477. Dry weight of the wheat seedlings was determined resulting in a total average dry plant weight equal to 35.41 mg for the plants inoculated with the *Bacillus subtilis* RTI477 strain versus a weight equal to 33.38 mg for the non-inoculated control which is a 6% increase in dry weight over the non-inoculated control for the RTI477 treated plants.

Similar to the RTI477 strain, experiments were performed to determine the growth promoting and antagonisitic activities of the *velezensis* RTI301 strain in various plants and under varying conditions. These experiments are described herein at EXAMPLEs 4-5. EXAMPLE 4 describes the antagonistic activity of the *velezensis* RTI301 isolate against major plant pathogens as measured in plate assays. The RTI301 strain showed superior antagonistic properties against a wide range of plant pathogenic microorganisms in comparison to the RTI477 strain. EXAMPLE 5 describes measurement of various phenotypic traits of the *velezensis* RTI301 isolate. Notably, as compared to RTI301, RTI477 grows faster and has a strong swarming phenotype.

Figure 3A:
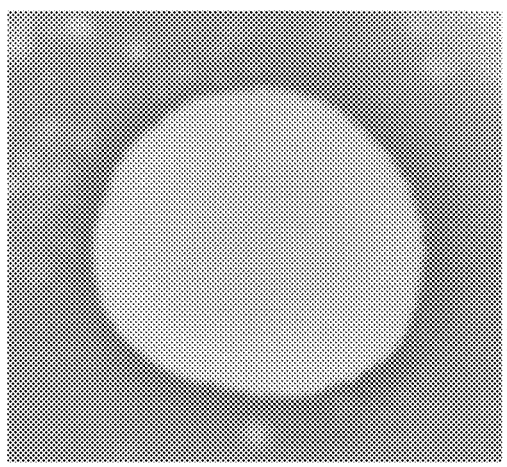
FIG. 3A is an image showing the strain *Bacillus velezensis* RTI301 spotted onto a lawn of strain *Bacillus amyloliquefaciens* RTI472.
Figure 3B:
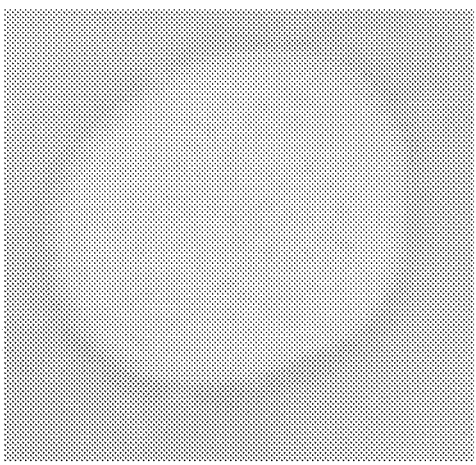
FIG. 3B is an image showing the strain *Bacillus velezensis* RTI301 spotted onto a lawn of strain *Bacillus subtilis* RTI477. These images show the compatibility between *Bacillus velezensis* strain RTI301 and *Bacillus subtilis* strain RTI477 according to one or more embodiments of the present invention.

The compatability of the strain *Bacillus velezensis* RTI301 with other *Bacillus* isolates was tested by spotting the RTI301 strain onto a lawn of the various other strains. These data are described in EXAMPLE 7. Results of this experiment are shown in FIGS. 3A-3B. FIGS. 3A-3B are images showing the growth compatibility between strains *Bacillus velezensis* RTI301 and *Bacillus subtilis* RTI477 and a lack of compatibility between the RTI301 strain with another *Bacillus amyloliquefaciens* strain, *Bacillus amyloliquefaciens* RTI472 deposited as PTA-121166 with the American Type Culture Collection (ATCC). When strain RTI301 was spotted onto a lawn of strain RTI472 (FIG. 3A), a clear inhibition zone was observed for the growth of strain RTI472. In contrast, when strain RTI301 was spotted onto a lawn of strain RTI477 (FIG. 3B), only minimal inhibition and no clearing of the cell lawn was observed for the RTI477 strain. Therefore, it was concluded that the growth of RTI301 and RTI477 is compatible.

Figure 4B:
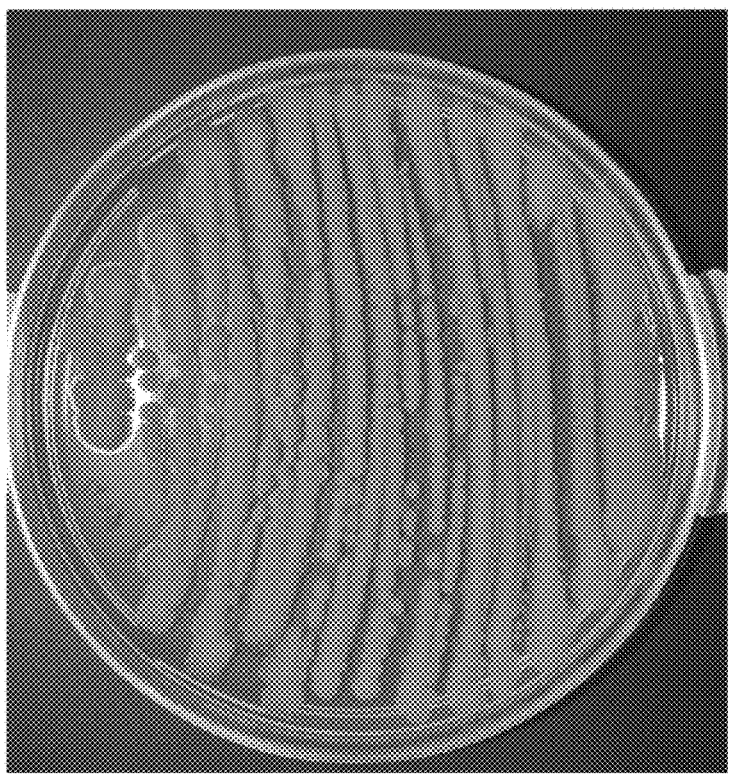
FIG. 4B is an image showing the morphology of strain *Bacillus subtilis* RTI477 according to one or more embodiments of the present invention.
Figure 4A:
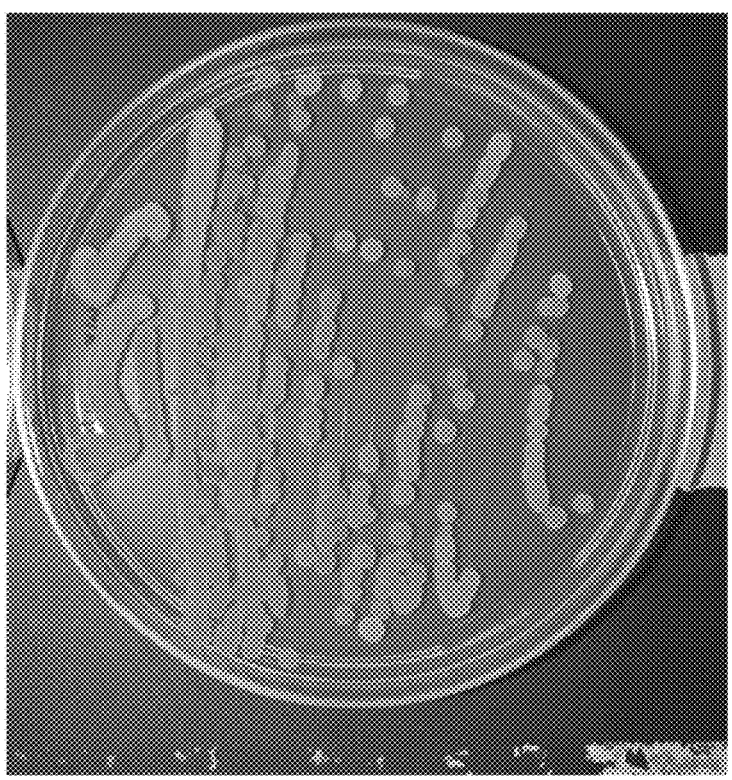
FIG. 4A is an image showing the morphology of strain *Bacillus velezensis* RTI301 according to one or more embodiments of the present invention.

Without being limited to any particular mechanism of action, one mode of action is proposed as follows to explain the observed differences in strain compatibility. Based on the genome sequences of the three strains tested (i.e., RTI301, RTI472, and RTI477), these strains were all predicted to produce the antagonistic compounds bacilysin, bacillaene, difficidin, and bacillomycin. However, while both *Bacillus velezensis* RTI301 and *Bacillus subtilis* RTI477 possess the gene for synthesis of subtilosin, this gene is absent in the genome of *Bacillus amyloliquefaciens* RTI472. Subtilosin is a bacteriocin, a class of proteinaceous toxins produced by bacteria to inhibit the growth of similar or closely related bacterial strain(s). Therefore, it was postulated that the subtilosin synthesized by *Bacillus velezensis* RTI301 could be the inhibitor of the growth of *Bacillus amyloliquefaciens* RTI472. In contrast, the *Bacillus subtilis* RTI477 strain is not inhibited by RTI301, because the RTI477 strain produces its own subtilosin and is thus resistant to the compound. The differences in strain morphology between the *Bacillus velezensis* RTI301 and *Bacillus subtilis* RTI477 strains were also analyzed. Images showing the morphology of each of these strains are shown in FIG. 4: *Bacillus velezensis* RTI301 (FIG. 4A) and *Bacillus subtilis* RTI477 (FIG. 4B). The colony morphology of the *Bacillus velezensis* RTI301 and *Bacillus subtilis* RTI477 strains shown in FIGS. 4A-4B indicate a potential difference in strain behavior when it comes to motility. Motility is a key trait for rhizosphere colonization by plant associated bacteria. *Bacillus velezensis* RTI301 grows as well-defined, round colonies. In contrast, *Bacillus subtilis* RTI477 grows as a fluffy colony, a morphology which is indicative of swarming and motility. Swarming and motility are relevant phenotypes for the rapid colonization of the rhizosphere and the surface of the plant root. Again, without being limited to any particular mechanism of action, it was postulated that the strong swarming phenotype associated with the morphology of the *Bacillus subtilis* RTI477 strain, causes this strain to be a more efficient colonizer of the rhizosphere than *Bacillus velezensis* RTI301.

In light of the growth compatibility and observed differences in phenotype, the combination of the RTI301 and RTI477 strains was tested for its ability to promote plant growth and health. Experiments were performed to determine the effects of application of the *Bacillus subtilis* RTI477 and *Bacillus velezensis* RTI301 strains, alone and in combination, to soybean seed on germination, root development, and early plant growth. Experiments were performed as described in EXAMPLE 8 using spores of RTI301 and RTI477. Combinations of the RTI301 and RTI477 spores were added to the seeds in ratios of 1:3, 1:1 and 3:1. The data are shown in Table V. Inoculation of soybean seeds with *Bacillus velezensis* RTI301 at concentrations of $1\times10^6$, $1\times10^7$, and $1\times10^8$ had no effect on plant growth, and root development and architecture. Inoculation of soybean seeds with *Bacillus subtilis* RTI477 at the same concentrations provided only a slight improvement at the lowest concentration on root development and architecture. However, inoculation of soybean seeds with the combination of both RTI301 and RTI477 (at a ratio of 1:3) resulted at all concentrations tested in an improvement in root development and early plant growth. The best results on root development were observed when RTI301 and RTI477 were applied in a ratio of 3:1 at the concentration of $1\times10^6$ CFU/ml. Images of the positive effects of inoculation of the seed with the RTI301 plus RTI477 spores at this ratio of 3:1 are shown in FIGS. 5A and 5B (A—Control plants; B—plants inoculated with RTI301 plus RTI477 (ratio 3:1) at $10^6$ cfu/ml). The effects were especially positive with regards to root formation and architecture, as shown in FIGS. 5A-5B. Fine root hairs are important in the uptake of water, nutrients and plant interaction with other microorganisms in the rhizosphere. These results show that while the application of individual strains had no or little effect compared to control plants, seed treatment with application of a combination of *Bacillus subtilis* RTI477 and *Bacillus velezensis* RTI301 strains provided a greater than expected benefit to soybean early growth and establishment. Synergistic effects of the combination of the *Bacillus subtilis* RTI477 and *Bacillus velezensis* RTI301 strains were observed and provided unexpected benefits to plant growth.

An additional experiment in soybean was performed to examine the effect of seed treatment with the combination of the RTI301 and RTI477 strains on yield. The experiment was set up as follows: 1) seed was untreated; 2) seed was treated with a combination of CRUISERMAXX (thiamethoxam, fludioxonil plus metalaxyl-M; SYNGENTA CROP PROTECTION, INC) and thiophanate methyl, which is a typical soybean seed treatment (the combination of CRUISERMAXX and thiophanate methyl is referred to as "CHEM CONTROL"); 3) seed was treated with CHEM CONTROL plus inoculated with $5.0\times10^{+5}$ cfu/seed of strain RTI301; 4) seed was treated with CHEM CONTROL plus inoculated with $5.0\times10^{+5}$ cfu/seed of strain RTI477; 5) seed was treated with CHEM CONTROL plus inoculated with a combination of both strains at $5.0\times10^{+5}$ cfu/seed. Ten trials were performed as 10 independent plots and the soybean yield results (bushels per acre) are presented in Table VI. The results in Table VI show that inoculation with either *Bacillus velezensis* RTI301 or *Bacillus subtilis* RTI477 alone had no effect on the overall yield of soybean when compared to seeds that were treated with the CHEM CONTROL alone. As was observed in the previous experiment, inoculating with the combination of the *Bacillus velezensis* RTI301 and *Bacillus subtilis* RTI477 provided a synergistic effect and resulted in a 5% increase in soybean yield (from 58.2 to 61.1 bushels per acre). The combination of the *Bacillus subtilis* RTI477 and *Bacillus velezensis* RTI301 strains provided unexpected benefits to soybean yield.

EXAMPLE 9 describes the benefits of seed treatment with a combination of the *Bacillus subtilis* RTI477 and *Bacillus velezensis* RTI301 strains in corn. For the corn experiment, the data are summarized in Table VII and the set-up was as follows: 1) seed was untreated ("UTC"); 2) seed was treated with a combination of 3 commonly used chemical active agents referred to as "CHEM CONTROL" or "CC"); and 3) seed was treated with CHEM CONTROL plus a combination of $5.0\times10^{+5}$ cfu/seed of each of strains RTI301 and RTI477 ("CC+RTI 301/477 1:1"). Two trials were performed under conditions of natural disease pressure or inoculation of the soil with *Rhizoctonia*. Notably, a yield increase of 10.7 bushels per acre and 59.8 bushels per acre was observed for the 1:1 combination of RTI301 and RTI477 plus chemical control over the chemical control alone for the natural pathogen pressure and the *Rhizoctonia* inoculated field trials, respectively. These data indicate that treatment of seed with the combination of these strains can result in very large enhancements in corn yield.

EXAMPLE 10 describes experiments showing the effect on emergence and yield in soybean when seeds are treated with a combination of the RTI301 and RTI477 strains in addition to chemical active agents for pathogen control. Specifically, an experiment in soybean was set up as follows: 1) seed was untreated (UTC); 2) seed was treated with a combination of 3 commonly used chemical active agents referred to as "CHEM CONTROL"); 3) seed was treated with VIBRANCE (active ingredient Sedaxane; SYNGENTA CROP PROTECTION, INC; and 4) seed was treated with CHEM CONTROL plus $5.0\times10^{+5}$ cfu/seed of each of strain RTI301 and RTI477. Two trials were performed in which the plant seeds were inoculated with *Rhizoctonia solani* at planting. The results in Table VIII show that treating with the combination of the *Bacillus velezensis* RTI301 and *Bacillus subtilis* RTI477 in addition to the CHEM CONTROL resulted in an average increase in yield of 13.3 bushels per acre over that of the CHEM CONTROL alone (from 59.4 to 72.7 bushels per acre). Thus, seed treatment with the combination of RTI301 and RTI477 provides significant improvement in yields in soybean, even under conditions of severe pathogen pressure.

EXAMPLE 11 describes the benefits of drip irrigation with a combination of the *Bacillus subtilis* RTI477 and the *Bacillus velezensis* RTI301 strains on squash, tomato and pepper. Disease pressure caused by soil-borne fungi was not recorded for any of the trails. In the squash trial, spores were applied at a rate of $3.75\times10^{12}$ CFU/hectare for *Bacillus velezensis* RTI301 and $0.625\times10^{12}$ CFU/hectare for *Bacillus subtilis* RTI477 at the time of planting via a root-zone drench, without further application via drip irrigation. ACCOMPLISH LM (LOVELAND PRODUCTS) was used as the commercial control and applied in the same manner as described for the RTI301+RTI477 combination at a rate of 2340 ml/Ha. This product contains a blend of *Acidovorax facilis* ($1\times10^3$ cfu/ml), *Bacillus licheniformis* ($1\times10^3$ cfu/ml), *Bacillus subtilis* ($1\times10^3$ cfu/ml), *Bacillus oleronius* ($1\times10^3$ cfu/ml), *Bacillus marinus* ($1\times10^3$ cfu/ml), *Bacillus megaterium* ($1\times10^3$ cfu/ml), and *Rhodococcus rhodochrous* ($1\times10^3$ cfu/ml). The addition of the RTI301 plus RTI477 spores resulted in an increase in both total and marketable yield for squash compared to untreated control plants in which bacterial spores were not included in the drench, as well as in comparison to the commercial control plants. Specifically, RTI301+RTI477 treated plants resulted in a total of 873.4 kg/Ha squash, as compared to 838.3 kg/Ha and 836.1 kg/Ha for the untreated control plants and the plants treated with ACCOMPLISH, respectively, representing a 4.2% and 4.5% respective increase in weight of total squash. The increase in total squash weight of the plants treated with *Bacillus velezensis* RTI301 plus *Bacillus subtilis* RTI477 spores relative to the untreated control plants and the plants treated with the commercial standard demonstrates the positive growth effect provided by this treatment.

In the tomato trial, spores were applied at a rate of $0.625\times10^{12}$ CFU/hectare for *Bacillus velezensis* RTI301 and $3.75\times10^{12}$ CFU/hectare for *Bacillus subtilis* RTI477 at the time of planting via a root-zone drench, followed by two drip applications of the same rate at 17 and 35 days after transplanting. ACCOMPLISH LM was used as the commercial control and applied in the same manner as described for the RTI301+RTI477 combination at a rate of 2340 ml/Ha. The addition of the RTI301 plus RTI477 spores resulted in an increase in both total and marketable yield for tomatoes compared to untreated control plants in which bacterial spores were not included in the drench and the irrigation, as well as in comparison to the commercial control plants. Specifically, RTI301+RTI477 treated plants resulted in a total of 21,824 kg/Ha marketable tomatoes, as compared to 16,765 kg/Ha and 21,420 kg/Ha for the untreated control plants and the plants treated with ACCOMPLISH, respectively, representing a 30.2% and 1.9% respective increase in weight of marketable tomatoes. The substantial increase in marketable tomato weight of the plants treated with *Bacillus velezensis* RTI301 plus *Bacillus subtilis* RTI477 spores, especially compared to the untreated control plants, demonstrates the positive growth effect provided by this treatment.

In the pepper trial (jalapeno pepper), spores were applied at a rate of $1.25\times10^{12}$ CFU/hectare per strain of both *Bacillus velezensis* RTI301 and *Bacillus subtilis* RTI477 at the time of planting via a root-zone drench, followed by two drip applications of the same rate at 17 and 35 days after transplanting. ACCOMPLISH LM was used as the commercial control and was applied in the same manner as described for the RTI301+RTI477 combination at a rate of 2340 ml/Ha. The addition of the RTI301 plus RTI477 spores resulted in an increase in yield for jalapeno peppers as compared to untreated control plants in which bacterial spores were not applied, as well as in comparison to the commercial control plants. Specifically, RTI301+RTI477 treated plants resulted in a total of 4154 kg/Ha marketable peppers, as compared to 3455 kg/Ha and 3930 kg/Ha for the untreated control plants and the plants treated with ACCOMPLISH, respectively, representing a 20% and a 5.7% respective increase in weight of marketable peppers. The substantial increase in marketable pepper weight of the plants treated with *Bacillus velezensis* RTI301 plus *Bacillus subtilis* RTI477 spores relative to the untreated control plants and the plants treated with the commercial standard demonstrates the positive growth effect provided by this treatment.

Antimicrobial metabolites produced by the RTI301 and FTI477 strains are identified in EXAMPLE 12 and illustrated in FIG. 6. EXAMPLE 12 describes the investigation of the cyclic lipopeptides, Fengycins and Dehydroxyfengycins, produced by the RTI301 and RTI477 strains, and surprisingly, the identification of several previously unreported classes of these molecules. It was determined that *Bacillus velezensis* RTI301 produces the previously reported Fengycin A, B and C compounds and the Dehydroxyfengycin A, B and C compounds. Unexpectantly, in addition to these known compounds, it was determined that the RTI301 strain also produces previously unidentified derivatives of these compounds where the L-isoleucine at position 8 of the cyclic peptide chain (referred to as $X_3$ in FIG. 6) is replaced by L-methionine. The new classes of Fengycin and Dehydroxyfengycin are referred to herein as MA, MB and MC, referring to derivatives of classes A, B and C in which the L-isoleucine at $X_3$ in FIG. 6 has been replaced by L-methionine. The newly identified molecules are shown in FIG. 6 and in Table IX in bold font. The newly identified Fengycin MA, MB and MC compounds were also observed for the RTI477 strain, however the corresponding Dehydroxyfengycin MA, MB and MC compounds were not observed for the RTI477 strain (see Table IX).

It was further determined that the RTI301 strain produces an additional class of Fengycin and Dehydroxyfengycin that has not been previously identified. In this class, the L-isoleucine of Fengycin B and Dehydroxyfengycin B (position $X_3$ in FIG. 6) is replaced by L-homo-cysteine (Hcy). These previously unidentified Fengycin and Dehydroxyfengycin metabolites are referred to herein as Fengycin H and Dehydroxyfengycin H and are shown in FIG. 6 and Table IX. The newly identified Fengycin H compound was also observed for the RTI477 strain, however the corresponding Dehydroxyfengycin H compound was not observed for the RTI477 strain (Table IX).

It was further determined that the RTI301 strain produces an additional previously unidentified class of Fengycin and Dehydroxyfengycin metabolites. In this class, the amino acid at position 4 of the cyclic peptide backbone structure (position $X_1$ in FIG. 6) is replaced by L-isoleucine. These previously unidentified metabolites are referred to herein as Fengicin I and Dehydroxyfengicin I and are shown in FIG. 6 and in Table IX. Both the newly identified Fengycin I and Dehydroxyfengycin I compounds were also observed for the RTI477 strain (Table IX).

Thus, in the compositions and methods of the present invention, the *Bacillus* velezensis having antimicrobial properties can be a *Bacillus velezensis* RTI301 deposited as ATCC No. PTA-121165, or a mutant thereof having all the identifying characteristics thereof. Similarly, the *Bacillus subtilis* having beneficial properties for plant growth and/or health can be a *Bacillus subtilis* RTI477 deposited as ATCC No. PTA-121167, or a mutant thereof having all the identifying characteristics thereof. In the compositions and methods of the present invention, the plant can include soybean or corn and the plant growth benefit can be exhibited by increased yield.

In one embodiment, a composition is provided having two or more compatible microorganisms for benefiting plant growth and/or plant health, the composition comprising: at least one biologically pure culture of a first microorganism having antimicrobial properties and present in an amount suitable for inhibiting growth of endogenous microorganisms present in soil surrounding or living in association with a plant; and at least one biologically pure culture of a second microorganism having properties beneficial to the plant growth and/or plant health, wherein growth of the second microorganism is compatible with growth of the first microorganism, and wherein the second microorganism is present in an amount sufficient to become established and to benefit the plant growth and/or plant health, wherein application of the composition to seed of the plant, roots of the plant, or soil surrounding the plant benefits the plant growth and/or plant health. The properties of the second microorganism that are beneficial to the plant growth and/or plant health include one of increased plant yield, improved seedling vigor, improved root development, improved plant growth, improved plant health, improved appearance, improved resistance to plant pathogens, reduced pathogenic infection, or a combination thereof. The plant pathogen can include one or a combination of insects, nematodes, plant pathogenic fungi, or plant pathogenic bacteria.

In one embodiment a composition is provided for benefiting plant growth and/or plant health, the composition comprising: a biologically pure culture of *Bacillus velezensis* RTI301 deposited as ATCC No. PTA-121165, or a mutant thereof having all the identifying characteristics thereof; and a biologically pure culture of *Bacillus subtilis* RTI477 deposited as ATCC No. PTA-121167, or a mutant thereof having all the identifying characteristics thereof, present in an amount suitable to benefit the plant growth and/or plant health. Application of the composition to seed of the plant, roots of the plant, or soil surrounding the plant benefits plant growth and/or plant health.

As used herein, the phrase "a biologically pure culture of a bacterial strain" refers to one or a combination of: spores of the biologically pure fermentation culture of a bacterial strain vegetative cells of the biologically pure fermentation culture of a bacterial strain, one or more products of the biologically pure fermentation culture of a bacterial strain, a culture solid of the biologically pure fermentation culture of a bacterial strain, a culture supernatant of the biologically pure fermentation culture of a bacterial strain, an extract of the biologically pure fermentation culture of the bacterial strain, and one or more metabolites of the biologically pure fermentation culture of a bacterial strain.

In one embodiment, the compositions are in the form of a planting matrix. The planting matrix can be in the form of a potting soil.

In one embodiment, the compositions further include one or a combination of a carrier, a dispersant or a yeast extract.

In one embodiment, the compositions further comprise one or a combination of a microbial, a biological, or a chemical insecticide, fungicide, nematicide, bacteriocide, herbicide, plant extract, plant growth regulator, or fertilizer present in an amount suitable to benefit plant growth and/or to confer protection against a pathogenic infection in the plant.

In one embodiment, the composition for benefiting plant growth comprises: a biologically pure culture of *Bacillus velezensis* RTI301 deposited as ATCC No. PTA-121165, or a mutant thereof having all the identifying characteristics thereof; a biologically pure culture of *Bacillus subtilis* RTI477 deposited as ATCC No. PTA-121167, or a mutant thereof having all the identifying characteristics thereof; and a bifenthrin insecticide.

In one embodiment, the composition for benefiting plant growth comprises: a biologically pure culture of *Bacillus velezensis* RTI301 deposited as ATCC No. PTA-121165, or a mutant thereof having all the identifying characteristics thereof; a biologically pure culture of *Bacillus subtilis* RTI477 deposited as ATCC No. PTA-121167, or a mutant thereof having all the identifying characteristics thereof; and a bifenthrin insecticide, wherein the composition is in a formulation compatible with a liquid fertilizer. The formulation compatible with a liquid fertilizer can comprise a hydrated aluminum-magnesium silicate and at least one dispersant. The bifenthrin insecticide can be present at a concentration ranging from 0.1 g/ml to 0.2 g/ml. The bifenthrin insecticide can be present at a concentration of about 0.1715 g/ml. The term "in a formulation compatible with a liquid fertilizer" as used throughout the specification and claims is intended to mean that the formulation is capable of dissolution or dispersion or emulsion in an aqueous solution to allow for mixing with a fertilizer for delivery to plants in a liquid formulation.

In one embodiment a method is provided for benefiting plant growth and/or plant health, the method comprising delivering to seed of a plant, roots of a plant, or soil surrounding a plant a composition comprising: at least one biologically pure culture of a first microorganism having antimicrobial properties and present in an amount suitable for inhibiting growth of endogenous microorganisms present in soil surrounding or living in association with the plant; and at least one biologically pure culture of a second microorganism having properties beneficial to the plant growth and/or plant health, wherein growth of the second microorganism is compatible with growth of the first microorganism, and wherein the second microorganism is present in an amount suitable to become established and to benefit the plant growth and/or plant health, wherein delivery of the composition benefits the plant growth and/or plant health.

In one embodiment a method is provided for benefiting plant growth and/or plant health, the method comprising delivering to seed of a plant, roots of a plant, or soil surrounding a plant a composition comprising: a biologically pure culture of a *Bacillus velezensis* RTI301 deposited as ATCC No. PTA-121165, or a mutant thereof having all the identifying characteristics thereof; and a biologically pure culture of a *Bacillus subtilis* RTI477 deposited as ATCC No. PTA-121167, or a mutant thereof having all the identifying characteristics thereof, wherein delivery of the composition benefits the plant growth and/or plant health.

In one embodiment a method is provided for benefiting plant growth and/or plant health, the method comprising: delivering to seed of a plant, roots of a plant, or soil surrounding a plant a combination of: a first composition comprising a biologically pure culture of a *Bacillus velezensis* RTI301 deposited as ATCC No. PTA-121165, or a mutant thereof having all the identifying characteristics thereof; and a second composition comprising a biologically pure culture of a *Bacillus subtilis* RTI477 deposited as ATCC No. PTA-121167, or a mutant thereof having all the identifying characteristics thereof, wherein delivery of the combination benefits the plant growth and/or plant health.

The compositions comprising the microorganisms can be in the form of a liquid, an oil dispersion, a dust, a dry wettable powder, a spreadable granule, or a dry wettable granule. The microorganisms can be present in the form of spores or vegetative cells. The composition can be in the form of a liquid and each of the *Bacillus subtilis* RTI477 and the *Bacillus velezensis* RTI301 can be present at a concentration of from $1.0 \times 10^8$ CFU/ml to $1.0 \times 10^{12}$ CFU/ml. The composition can be in the form of a dust, a dry wettable powder, a spreadable granule, or a dry wettable granule and each of the the *Bacillus subtilis* RTI477 and the *Bacillus velezensis* RTI301 can be present in an amount of from $1.0 \times 10^8$ CFU/g to $1.0 \times 10^{12}$ CFU/g. The composition can be in the form of an oil dispersion and each of the the *Bacillus subtilis* RTI477 and the *Bacillus velezensis* RTI301 can be present at a concentration of from $1.0 \times 10^8$ CFU/ml to $1.0 \times 10^{12}$ CFU/ml.

The compositions comprising the microorganisms may further comprise one or a combination of a carrier, a dispersant or a yeast extract.

In one embodiment, a plant seed is provided that is coated with a composition having two or more compatible microorganisms for benefiting plant growth and/or plant health. The coating composition includes spores of at least one biologically pure culture of a first microorganism having antimicrobial properties and present in an amount suitable for inhibiting growth of endogenous microorganisms present in soil surrounding or living in association with a plant. The composition also includes spores of at least one biologically pure culture of a second microorganism having properties beneficial to plant growth and/or plant health, wherein growth of the second microorganism is compatible with growth of the first microorganism, and wherein the second microorganism is present in an amount sufficient to become established and to benefit the plant growth and/or plant health.

In one embodiment a plant seed is provided coated with a composition for benefiting plant growth and/or plant health, the composition comprising: spores of a biologically pure culture of *Bacillus velezensis* RTI301 deposited as ATCC No. PTA-121165, or a mutant thereof having all the identifying characteristics thereof; and spores of a biologically pure culture of *Bacillus subtilis* RTI477 deposited as ATCC No. PTA-121167, or a mutant thereof having all the identifying characteristics thereof, present in an amount suitable to benefit the plant growth and/or plant health.

In one embodiment, the *Bacillus subtilis* RTI477 and the *Bacillus velezensis* RTI301 are each present in an amount ranging from $1.0 \times 10^2$ CFU/seed to $1.0 \times 10^9$ CFU/seed.

In one embodiment, the plant seed further comprises one or a combination of a microbial, a biological, or a chemical insecticide, fungicide, nematicide, bacteriocide, herbicide, plant extract, plant growth regulator, or fertilizer present in an amount suitable to benefit plant growth and/or to confer protection against a pathogenic infection in the plant. In one embodiment, the insecticide comprises bifenthrin.

In one embodiment, a plant seed is provided, wherein the plant seed is coated with a composition for benefiting plant growth and/or plant health, the composition comprising: spores of a biologically pure culture of *Bacillus velezensis* RTI301 deposited as ATCC No. PTA-121165, or a mutant thereof having all the identifying characteristics thereof; spores of a biologically pure culture of *Bacillus subtilis* RTI477 deposited as ATCC No. PTA-121167, or a mutant thereof having all the identifying characteristics thereof; and a bifenthrin insecticide.

In one embodiment, a method is provided for benefiting plant growth and/or plant health, the method comprising planting a seed of a plant in a suitable growth medium, wherein the seed has been coated with a composition comprising spores of at least one biologically pure culture of a first microorganism having antimicrobial properties and present in an amount suitable for inhibiting growth of endogenous microorganisms present in soil surrounding or living in association with the plant; and spores of at least one biologically pure culture of a second microorganism having plant growth and/or plant health promoting properties, wherein growth of the second microorganism is compatible with growth of the first microorganism, and wherein the second microorganism is present in an amount suitable to become established and to benefit the plant growth and/or plant health.

In one embodiment, a method is provided for benefiting plant growth and/or plant health, the method comprising planting a seed of a plant in a suitable growth medium, wherein the seed has been coated with a composition comprising: spores of a biologically pure culture of *Bacillus* velezensis RTI301 deposited as ATCC No. PTA-121165, or a mutant thereof having all the identifying characteristics thereof; and spores of a biologically pure culture of *Bacillus subtilis* RTI477 deposited as ATCC No. PTA-121167, or a mutant thereof having all the identifying characteristics thereof, wherein the coating comprising the spores of the RTI301 and the RTI477 benefits the plant growth and/or plant health.

The coated seed of the present invention can be a seed from a wide variety of plants including, for example, comprises the seed of monocots, dicots, Cereals, Corn, Sweet Corn, Popcorn, Seed Corn, Silage Corn, Field Corn, Rice, Wheat, Barley, Sorghum, Brassica Vegetables, Broccoli, Cabbage, Cauliflower, Brussels Sprouts, Collards, Kale, Mustard Greens, Kohlrabi, Bulb Vegetables, Onion, Garlic, Shallots, Fruiting Vegetables, Pepper, Tomato, Ground Cherry, Tomatillo, Okra, Grape, Herbs/Spices, Cucurbit Vegetables, Cucumber, Cantaloupe, Melon, Muskmelon, Squash, Watermelon, Pumpkin, Eggplant, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Cotton, Flax, Peanut, Rapeseed, Safflower, Sesame, Sunflower, Soybean, Root/Tuber and Corn Vegetables, Carrot, Potato, Sweet Potato, Beets, Ginger, Horseradish, Radish, Ginseng, Turnip, sugarcane, sugarbeet, Grass, and Turf grass.

The coated plant seed can be corn or soybean and the plant growth benefit can be exhibited by increased yield.

For the coated plant seed, the properties of the second microorganism beneficial to plant growth and/or plant health include one or more of increased yield, improved seedling vigor, improved root development, improved plant growth, improved plant health, improved appearance, improved resistance to plant pathogens, or reduced pathogenic infection, or a combination thereof. The plant pathogen can include one or a combination of insects, nematodes, plant pathogenic fungi, or plant pathogenic bacteria.

The first and second microorganisms of the composition coating the plant seed can be *Bacillus* spp. microorganisms. The growth of the second microorganism can be faster than that of the first microorganism and the second microorganism can be characterized by a swarming and high motility phenotype. The second microorganism can be a *Bacillus subtilis*. The first microorganism can be a *Bacillus velezensis* and the second microorganism can be a *Bacillus subtilis*. The *Bacillus velezensis* can be a *Bacillus velezensis* RTI301 deposited as ATCC No. PTA-121165, or a mutant thereof having all the identifying characteristics thereof. The *Bacillus subtilis* can be a *Bacillus subtilis* RTI477 deposited as ATCC No. PTA-121167, or a mutant thereof having all the identifying characteristics thereof. The composition coated onto the plant seed can include an amount of spores of each of the first microorganism and the second microorganism from $1.0 \times 10^2$ CFU/seed to $1.0 \times 10^9$ CFU/seed.

In one embodiment a method is provided for benefiting plant growth and/or plant health, the method comprising planting a seed of a plant in a suitable growth medium, wherein the seed has been coated with a composition comprising: spores of a biologically pure culture of *Bacillus velezensis* RTI301 deposited as ATCC No. PTA-121165, or a mutant thereof having all the identifying characteristics thereof; and spores of a biologically pure culture of *Bacillus subtilis* RTI477 deposited as ATCC No. PTA-121167, or a mutant thereof having all the identifying characteristics thereof, present in an amount suitable to benefit the plant growth and/or plant health.

In one embodiment a composition is provided for benefiting plant growth and/or plant health, the composition comprising: one or more chemical active agents having one or both of antibacterial or antifungal properties and present in an amount suitable for inhibiting growth of endogenous microorganisms present in soil surrounding or living in association with a plant; and at least one biologically pure culture of a microorganism having properties beneficial to the plant growth and/or plant health. Growth of the microorganism is compatible with the chemical active agent, and the microorganism is present in an amount suitable to become established and to benefit the plant growth and/or plant health. Application of the composition to seed of the plant, roots of the plant, or soil surrounding the plant benefits the plant growth and/or plant health.

In one embodiment, a method is provided for benefiting plant growth and/or plant health, the method comprising delivering to seed of a plant, roots of a plant, or soil surrounding a plant a combination of: one or more chemical active agents having one or both of antibacterial or antifungal properties present in an amount suitable for inhibiting growth of endogenous microorganisms present in soil surrounding or living in association with the plant; and a composition comprising at least one biologically pure culture of a microorganism having properties beneficial to the plant growth and/or plant health. Growth of the microorganism is compatible with the chemical active agent or, in the case of incompatibility, the microorganism is delivered subsequent to delivery of the chemical active agent. The microorganism is present in an amount suitable to become established and to benefit the plant growth and/or plant health, such that delivery of the combination of the chemical active agent and the microorganism benefits the plant growth and/or plant health. In the case where the one or more chemical active agents and the microorganism are compatible, the one or more chemical active agents can be formulated together with the composition that includes the microorganism. Delivery of the combination of the chemical active agent and the microorganism to seed of the plant, roots of the plant, or soil surrounding the plant benefits plant growth and/or plant health.

For the composition and method including one or more chemical active agents, the properties of the microorganism beneficial to plant growth and/or plant health can include increased yield, improved seedling vigor, improved root development, improved plant growth, improved plant health, improved appearance, improved resistance to plant pathogens, reduced pathogenic infection, or a combination thereof. The plant pathogens can include one or a combination of insects, nematodes, plant pathogenic fungi, or plant pathogenic bacteria.

The one or more chemical active agents for creating the niche can include, for example, but are not limited to strobilurine, a triazole, flutriafol, tebuconazole, prothiaconazole, expoxyconazole, fluopyram, chlorothalonil, thiophanate-methyl, a copper-based fungicide, copper hydroxide fungicide, an EDBC-based fungicide, mancozeb, a succinase dehydrogenase (SDHI) fungicide, bixafen, iprodione, dimethomorph, or valifenalate. In another example, the one or more chemical active agents can include a fumigant such as, for example, chloropicrin, Dazomet, 1,3-dichloropropene (Telone), dimethyl disulfide, metam sodium/potassium, methyl bromide.

The composition can be in the form of a liquid, an oil dispersion, a dust, a dry wettable powder, a spreadable granule, or a dry wettable granule. The beneficial microorganism can be present in the form of spores or vegetative cells. The beneficial microorganism can be a *Bacillus* spp. The beneficial microorganism can be a *Bacillus subtilis*. The microorganism can be a *Bacillus subtilis* characterized by a swarming and high motility phenotype. The microorganism can be a *Bacillus subtilis* RTI477 deposited as ATCC No. PTA-121167, or a mutant thereof having all the identifying characteristics thereof. The composition can be in the form of a liquid and the beneficial microorganism can be *Bacillus subtilis* RTI477 present at a concentration of from $1.0 \times 10^8$ CFU/ml to $1.0 \times 10^{12}$ CFU/ml. The composition can be in the form of a dust, a dry wettable powder, a spreadable granule, or a dry wettable granule and the *Bacillus subtilis* RTI477 can be present in an amount of from $1.0 \times 10^8$ CFU/g to $1.0 \times 10^{12}$ CFU/g. The composition can be in the form of an oil dispersion and the *Bacillus subtilis* RTI477 can be present at a concentration of from $1.0 \times 10^8$ CFU/ml to $1.0 \times 10^{12}$ CFU/ml.

In the compositions and methods having two or more compatible microorganisms of the present invention for benefiting plant growth and/or plant health, the compositions can further include one or a combination of a microbial, a biological, or a chemical insecticide, fungicide, nematicide, bacteriocide, herbicide, plant extract, plant growth regulator, or fertilizer present in an amount suitable to benefit plant growth and/or to confer protection against a pathogenic infection in the plant.

In one embodiment, the fungicide can include an extract from *Lupinus albus* doce. In one embodiment, the fungicide can include a BLAD polypeptide. The BLAD polypeptide can be a fragment of the naturally occurring seed storage protein from sweet lupine (*Lupinus albus* doce) that acts on susceptible fungal pathogens by causing damage to the fungal cell wall and disrupting the inner cell membrane. The compositions can include about 20% of the BLAD polypeptide.

In one embodiment, the insecticide can comprise bifenthrin. The nematicide can comprise cadusafos. The composition can be formulated as a liquid, a powder, a wettable dissolvable granule, or as spreadable granules. The insecticide can comprise bifenthrin and clothianidin. The insecticide can comprise bifenthrin and clothianidin and the composition can be formulated for compatibility with a liquid fertilizer. The insecticide can comprise bifenthrin or zeta-cypermethrin.

The nematicide can comprise cadusafos. The insecticide can comprise bifenthrin and clothianidin. The composition can be formulated as a liquid and the insecticide can comprise bifenthrin or zeta-cypermethrin.

In one embodiment, the method can further include applying a liquid fertilizer to: soil or growth medium surrounding the plant; soil or growth medium before sowing seed of the plant in the soil or growth medium; or soil or growth medium before planting the plant in the soil or growth medium.

In an embodiment, the bifenthrin composition can comprise: bifenthrin; a hydrated aluminum-magnesium silicate; and at least one dispersant selected from a sucrose ester, a lignosulfonate, an alkylpolyglycoside, a naphthalenesulfonic acid formaldehyde condensate and a phosphate ester.

The bifenthrin can be preferably present in a concentration of from 1.0% by weight to 35% by weight, more particularly, from 15% by weight to 25% by weight based upon the total weight of all components in the composition.

The bifenthrin insecticide composition can be present in the liquid formulation at a concentration ranging from 0.1 g/ml to 0.2 g/ml. The bifenthrin insecticide may be present in the liquid formulation at a concentration of about 0.1715 g/ml.

The dispersant or dispersants can preferably be present in a total concentration of from 0.02% by weight to 20% by weight based upon the total weight of all components in the composition.

In some embodiments, the hydrated aluminum-magnesium silicate may be selected from the group consisting of montmorillonite and attapulgite.

In some embodiments, the phosphate ester may be selected from a nonyl phenol phosphate ester and a tridecyl alcohol ethoxylated phosphate potassium salt.

Other embodiments may further include at least one of an anti-freeze agent, an anti-foam agent and a biocide.

In one embodiment a composition is provided for benefiting plant growth, the composition comprising: a biologically pure culture of *Bacillus velezensis* RTI301 deposited as ATCC No. PTA-121165, or a mutant thereof having all the identifying characteristics thereof; a biologically pure culture of *Bacillus subtilis* RTI477 deposited as ATCC No. PTA-121167, or a mutant thereof having all the identifying characteristics thereof; and an insecticide, wherein the composition is in a formulation compatible with a liquid fertilizer. The insecticide can be one or a combination of pyrethroids, bifenthrin, tefluthrin, zeta-cypermethrin, organophosphates, chlorethoxyfos, chlorpyrifos, tebupirimfos, cyfluthrin, fiproles, fipronil, nicotinoids, or clothianidin. The insecticide can include bifenthrin. The composition can include a bifenthrin insecticide and a hydrated aluminum-magnesium silicate and at least one dispersant. The bifenthrin insecticide can be present at a concentration ranging from 0.1 g/ml to 0.2 g/ml. The bifenthrin insecticide can be present at a concentration of about 0.1715 g/ml.

In addition, suitable insecticides, herbicides, fungicides, and nematicides of the compositions and methods of the present invention can include the following:

Insecticides: A0) various insecticides, including agrigata, al-phosphide, amblyseius, aphelinus, *aphidius*, aphidoletes, artimisinin, *autographa californica* NPV, azocyclotin, *Bacillus subtilis, Bacillus thuringiensis* spp. *aizawai, Bacillus thuringiensis* spp. *kurstaki, Bacillus thuringiensis, Beauveria, Beauveria bassiana*, betacyfluthrin, biologicals, bisultap, brofluthrinate, bromophos-e, bromopropylate, Bt-Corn-G M, Bt-Soya-G M, capsaicin, cartap, celastrus-extract, chlorantraniliprole, chlorbenzuron, chlorethoxyfos, chlorfluazuron, chlorpyrifos-e, cnidiadin, cryolite, cyanophos, cyantraniliprole, cyhalothrin, cyhexatin, cypermethrin, dacnusa, DCIP, dichloropropene, dicofol, diglyphus, diglyphus+dacnusa, dimethacarb, dithioether, dodecyl-acetate, emamectin, encarsia, EPN, eretmocerus, ethylene-dibromide, eucalyptol, fatty-acids, fatty-acids/salts, fenazaquin, fenobucarb (BPMC), fenpyroximate, flubrocythrinate, flufenzine, formetanate, formothion, furathiocarb, gamma-cyhalothrin, garlic-juice, granulosis-virus, harmonia, heliothis armigera NPV, inactive bacterium, indol-3-ylbutyric acid, iodomethane, iron, isocarbofos, isofenphos, isofenphos-m, isoprocarb, isothioate, kaolin, lindane, liuyangmycin, matrine, mephosfolan, metaldehyde, metarhizium-anisopliae, methamidophos, metolcarb (MTMC), mineral-oil, mirex, m-isothiocyanate, monosultap, myrothecium verrucaria, naled, neochrysocharis formosa, nicotine, nicotinoids, oil, oleic-acid, omethoate, orius, oxymatrine, paecilomyces, paraffin-oil, parathion-e, pasteuria, petroleum-oil, pheromones, phosphorus-acid, photorhabdus, phoxim, phytoseiulus, pirimiphos-e, plant-oil, plutella xylostella GV, polyhedrosis-virus, polyphenol-extracts, potassium-oleate, profenofos, prosuler, prothiofos, pyraclofos, pyrethrins, pyridaphenthion, pyrimidifen, pyriproxifen, quillay-extract, quinomethionate, rape-oil, rotenone, saponin, saponozit, sodium-compounds, sodium-fluosilicate, starch, steinernema, streptomyces, sulfluramid, sulphur, tebupirimfos, tefluthrin, temephos, tetradifon, thiofanox, thiometon, transgenics (e.g., Cry3Bb1), triazamate, trichoderma, trichogramma, triflumuron, *verticillium*, vertrine, isomeric insecticides (e.g., kappa-bifenthrin, kappa-tefluthrin), dichoromezotiaz, broflanilide, pyraziflumid; A1) the class of carbamates, including aldicarb, alanycarb, benfuracarb, carbaryl, carbofuran, carbosulfan, methiocarb, methomyl, oxamyl, pirimicarb, propoxur and thiodicarb; A2) the class of organophosphates, including acephate, azinphos-ethyl, azinphos-methyl, chlorfenvinphos, chlorpyrifos, chlorpyrifos-methyl, demeton-S-methyl, diazinon, dichlorvos/DDVP, dicrotophos, dimethoate, disulfoton, ethion, fenitrothion, fenthion, isoxathion, malathion, methamidaphos, methidathion, mevinphos, monocrotophos, oxymethoate, oxydemeton-methyl, parathion, parathion-methyl, phenthoate, phorate, phosalone, phosmet, phosphamidon, pirimiphos-methyl, quinalphos, terbufos, tetrachlorvinphos, triazophos and trichlorfon; A3) the class of cyclodiene organochlorine compounds such as endosulfan; A4) the class of fiproles, including ethiprole, fipronil, pyrafluprole and pyriprole; A5) the class of neonicotinoids, including acetamiprid, clothianidin, dinotefuran, imidacloprid, nitenpyram, thiacloprid and thiamethoxam; A6) the class of spinosyns such as spinosad and spinetoram; A7) chloride channel activators from the class of mectins, including abamectin, emamectin benzoate, ivermectin, lepimectin and milbemectin; A8) juvenile hormone mimics such as hydroprene, kinoprene, methoprene, fenoxycarb and pyriproxyfen; A9) selective homopteran feeding blockers such as pymetrozine, flonicamid and pyrifluquinazon; A10) mite growth inhibitors such as clofentezine, hexythiazox and etoxazole; A11) inhibitors of mitochondrial ATP synthase such as diafenthiuron, fenbutatin oxide and propargite; uncouplers of oxidative phosphorylation such as chlorfenapyr; A12) nicotinic acetylcholine receptor channel blockers such as bensultap, cartap hydrochloride, thiocyclam and thiosultap sodium; A13) inhibitors of the chitin biosynthesis type 0 from the benzoylurea class, including bistrifluron, diflubenzuron, flufenoxuron, hexaflumuron, lufenuron, novaluron and teflubenzuron; A14) inhibitors of the chitin biosynthesis type 1 such as buprofezin; A15) moulting disruptors such as cyromazine; A16) ecdyson receptor agonists such as methoxyfenozide, tebufenozide, halofenozide and chromafenozide; A17) octopamin receptor agonists such as amitraz; A18) mitochondrial complex electron transport inhibitors pyridaben, tebufenpyrad, tolfenpyrad, flufenerim, cyenopyrafen, cyflumetofen, hydramethylnon, acequinocyl or fluacrypyrim; A19) voltage-dependent sodium channel blockers such as indoxacarb and metaflumizone; A20) inhibitors of the lipid synthesis such as spirodiclofen, spiromesifen and spirotetramat; A21) ryanodine receptor-modulators from the class of diamides, including flubendiamide, the phthalamide compounds (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, chloranthraniliprole and cyanthraniliprole; A22) compounds of unknown or uncertain mode of action such as azadirachtin, amidoflumet, bifenazate, fluensulfone, piperonyl butoxide, pyridalyl, sulfoxaflor; or A23) sodium channel modulators from the class of pyrethroids, including acrinathrin, allethrin, bifenthrin, cyfluthrin, lambda-cyhalothrin, cypermethrin, alpha-cypermethrin, beta-cypermethrin, zeta-cypermethrin, delta methrin, esfenvalerate, etofenprox, fenpropathrin, fenvalerate, flucythrinate, tau-fluvalinate, permethrin, silafluofen and tralomethrin.

Fungicides: B0) benzovindiflupyr, anitiperonosporic, ametoctradin, amisulbrom, copper salts (e.g., copper hydroxide, copper oxychloride, copper sulfate, copper persulfate), boscalid, thiflumazide, flutianil, furalaxyl, thiabendazole, benodanil, mepronil, isofetamid, fenfuram, bixafen, fluxapyroxad, penflufen, sedaxane, coumoxystrobin, enoxastrobin, flufenoxystrobin, pyraoxystrobin, pyrametostrobin, triclopyricarb, fenaminstrobin, metominostrobin, pyribencarb, meptyldinocap, fentin acetate, fentin chloride, fentin hydroxide, oxytetracycline, chlozolinate, chloroneb, tecnazene, etridiazole, iodocarb, prothiocarb, *Bacillus subtilis* syn., *Bacillus amyloliquefaciens* (e.g., strains QST 713, FZB24, MBI600, D747), extract from *Melaleuca alternifolia*, pyrisoxazole, oxpoconazole, etaconazole, fenpyrazamine, naftifine, terbinafine, validamycin, pyrimorph, valifenalate, fthalide, probenazole, isotianil, laminarin, estract from *Reynoutria sachalinensis*, phosphorous acid and salts, teclofthalam, triazoxide, pyriofenone, organic oils, potassium bicarbonate, chlorothalonil, fluoroimide; B1) azoles, including bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole, azaconazole, diniconazole-M, oxpoconazol, paclobutrazol, uniconazol, 1-(4-chloro-phenyl)-2-([1,2,4]triazol-1-yl)-cycloheptanol and imazalilsulfphate; B2) strobilurins, including azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxy-imino-N-methyl-acetamide and 3-methoxy-2-(2-(N-(4-methoxy-phenyl)-cyclopropanecarboximidoylsulfanylmethyl)-phenyl)-acrylic acid methyl ester; B3) carboxamides, including carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxyphenyl)ethyl)-2-methanesulfonyl-a mino-3-methylbutyra mide, N-(2-(4-[3-(4-chloro-phenyl)prop-2-ynyloxy]-3-methoxy-phenyl)ethyl)-2-ethanesulfonylamino-3-methylbutyramide, methyl 3-(4-chlorophenyl)-3-(2-isopropoxycarbonyl-amino-3-methyl-butyrylamino) propionate, N-(4'-bromobiphenyl-2-yl)-4-difluoromethy^-methylthiazole-δ-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4- difluoromethyl-2-methyl-thiazole-5-carboxamide, N-(3\4'-dichloro-4-fluorobiphenyl-2-yl)-3-difluoro-methyl-1-methyl-pyrazole-4-carboxamide, N-(3',4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methyl-thiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluoro-biphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofam, N-(6-methoxy-pyridin-3-yl) cyclopropanecarboxamide, 2-iodo-N-phenyl-benzamide, N-(2-bicyclo-propyl-2-yl-phenyl)-3-difluormethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-ylcarboxamide, N-(3',4',5'-trifluorobiphenyl-2-yl)-5-chloro-1,3-dimethyl-pyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3', 4', 5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-5-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-S-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-S-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-S-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-S-difluoromethyl-1H-pyrazole-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[4'-(trifluoromethylthio)-biphenyl-2-yl]-3-difluoromethyl-1-methyl-1H-pyrazole-4-carboxamide and N-[4'-(trifluoromethylthio)-biphenyl-2-yl]-1-methyl-3-trifluoromethyl-1-methyl-1H-pyrazole-4-carboxamide; B4) heterocyclic compounds, including fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methyl-piperidin-1-yl)-6-(2,4,6-trifluorophenyl)-[1,2,4]triazolo[1,5-a]pyrimidine, anilazine, diclomezine, pyroquilon, proquinazid, tricyclazole, 2-butoxy-6-iodo-3-propyl-chromen-4-one, acibenzolar-S-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl-[1,2,4]triazolo[1,5-a]pyrimidin-2,7-diamine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro pyridin-2-yl)-methyl)-2,4-dichloro-nicotinamide, diflumetorim, nitrapyrin, dodemorphacetate, fluoroimid, blasticidin-S, chinomethionat, debacarb, difenzoquat, difenzoquat-methylsulphat, oxolinic acid and piperalin; B5) carbamates, including mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)-ethanesulfonyl)but-2-yl)carbamate, methyl 3-(4-chloro-phenyl)-3-(2-isopropoxycarbonylamino-3-methyl-butyrylamino)propanoate; or B6) other fungicides, including guanidine, dodine, dodine free base, iminoctadine, guazatine, antibiotics: kasugamycin, oxytetracyclin and its salts, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts, organophosphorus compounds: edifenphos, iprobenfos, fosetyl, fosetyl-aluminum, phosphorous acid and its salts, pyrazophos, tolclofos-methyl, organochlorine compounds: dichlofluanid, flusulfamide, hexachlorobenzene, phthalide, pencycuron, quintozene, thiophanate, thiophanate-methyl, tolylfluanid, others: cyflufenamid, cymoxanil, dimethirimol, ethirimol, furalaxyl, metrafenone and spiroxamine, guazatine-acetate, iminoc-tadine-triacetate, iminoctadine-tris(albesilate), kasugamycin hydrochloride hydrate, dichlorophen, pentachlorophenol and its salts, N-(4-chloro-2-nitro-phenyl)-N-ethyl-4-methyl-benzenesulfonamide, dicloran, nitrothal-isopropyl, tecnazen, biphenyl, bronopol, diphenylamine, mildiomycin, oxincopper, prohexadione calcium, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethylsilanyl-propoxy)-phenyl)-N-ethyl-N-methylformamidine and N'-(5-difluormethyl-2-methyl-4-(3-trimethylsilanyl-propoxy)-phenyl)-N-ethyl-N-methyl formamidine.

Herbicides: C1) acetyl-CoA carboxylase inhibitors (ACC), for example cyclohexenone oxime ethers, such as alloxydim, clethodim, cloproxydim, cycloxydim, sethoxydim, tralkoxydim, butroxydim, clefoxydim or tepraloxydim; phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl; C2 acetolactate synthase inhibitors (ALS), for example imidazolinones, such as imazapyr, imazaquin, imazamethabenz-methyl (imazame), imazamox, imazapic or imazethapyr; pyrimidyl ethers, such as pyrithiobac-acid, pyrithiobac-sodium, bispyribac-sodium. KIH-6127 or pyribenzoxym; sulfonamides, such as florasulam, flumetsulam or metosulam; or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron; C3) amides, for example allidochlor (CDAA), benzoylpropethyl, bromobutide, chiorthiamid. diphenamid, etobenzanidbenzchlomet), fluthiamide, fosamin or monalide; C4) auxin herbicides, for example pyridinecarboxylic acids, such as clopyralid or picloram; or 2,4-D or benazolin; C5) auxin transport inhibitors, for example naptalame or diflufenzopyr; C6) carotenoid biosynthesis inhibitors, for example benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol; C7) enolpyruvylshikimate-3-phosphate synthase inhibitors (EPSPS), for example glyphosate or sulfosate; C8) glutamine synthetase inhibitors, for example bilanafos (bialaphos) or glufosinate-ammonium; C9) lipid biosynthesis inhibitors, for example anilides, such as anilofos or mefenacet; chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor; thioureas, such as butylate, cycloate, di-allate, dimepiperate, EPIC. esprocarb, molinate, pebulate, prosulfocarb, thiobencarb (benthiocarb), tri-allate or vemolate; or benfuresate or perfluidone; C10) mitosis inhibitors, for example carbamates, such as asulam, carbetamid, chlorpropham, orbencarb, pronamid (propyzamid), propham or tiocarbazil; dinitroanilines, such as benefin, butralin, dinitramin, ethalfluralin, fluchloralin, oryzalin, pendimethalin, prodiamine or trifluralin; pyridines, such as dithiopyr or thiazopyr; or butamifos, chlorthal-dimethyl (DCPA) or maleic hydrazide; C11) protoporphyrinogen IX oxidase inhibitors, for example diphenyl ethers, such as acifluorfen, acifluorfen-sodium, aclonifen, bifenox, chlomitrofen (CNP), ethoxyfen, fluorodifen, fluoroglycofenethyl, fomesafen, furyloxyfen, lactofen, nitrofen, nitrofluorfen or oxyfluorfen; oxadiazoles, such as oxadiargyl or oxadiazon; cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or pyrazoles, such as ET-751.JV 485 or nipyraclofen; C12) photosynthesis inhibitors, for example propanil, pyridate or pyridafol; benzothiadiazinones, such as bentazone; dinitrophenols, for example bromofenoxim, dinoseb, dinoseb-acetate, dinoterb or DNOC; dipyridylenes, such as cyperquat-chloride, difenzoquat-methylsulfate, diquat or paraquat-dichloride; ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron; phenols, such as bromoxynil or ioxynil; chloridazon; triazines, such as ametryn, atrazine, cyanazine, desmein, dimethamethryn, hexazinone, prometon, prometryn, propazine, simazine, simetryn, terbumeton, terbutryn, terbutylazine or trietazine; triazinones, such as metamitron or metribuzin; uracils, such as bromacil, lenacil or terbacil; or biscarbamates, such as desmedipham or phenmedipham; C13) synergists, for example oxiranes, such as tridiphane; C14) CIS cell wall synthesis inhibitors, for example isoxaben or dichlobenil; C15) various other herbicides, for example dichloropropionic acids, such as dalapon; dihydrobenzofurans, such as ethofumesate; phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon; or their environmentally compatible salts.

Nematicides or bionematicides: Benomyl, cloethocarb, aldoxycarb, tirpate, diamidafos, fenamiphos, cadusafos, dichlofenthion, ethoprophos, fensulfothion, fosthiazate, heterophos, isamidofof, isazofos, phosphocarb, thionazin, imicyafos, mecarphon, acetoprole, benclothiaz, chloropicrin, dazomet, fluensulfone, 1,3-dichloropropene (telone), dimethyl disulfide, metam sodium, metam potassium, metam salt (all MITC generators), methyl bromide, biological soil amendments (e.g., mustard seeds, mustard seed extracts), steam fumigation of soil, allyl isothiocyanate (AITC), dimethyl sulfate, furfual (aldehyde).

Suitable plant growth regulators of the present invention include the following: Plant Growth Regulators: D1) Anti-auxins, such as clofibric acid, 2,3,5-tri-iodobenzoic acid; D2) Auxins such as 4-CPA, 2,4-D, 2,4-DB, 2,4-DEP, dichlorprop, fenoprop, IAA, IBA, naphthaleneacetamide, α-naphthaleneacetic acids, 1-naphthol, naphthoxyacetic acids, potassium naphthenate, sodium naphthenate, 2,4,5-T; D3) cytokinins, such as 2iP, benzyladenine, 4-hydroxyphenethyl alcohol, kinetin, zeatin; D4) defoliants, such as calcium cyanamide, dimethipin, endothal, ethephon, merphos, metoxuron, pentachlorophenol, thidiazuron, tribufos; D5) ethylene inhibitors, such as aviglycine, 1-methylcyclopropene; D6) ethylene releasers, such as ACC, etacelasil, ethephon, glyoxime; D7) gametocides, such as fenridazon, maleic hydrazide; D8) gibberellins, such as gibberellins, gibberellic acid; D9) growth inhibitors, such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, tiaojiean, 2,3,5-tri-iodobenzoic acid; D10) morphactins, such as chlorfluren, chlorflurenol, dichlorflurenol, flurenol; D11) growth retardants, such as chlormequat, daminozide, flurprimidol, mefluidide, paclobutrazol, tetcyclacis, uniconazole; D12) growth stimulators, such as brassinolide, brassinolide-ethyl, DCPTA, forchlorfenuron, hymexazol, prosuler, triacontanol; D13) unclassified plant growth regulators, such as bachmedesh, benzofluor, buminafos, carvone, choline chloride, ciobutide, clofencet, cyanamide, cyclanilide, cycloheximide, cyprosulfamide, epocholeone, ethychlozate, ethylene, fuphenthiourea, furalane, heptopargil, holosulf, inabenfide, karetazan, lead arsenate, methasulfocarb, prohexadione, pydanon, sintofen, triapenthenol, trinexapac.

The fertilizer can be a liquid fertilizer. The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients, commonly known as starter fertilizers that are high in phosphorus and promote rapid and vigorous root growth.

Chemical formulations of the present invention can be in any appropriate conventional form, for example an emulsion concentrate (EC), a suspension concentrate (SC), a suspoemulsion (SE), a capsule suspension (CS), a water dispersible granule (WG), an emulsifiable granule (EG), a water in oil emulsion (EO), an oil in water emulsion (EW), a microemulsion (ME), an oil dispersion (OD), an oil miscible flowable (OF), an oil miscible liquid (OL), a soluble concentrate (SL), an ultra-low volume suspension (SU), an ultra-low volume liquid (UL), a dispersible concentrate (DC), a wettable powder (WP) or any technically feasible formulation in combination with agriculturally acceptable adjuvants.

In one embodiment, a product is provided comprising: a first composition comprising a biologically pure culture of *Bacillus velezensis* RTI301 deposited as ATCC No. PTA-121165, or a mutant thereof having all the identifying characteristics thereof and a biologically pure culture of *Bacillus subtilis* RTI477 deposited as ATCC No. PTA-121167, or a mutant thereof having all the identifying characteristics thereof; a second composition comprising one or a combination of a microbial, a biological, or a chemical insecticide, fungicide, nematicide, bacteriocide, herbicide, plant extract, plant growth regulator, or fertilizer, wherein the first and second composition are separately packaged; and, optionally, instructions for delivering in an amount suitable to benefit plant growth, a combination of the first and second compositions to: foliage of the plant, bark of the plant, fruit of the plant, flowers of the plant, seed of the plant, roots of the plant, a cutting of the plant, a graft of the plant, callus tissue of the plant; soil or growth medium surrounding the plant; soil or growth medium before sowing seed of the plant in the soil or growth medium; or soil or growth medium before planting the plant, the plant cutting, the plant graft, or the plant callus tissue in the soil or growth medium.

In one embodiment, the first composition further comprises one or a combination of a carrier, a dispersant, or a yeast extract.

In one embodiment, the first composition is in the form of a liquid, a dust, a spreadable granule, a dry wettable powder, or a dry wettable granule. In one embodiment, the first composition is in the form of a liquid and each of the *Bacillus velezensis* RTI301 and the *Bacillus subtilis* RTI477 is present at a concentration of from $1.0\times10^8$ CFU/ml to $1.0\times10^{12}$ CFU/ml. In one embodiment, the first composition is in the form of a dust, a dry wettable powder, a spreadable granule, or a dry wettable granule and each of the *Bacillus velezensis* RTI301 and the *Bacillus subtilis* RTI477 is present in an amount of from $1.0\times10^8$ CFU/g to $1.0\times10^{12}$ CFU/g. In one embodiment, the first composition is in the form of an oil dispersion and each of the *Bacillus velezensis* RTI301 and the *Bacillus subtilis* RTI477 is present at a concentration of from $1.0\times10^8$ CFU/ml to $1.0\times10^{12}$ CFU/ml.

In the product, the insecticide can be one or a combination of pyrethroids, bifenthrin, tefluthrin, zeta-cypermethrin, organophosphates, chlorethoxyphos, chlorpyrifos, tebupirimphos, cyfluthrin, fiproles, fipronil, nicotinoids, or clothianidin. In one embodiment, the insecticide in the second composition of the product comprises bifenthrin. In one embodiment, the insecticide in the second composition of the product comprises bifenthrin and it is in a formulation compatible with a liquid fertilizer.

EXAMPLES

The following EXAMPLEs have been included to provide guidance to one of ordinary skill in the art for practicing representative embodiments of the presently disclosed subject matter. In light of the present invention and the general level of skill in the art, those of skill can appreciate that the following EXAMPLEs are intended to be exemplary only and that numerous changes, modifications, and alterations can be employed without departing from the scope of the presently disclosed subject matter.

Example 1

Identification of a Bacterial Isolate as a *Bacillus Subtilis* Through Sequence Analysis A plant associated bacterial strain, designated herein as RTI477, was isolated from the root of Moringa oleifera grown in North Carolina. The 16S rRNA and the rpoB genes of the RTI477 strain were sequenced and subsequently compared to other known bacterial strains in the NCBI and RDP databases using BLAST. It was determined that the 16S RNA partial sequence of RTI477 (SEQ ID NO: 1) is identical to the partial 16S rRNA gene sequence of *Bacillus subtilis* strain BSn5 (CP002468), *Bacillus amyloliquefaciens* strain NS6 (KF177175), and *Bacillus subtilis* subsp. *subtilis* strain DSM 10 (NR_027552). In addition, it was determined that the rpoB sequence of RTI477 has 99% sequence identity to known strains *Bacillus subtilis* PY79 (CP006881), *Bacillus subtilis* subsp. *subtilis* 6051-HGW (CP003329) (i.e., 99% sequence identity; 9 bp difference), and *Bacillus subtilis* subsp. *subtilis* BAB-la (CP004405) (i.e., 99% sequence identity; 10 bp difference). The RTI477 strain was identified as a strain of *Bacillus subtilis*. The differences in sequence for the rpoB gene at the DNA level indicate that RTI477 is a new strain of *Bacillus subtilis*. The strain of *Bacillus subtilis* RTI477 was deposited on 17 Apr. 2014 under the terms of the Budapest Treaty on the International Recognition of the Deposit of Microorganisms for the Purposes of Patent Procedure at the American Type Culture Collection (ATCC) in Manassas, Va., USA and bears the Patent Accession No. PTA-121167.

Example 2

Identification of a Bacterial Isolate as a *Bacillus velezensis* Through Sequence Analysis A plant associated bacterial strain, designated herein as RTI301, was isolated from the rhizosphere soil of grape vines growing at a vineyard in NY. The 16S rRNA and the rpoB genes of the RTI301 strain were sequenced and subsequently compared to other known bacterial strains in the NCBI and RDP databases using BLAST. It was determined that the 16S RNA partial sequence of RTI301 (SEQ ID NO: 3) is identical to the 16S rRNA gene sequence of *Bacillus amyloliquefaciens* strain NS6 (KF177175), *Bacillus amyloliquefaciens* strain FZB42 (NR_075005), and *Bacillus subtilis* subsp. *subtilis* strain DSM 10 (NR_027552). It was also determined that the rpoB gene sequence of RTI301 (SEQ ID NO: 4) has sequence similarity to the same gene in *Bacillus amyloliquefaciens* subsp. *plantarum* TrigoCor1448 (CP007244) (99% sequence identity; 3 base pair difference); *Bacillus amyloliquefaciens* subsp. *plantarum* AS43.3 (CP003838) (99% sequence identity; 7 base pair difference); *Bacillus amyloliquefaciens* CC178 (CP006845) (99% sequence identity; 8 base pair difference), and *Bacillus amyloliquefaciens* FZB42 (CP000560) (99% sequence identity; 8 base pair difference). The RTI301 strain was identified as a *Bacillus amyloliquefaciens*. The differences in sequence for the rpoB gene at the DNA level indicate that RTI301 is a new strain of *Bacillus amyloliquefaciens*. The strain of *Bacillus amyloliquefaciens* RTI301 was deposited on 17 Apr. 2014 under the terms of the Budapest Treaty on the International Recognition of the Deposit of Microorganisms for the Purposes of Patent Procedure at the American Type Culture Collection (ATCC) in Manassas, Va., USA and bears the Patent Accession No. PTA-121165. [The strain was initially deposited under the name "*Bacillus amyloliquefaciens* RTI301", but reclassified as "*Bacillus velezensis* RTI301" on 10 Aug. 2017].

Example 3

Genes Related to Biosynthesis of Antimicrobial Compounds in *Bacillus velezensis* RTI301 and *Bacillus Subtilis* RTI477

Further sequence analysis of the genome of the *Bacillus velezensis* RTI301 strain revealed that this strain has genes related to a number of biosynthetic pathways for production of molecules having antimicrobial properties. These include the biosynthetic pathways for subtilosin, surfactin, iturin, fengycins, amylocyclicin, difficidin, bacilysin, bacillomycin, and bacillaene. In addition, genes related to lantibiotic biosynthesis were discovered in the RTI301 strain, for which there are no homologues in the other closely related *Bacillus amyloliquefaciens* strains. This is illustrated in FIG. 1, which shows a schematic diagram of the genomic organization surrounding and including the lantibiotic biosynthesis operon found in *Bacillus velezensis* RTI301. In FIG. 1, the top set of arrows represents protein coding regions for the RTI301 strain with relative direction of transcription indicated. For comparison, the corresponding regions for two *Bacillus amyloliquefaciens* reference strains, FZB42 and TrigoCor1448, are shown below the RTI301 strain. The genes in the lantibiotic synthesis operon in the RTI301 strain were initially identified using RAST and their identities then refined using BLASTp. The degree of amino acid identity of the proteins encoded by the genes of the RTI301 strain as compared to the two reference strains is indicated both by the degree of shading of the representative arrows as well as a percentage identity indicated within the arrow. It can be observed from FIG. 1 that there is a high degree of sequence identity in the genes from the 3 different strains in the regions surrounding the lantibiotic synthesis operon, but only a low degree of sequence identity within the lantibiotic synthesis operon (i.e., less than 40% within the lantibiotic synthesis operon but greater than 99% in the surrounding regions). BLASTn analysis of this cluster was performed against the non-redundant (nr)nucleotide database at NCBI and the analysis showed a high degree of homology in the 5' and 3' flanking regions to *B. amyloliquefaciens* strains (analogous to the high % similarity in FIG. 1). However, the lantipeptide biosynthetic cluster was unique to RTI301, and no significant homology to any previously sequenced DNA in the NCBI nr database was observed. Thus, this lantibiotic synthesis operon is a unique feature for *Bacillus velezensis* strain RTI301.

In contrast to the RTI301 strain with its wide range of antimicrobial biosynthetic pathways, further sequence analysis of the RTI477 strain revealed that this strain has genes related to biosynthetic pathways for a more limited group of molecules having antimicrobial properties. The RTI477 strain has biosynthetic pathways for subtilosin, fengycins, surfactin, difficidin, bacillaene, bacilysin, and bacillomycin, but complete biosynthetic pathways for iturins, lantibiotics, and amylocyclicins were not observed.

Example 4

Anti-Microbial Properties of *Bacillus Subtilis* RTI477 and *Bacillus velezensis* RTI301 Isolates The antagonistic ability of the *Bacillus subtilis* RTI477 and *Bacillus velezensis* RTI301 isolates against major plant pathogens was measured in plate assays. A plate assay for evaluation of antagonism against plant fungal pathogens was performed by growing the bacterial isolate and pathogenic fungi side by side on 869 agar plates at a distance of 4 cm. Plates were incubated at room temperature and checked regularly for up to two weeks for growth behaviors such as growth inhibition, niche occupation, or no effect. In the case of screening for antagonistic properties against bacterial pathogens, the pathogen was first spread as a lawn on 869 agar plates. Subsequently, 20 µl aliquots of a culture of each of the isolates were spotted on the plate. Plates were incubated at room temperature and checked regularly for up to two weeks for an inhibition zone in the lawn around the positions were RTI477 and RTI301 had been applied. A summary of the antagonism activity is shown in Tables I and II below for each of the RTI477 and RTI301 strains, respectively. The RTI301 strain showed superior antagoniscitc properties against a wide range of plant pathogenic microorganisms in comparison to the RTI477 strain.

TABLE I

Antagonistic properties of *Bacillus subtilis* RTI477 isolate against major plant pathogens

| Anti-Microbial Assays | RTI477 |
|---|---|
| *Alternaria solani* | +++ |
| *Aspergillus flavus* | + |
| *Aspergillus nomius* | +− |
| *Botrytis cinerea* | ++ |
| *Cercospora sojina* | ++/+++ |
| *Fusarium colmorum* | + |
| *Fusarium graminearum* | +++ |
| *Fusarium oxysporum* f. sp. *Lycopersici* | + |
| *Fusarium oxysporum* f. sp. *cubense* | + |
| *Fusarium virguliforme* | ++/+++ |
| *Glomerella cingulata* | ++ |
| *Magnaporthe grisea* | +++ |
| *Monilina fructicola* | ++ |
| *Rhizoctonia solani* | ++ |
| *Sclerotinia homeocarpa* | ++ |
| *Sclerotinia sclerotiorum* | + |
| *Septoria tritici* | ++ |
| *Stagonospora nodorum* | ++/+++ |
| *Phytophthora capsici* | ++ |
| *Pythium sylvatium* | +−/+ |
| *Pythium aphanidermatum* | + |
| *Erwinia amylovora* | + |
| *Erwinia carotovora* | + |
| *Pseudomonas syringae* pv. tomato | − |
| *Xanthomonas axonopodis* | + |
| *Xanthomonas euvesicatoria* | + |

+++ very strong activity,
++ strong activity,
+ activity,
+− weak activity,
− no activity observed

TABLE II

Antagonistic properties of *Bacillus velezensis* RTI301 isolate against major plant pathogens.

| Anti-Microbial Assays | RTI301 |
|---|---|
| *Alternaria solani* | ++ |
| *Aspergillus flavus* | ++ |
| *Aspergillus nomius* | +++ |
| *Botrytis cinerea* | +++ |
| *Cercospora sojina* | +++ |
| *Fusarium colmorum* | + |
| *Fusarium graminearum* | +++ |
| *Fusarium oxysporum* f. sp. *Lycopersici* | ++ |
| *Fusarium oxysporum* f. sp. *cubense* | ++ |
| *Fusarium virguliforme* | ++/+++ |
| *Glomerella cingulata* | +++ |
| *Magnaporthe grisea* | ++/+++ |

TABLE II-continued

Antagonistic properties of *Bacillus velezensis* RTI301 isolate against major plant pathogens.

| Anti-Microbial Assays | RTI301 |
|---|---|
| *Monilina fructicola* | ++/+++ |
| *Rhizoctonia solani* | ++ |
| *Sclerotinia homeocarpa* | ++/+++ |
| *Sclerotinia sclerotiorum* | +++ |
| *Septoria tritici* | ++ |
| *Stagonospora nodorum* | ++/+++ |
| *Phytophthora capsici* | ++ |
| *Pythium sylvatium* | +−/+ |
| *Pythium aphanidermatum* | + |
| *Erwinia amylovora* | + |
| *Erwinia carotovora* | + |
| *Pseudomonas syringae* pv. tomato | − |
| *Ralstonia solenacearum* | ++ |
| *Xanthomonas axonopodis* | ++ |
| *Xanthomonas euvesicatoria* | ++ |

+++ very strong activity,
++ strong activity,
+ activity,
+− weak activity,
− no activity observed Example 5

Phenotypic Traits of *Bacillus Subtilis* RTI477 and *Bacillus velezensis* RTI301 Isolates In addition to the antagonistic properties, various phenotypic traits were also measured for the *Bacillus subtilis* RTI477 and *Bacillus velezensis* RTI301 strains and the data are shown below in Tables III and IV for each of the strains respectively. The assays were performed according to the procedures described in the text below the Tables. Notably, RTI477 grows faster and has a strong swarming phenotype as compared to RTI301.

TABLE III

Phenotypic Assays: phytohormone production, acetoin and indole acetic acid (IAA), and nutrient cycling of *Bacillus subtilis* RTI477 isolate

| Characteristic Assays | RTI477 |
|---|---|
| Acid Production (Methyl Red) | − |
| Acetoin production (MR-VP) | ++ |
| Chitinase activity | − |
| Indole-3-Acetic Acid production | − |
| Protease activity | ++ |
| Phosphate solubilization | +− |
| Phenotype | dry cream, large growth, strong swarming |

+++ very strong,
++ strong,
+ some,
+− weak,
− none observed

TABLE IV

Phenotypic Assays: phytohormone production, acetoin and indole acetic acid (IAA), and nutrient Cycling of *Bacillus velezensis* RTI301 isolate.

| Characteristic Assays | RTI301 |
|---|---|
| Acid Production (Methyl Red) | − |
| Acetoin Production (MR-VP) | +++ |

TABLE IV-continued

Phenotypic Assays: phytohormone production, acetoin and indole acetic acid (IAA), and nutrient Cycling of *Bacillus velezensis* RTI301 isolate.

| Characteristic Assays | RTI301 |
|---|---|
| Chitinase activity | +− |
| Indole-3-Acetic Acid production | − |
| Protease activity | +++ |
| Phosphate Solubilization | +− |
| Phenotype | slimy cream, well-defined, round colonies |

+++ very strong,
++ strong,
+ some,
+− weak,
− none observed

Acetoin Test.

20 μl of a starter culture in rich 869 media was transferred to 1 ml Methy Red—Voges Proskauer media (Sigma Aldrich 39484). Cultures were incubated for 2 days at 30 C 200 rpm. 0.5 ml culture was transferred and 50 μl 0.2 g/l methyl red was added. Red color indicated acid production. The remaining 0.5 ml culture was mixed with 0.3 ml 5% alpha-napthol (Sigma Aldrich N1000) followed by 0.1 ml 40% KOH. Samples were interpreted after 30 minutes of incubation. Development of a red color indicated acetoin production. For both acid and acetoin tests non-inoculated media was used as a negative control (Sokol et al., 1979, *Journal of Clinical Microbiology.* 9: 538-540).

Indole-3-Acetic Acid.

20 μl of a starter culture in rich 869 media was transferred to 1 ml 1/10 869 Media supplemented with 0.5 g/l tryptophan (Sigma Aldrich T0254). Cultures were incubated for 4-5 days in the dark at 30 C, 200 RPM. Samples were centrifuged and 0.1 ml supernatant was mixed with 0.2 ml Salkowski's Reagent (35% perchloric acid, 10 mM FeCl3). After incubating for 30 minutes in the dark, samples resulting in pink color were recorded positive for IAA synthesis. Dilutions of IAA (Sigma Aldrich 15148) were used as a positive comparison; non inoculated media was used as negative control (Taghavi, et al., 2009, *Applied and Environmental Microbiology* 75: 748-757).

Phosphate Solubilizing Test.

Bacteria were plated on Pikovskaya (PVK) agar medium consisting of 10 g glucose, 5 g calcium triphosphate, 0.2 g potassium chloride, 0.5 g ammonium sulfate, 0.2 g sodium chloride, 0.1 g magnesium sulfate heptahydrate, 0.5 g yeast extract, 2 mg manganese sulfate, 2 mg iron sulfate and 15 g agar per liter, pH7, autoclaved. Zones of clearing were indicative of phosphate solubilizing bacteria (Sharma et al., 2011, *Journal of Microbiology and Biotechnology Research* 1: 90-95).

Chitinase Activity.

10% wet weight colloidal chitin was added to modified PVK agar medium (10 g glucose, 0.2 g potassium chloride, 0.5 g ammonium sulfate, 0.2 g sodium chloride, 0.1 g magnesium sulfate heptahydrate, 0.5 g yeast extract, 2 mg manganese sulfate, 2 mg iron sulfate and 15 g agar per liter, pH7, autoclaved). Bacteria were plated on these chitin plates; zones of clearing indicated chitinase activity (N. K. S. Murthy & Bleakley., 2012. "Simplified Method of Preparing Colloidal Chitin Used for Screening of Chitinase Producing Microorganisms". *The Internet Journal of Microbiology.* 10(2)).

Protease Activity.

Bacteria were plated on 869 agar medium supplemented with 10% milk. Clearing zones indicated the ability to break down proteins suggesting protease activity (Sokol et al., 1979, *Journal of Clinical Microbiology.* 9: 538-540).

Example 6

Growth Effects of *Bacillus Subtilis* RTI477 Isolate in Wheat

The effect of application of the bacterial isolate RTI477 on early plant growth and vigor in wheat was determined. The experiment was performed by inoculating surface sterilized germinated wheat seeds for 2 days in a suspension of ~2×10$^7$ CFU/ml of the bacterium at room temperature under aeration in the dark (a control was also performed without bacteria). Subsequently, the inoculated and control seeds were planted in 6" pots filled with sand. 10 seeds per pot and 1 pot per treatment were planted and watered as needed alternating with water and Modified Hoagland's solution. Pots were incubated in a lab windowsill at approximately 21° C. providing natural light/dark cycles for 13 days at which point plants were recovered and parameters measured. Dry weight was determined as a total weight per 9 plants resulting in a total average dry plant weight equal to 35.41 mg for the plants inoculated with the *Bacillus subtilis* RTI477 strain versus a weight equal to 33.38 mg for the non-inoculated control which is a 6% increase in dry weight over the non-inoculated control. Photographs of the extracted plants after 13 days growth are shown in FIG. 2. FIG. 2A shows control plants and FIG. 2B shows plants inoculated with RTI477.

Example 7

Growth Compatibility of *Bacillus velezensis* RTI301 and *Bacillus Subtilis* RTI477

The compatability of the strain *Bacillus velezensis* RTI301 with other *Bacillus* isolates was tested by spotting the RTI301 strain onto a lawn of the various other strains. Results of this experiment are shown in FIGS. 3A-3B. FIGS. 3A-3B are images showing the growth compatibility between strains *Bacillus velezensis* RTI301 and *Bacillus subtilis* RTI477 and a lack of compatibility between the RTI301 strain with another *Bacillus amyloliquefaciens* strain, *Bacillus amyloliquefaciens* RTI472 deposited as PTA-121166 with the American Type Culture Collection (ATCC). When strain RTI301 was spotted onto a lawn of strain RTI472 (FIG. 3A), a clear inhibition zone was observed for the growth of strain RTI472. In contrast, when strain RTI301 was spotted onto a lawn of strain RTI477 (FIG. 3B), only minimal inhibition and no clearing of the cell lawn was observed for the RTI477 strain. Therefore, it was concluded that the growth of RTI301 and RTI477 is compatible.

Without being limited to any particular mechanism of action, one mode of action is proposed as follows to explain the observed differences in strain compatibility. Based on the genome sequences of the three strains tested (i.e., RTI301, RTI472, and RTI477), these strains were all predicted to produce the antagonistic compounds bacilysin, bacillaene, difficidin, and bacillomycin. However, while both *Bacillus velezensis* RTI301 and *Bacillus subtilis* RTI477 possess the gene for synthesis of subtilosin, this gene is absent in the genome of *Bacillus amyloliquefaciens* RTI472. Subtilosin is a bacteriocin, a class of proteinaceous toxins produced by bacteria to inhibit the growth of similar or closely related bacterial strain(s). Therefore, it was postulated that the subtilosin synthesized by *Bacillus velezensis* RTI301 could be the inhibitor of the growth of *Bacillus amyloliquefaciens* RTI472. In contrast, the *Bacillus subtilis* RTI477 strain is not inhibited by RTI301, because the RTI477 strain produces its own subtilosin and is thus resistant to the compound.

The differences in strain morphology between the *Bacillus velezensis* RTI301 and *Bacillus subtilis* RTI477 strains were also analyzed. Images showing the morphology of each of these strains are shown in FIG. 4: *Bacillus velezensis* RTI301 (FIG. 4A) and *Bacillus subtilis* RTI477 (FIG. 4B). The colony morphology of the *Bacillus velezensis* RTI301 and *Bacillus subtilis* RTI477 strains shown in FIGS. 4A-4B indicate a potential difference in strain behavior when it comes to motility. Motility is a key trait for rhizosphere colonization by plant associated bacteria. *Bacillus velezensis* RTI301 grows as well-defined, round colonies. In contrast, *Bacillus subtilis* RTI477 grows as a fluffy colony, a morphology which is indicative of swarming and motility. Swarming and motility are potentially important phenotypes for the rapid colonization of the rhizosphere and the surface of the plant root. Again, without being limited to any particular mechanism of action, it was postulated that the strong swarming phenotype suggested by the morphology of the *Bacillus subtilis* RTI477 strain, could cause this strain to be a more efficient colonizer of the rhizosphere than *Bacillus velezensis* RTI301.

In light of the growth compatibility and observed differences in phenotype, the combination of the RTI301 and RTI477 strains was further tested for activity in promoting plant growth and health.

Example 8

Combination of *Bacillus Subtilis* RTI477 and *Bacillus velezensis* RTI301 Results in Synergistic Plant Growth Promoting Properties A positive effect on seed germination and root development and architecture was observed for a variety of plant seeds inoculated with vegetative cells or coated with spores of the *Bacillus subtilis* RTI477 strain. This is described in wheat, for example, herein above at EXAMPLE 6. In addition, experiments were performed to determine the effects of application of *Bacillus subtilis* RTI477 and *Bacillus velezensis* RTI301 strains to soybean seed on germination, root development and architecture, and early plant growth and/or plant health. Experiments were performed as described below using spores of RTI301 and RTI477. For the experiments, the strains were sporulated in 2XSG in a 14 L fermenter. Spores were collected but not washed afterwards at a concentration of $1.0 \times 10^8$ CFU/mL. The spore concentration was diluted down by a factor of 10 or greater in the experiments. A sterile filter paper was placed in the bottom of individual sterile plastic growth chambers, and six seeds were placed in each container. Three mL of each dilution of the RTI301 or RTI477 spores was added to the growth chambers, which were closed and incubated at 19° C. for 8 days, after which the seedlings were imaged. In addition, combinations of RTI301 and RTI477 spores added in ratios of 1:3, 1:1 and 3:1 were also tested. Data are shown in Table V below. Neither of the two strains when applied alone inhibited seed germination as compared to non-inoculated controls.

Inoculation of soybean seeds with *Bacillus velezensis* RTI301 at concentrations of $1 \times 10^6$, $1 \times 10^7$, and $1 \times 10^8$ had no effect on root development and architecture. Inoculation of soybean seeds with *Bacillus subtilis* RTI477 at the same concentrations provided only a slight improvement at the lowest concentration on root development and architecture. Unexpectedly, inoculation of soybean seeds with the combination of both RTI301 and RTI477 (ratio 1:3) resulted at all concentrations tested in an improvement in root development. Inoculation of soybean seeds with the combination of RTI301 and RTI477 (ratio 1:1) resulted for the concentrations of $1 \times 10^6$ CFU/ml and $1 \times 10^7$ CFU/ml in an improvement in root development, with the most consistent results observed for the concentration of $1 \times 10^6$ CFU/ml. The best results on root development were observed when RTI301 and RTI477 were applied in a ratio of 3:1 at the concentration of $1 \times 10^6$ CFU/ml.

In addition, images of the positive effects of inoculation of the seed with the RTI301 plus RTI477 spores (ratio 3:1) are shown in FIGS. 5A and 5B (A—Control plants; B—plants inoculated with RTI301 plus RTI477 (ratio 3:1) at $10^6$ cfu/ml). The effects were especially positive with regards to root formation and architecture, as shown in FIGS. 5A-5B. Fine root hairs are important in the uptake of water, nutrients and plant interaction with other microorganisms in the rhizosphere. These results show that while the application of individual strains had no or little effect compared to control plants, seed treatment with application of a combination of *Bacillus subtilis* RTI477 and *Bacillus velezensis* RTI301 strains can have significant benefit on soybean early growth and establishment.

TABLE V

Soybean seed germination assay for treatment with spores of RTI301 and RTI477

| | | Effect of spore concentration (CFU/ml) on soybean germination and root development | | |
|---|---|---|---|---|
| Strain | ID | $10^8$ | $10^7$ | $10^6$ |
| RTI 301 | *B. velezensis* | = | = | = |
| RTI 477 | *B. subtilis* | = | = | + |
| RTI 301 + RTI 477 | *B. velezensis* + *B. subtilis* 1:3 | + | ++ | + |
| RTI 301 + RTI 477 | *B. velezensis* + *B. subtilis* 1:1 | = | + | ++ |
| RTI 301 + RTI 477 | *B. velezensis* + *B. subtilis* 3:1 | = | = | +++ |

+++ very pronounced growth benefit,
++ strong growth benefit,
+ growth benefit,
+− weak growth benefit,
= no effect observed,
− weak inhibition,
−− strong inhibition,
n.d. not determined Additional experiments were performed to investigate the effect on plant growth and development after inoculation of the plant seed with a combination of the RTI301 and RTI477 strains. Specifically, an experiment in soybean was set up as follows: 1) seed was untreated; 2) seed was treated with a combination of CRUISERMAXX (insecticide plus fungicide, containing thiamethoxam, fludioxonil plus metalaxyl-M; SYNGENTA CROP PROTECTION, INC) and the thiophanate methyl fungicide, which is a typical soybean seed treatment (the combination of CRUISERMAXX and thiophanate methyl is referred to as "CHEM CONTROL"); 3)

seed was treated with CHEM CONTROL plus inoculated with $5.0 \times 10^{+5}$ cfu/seed of strain RTI301; 4) seed was treated with CHEM CONTROL plus inoculated with $5.0 \times 10^{+5}$ cfu/seed of strain RTI477; 5) seed was treated with CHEM CONTROL plus inoculated with a combination of both strains at $5.0 \times 10^{+5}$ cfu/seed. Ten trials were performed with 4 or 5 replicates per treatment per trial. The average soybean yield results (bushels per acre) for ten field trials are presented in Table VI below, with trial field sites being located in Wisconsin(2), Indiana(2), Illinois (3) and Iowa (3). Four trials were inoculated with *Rhizoctonia solani*, three trials were inoculated with either *Fusarium graminearum* or *F. virguliforme*, one trial was inoculated with *Phytophthora sojae* and two trials were non-inoculated. Each pathogen was grown separately on moisten autoclaved grain seed and then air dried. The dried inoculum used in a selected trial was planted mixed with the seed at a prescribed rate to provide infection when the seed commenced to grow.

The results in Table VI show that inoculation with either *Bacillus velezensis* RTI301 or *Bacillus subtilis* RTI477 alone had no effect on the overall average yield of soybean when compared to seeds that were treated with the CHEM CONTROL alone. As was observed in the previous experiment, inoculating with the combination of the *Bacillus velezensis* RTI301 and *Bacillus subtilis* RTI477 provided a synergistic effect and resulted on average over 10 field trials in a 5% increase in soybean yield (from 58.2 to 61.1 bushels per acre, see Table VI). Notably, a yield benefit of 3.7 bushels per acre was observed with the combination of RTI 301 and RTI 477 plus chemical control over the chemical control for yields in non-inoculated field trials (N=2 trials), 4.3 bushels per acre increase for the two strains plus chemical control over the chemical control for trials inoculated with *Rhizoctonia* (N=4 trials), 1.5 bushels per acre increase for the two strains plus chemical control over the chemical control for trials inoculated with *Fusarium* (N=3 trials), and 1.0 bushels per acre increase for the two strains plus chemical control over the chemical control for trials inoculated with *Phytophthora* (N=1 trial), so a yield response occurred irrespective of disease inoculation and seed treatment with chemical fungicides.

TABLE VI

Average results of inoculation of soybean seed with *Bacillus velezensis* RTI301, *Bacillus subtilis* RTI477 and the combination of both strains.

|   | TREATMENT | Yield (Bu/Acre) n = 10 | Yield Increase Over CHEM CONTROL | Paired T-test Value |
|---|---|---|---|---|
| 1 | UNTREATED SEED | 55.6 | −2.6 | 0.011 |
| 2 | CHEM CONTROL | 58.2 | ~ | ~ |
| 3 | CHEM CONTROL + RTI301 | 58.1 | −0.1 | 0.468 |
| 4 | CHEM CONTROL + RTI477 | 58.1 | −0.1 | 0.460 |
| 5 | CHEM CONTROL + RTI301 + RTI477 | 61.1 | 2.9 | 0.007 |

Without being limited to any particular mechanism of action, one explanation for the observed synergistic results of the combination of the two strains on soybean yield is as follows. *Bacillus velezensis* RTI301 produces a wide range of antagonistic metabolites, such as subtilosin, that can inhibit the growth and development of competing strains both fungi and bacteria, including closely related *Bacillus* species. By doing so, the RTI301 strain when applied to a plant alone could open a niche/space for its establishment in the rhizosphere. However, data do not support strong plant growth promoting properties for *Bacillus velezensis* RTI301. Thus, after the RTI301 strain has been introduced and has opened a niche in the rhizosphere, it could become established but fail to significantly promote plant growth and/or plant health. This is confirmed by the lack of an observed yield increase for soybean after seed treatment with *Bacillus velezensis* RTI301 alone.

In contrast, *Bacillus subtilis* RTI477 appears to have a narrower range of antagonism than *Bacillus velezensis* RTI301 and, thus, could be expected to be less efficient in opening a niche in which to become established when it is applied to plant seed alone. As a result, the strain could more easily fail to become established in the rhizosphere of soybean which could result in a lack of a beneficial effect on plant growth. This is confirmed by the observed lack of an increase in yield for soybean after seed treatment with *Bacillus subtilis* RTI477 alone.

Experiments have shown that the growth of the *Bacillus subtilis* RTI477 strain is compatible with *Bacillus velezensis* RTI301. In addition, the phenotype of RTI477 indicates that this strain can be a strong swarming phenotype and it is thus hypothesized to be a more efficient colonizer of the rhizosphere than *Bacillus velezensis* RTI301. Therefore, the combination of both strains can be expected to have a beneficial effect on soybean. Specifically, once *Bacillus velezensis* RTI301 has opened a niche for establishment in the soybean rhizosphere, the strain can be outcompeted by *Bacillus subtilis* RTI477 due to its swarming phenotype. The RTI477 strain can then establish itself in the rhozosphere of soybean, where it can provide beneficial effects to its plant host. This was confirmed by the observed increase in yield of soybean after inoculation of the plant seed with a combination of both of the strains.

Example 9

Seed Treatment with a Combination of *Bacillus Subtilis* RTI477 and *Bacillus velezensis* RTI301 Spores Increased Yield in Corn Additional experiments were performed to investigate the effect on plant growth, development, and yield after inoculation of the plant seed with a combination of the RTI301 and RTI477 strains.

Specifically, an experiment in corn was set up as follows and the data are summarized in Table IX below: 1) seed was untreated ("UTC"); 2) seed was treated with a combination of MAXIM (broad-spectrum seed treatment fungicide fludioxonil as its active ingredient at 0.0625 mg/seed; SYNGENTA CROP PROTECTION, INC), APRON XL (active ingredient metalaxyl-M at 0.0625 mg/seed); SYNGENTA CROP PROTECTION, INC) and PONCHO (Clothianidin insecticide at 0.25 mg/seed; BAYER CROPSCIENCE, INC), which is a typical corn seed treatment (the combination of MAXIM, APRON XL and PONCHO is referred to as "CHEM CONTROL" or "CC"); and 3) seed was treated with CHEM CONTROL plus a combination of $5.0 \times 10^{+5}$ cfu/seed of each of strains RTI301 and RTI477 ("CC+RTI 301/477 1:1"). Two trials were performed with 5 replicates per treatment per trial, under conditions of natural disease pressure or inoculation of the soil with *Rhizoctonia*, respectively. For the inoculation trial, *Rhizoctonia* was grown separately on moistened autoclaved grain seed and then air dried. The dried inoculum was mixed with the seed at planting at a prescribed rate to provide infection when the seed commenced to grow. The average corn yield results (bushels per acre) for the field trials are presented in Table IX below, with trial field sites being located in Shawneetown, Ill.

The results in Table VII show that inoculation with the CHEM CONTROL plus the 1 to 1 combination of *Bacillus velezensis* RTI301 and *Bacillus subtilis* RTI477 significantly increased the average corn yield when compared to seeds that were treated with the CHEM CONTROL alone. Notably, a yield increase of 10.7 bushels per acre and 59.8 bushels per acre was observed with the 1:1 combination of RTI301 and RTI477 plus chemical control over the chemical control alone for the natural pathogen pressure and the *Rhizoctonia* inoculated field trials, respectively. These data indicate that treatment of seed with the combination of these strains significantly enhances corn yield.

TABLE VII

Yield increase for untreated corn seed (UTC), corn seed treated with chemical control (CC), and corn seed treated with CC plus a combination of *Bacillus velezensis* RTI301 and *Bacillus subtilis* RTI477 under both natural disease pressure and artificial inoculation with *Rhizoctonia*. The statistical relevance (as letters) is based on $P = 0.1$.

|   |                  | Natural   |          | Rhizoctonia |          |
|---|------------------|-----------|----------|-------------|----------|
|   |                  | Bu/Acre   | Increase | Bu/Acre     | Increase |
| 1 | UTC              | 170.7 e   | −23.8    | 142 e       | −22.0    |
| 2 | CC               | 194.5 bcd | 0.0      | 164 de      | 0.0      |
| 3 | CC + RTI 301/477 1:1 | 205.2 a-d | 10.7 | 223.8 ab    | 59.8     |

Example 10

Seed Treatment with a Combination of *Bacillus Subtilis* RTI477 and *Bacillus velezensis* RTI301 Increased Yield in Soybean Artificially Inoculated with *Rhizoctonia solani*

Experiments were performed to investigate the effect on emergence and yield in soybean when seeds were treated with a combination of the RTI301 and RTI477 strains in addition to chemical active agents for pathogen control. Specifically, an experiment in soybean was set up as follows: 1) seed was untreated (UTC); 2) seed was treated with a combination of CRUISERMAXX (insecticide plus fungicide, containing thiamethoxam, fludioxonil plus metalaxyl-M; SYNGENTA CROP PROTECTION, INC) and the thiophanate methyl fungicide, which is a typical soybean seed treatment (the combination of CRUISERMAXX and thiophanate methyl is referred to as "CHEM CONTROL"); 3) seed was treated with VIBRANCE (active ingredient Sedaxane; SYNGENTA CROP PROTECTION, INC; and 4) seed was treated with CHEM CONTROL plus $5.0 \times 10^{+5}$ cfu/seed of each of strain RTI301 and RTI477. Two trials were performed in Whitewater, Wis. with 4 replicates per treatment per trial. The trials were inoculated with *Rhizoctonia solani* by first growing the pathogen separately on moistened autoclaved grain seed and subsequently the dried inoculum was mixed with the seed at the time of planting to a prescribed rate to provide infection when the seed commenced to grow. The average soybean emergence and yield results for the trials are presented in Table VIII below. The results in Table VIII show that treating with the combination of the *Bacillus velezensis* RTI301 and *Bacillus subtilis* RTI477 in addition to the CHEM CONTROL resulted in an average increase in yield of 13.3 bushels per acre over that of the chemical active agent alone (from 59.4 to 72.7 bushels per acre). Thus, seed treatment with the combination of RTI301 and RTI477 can provide significant improvement in yields in soybean, even under conditions of severe pathogen pressure.

TABLE VIII

Average results on soybean emergence and yield in field trials with plants artificially inoculated with *Rhizoctonia solani* with treatment of the soybean seed with a combination of *B. velezensis* RTI301 and *B. subtilis* RTI477 in addition to chemical active agent treatment for soybean seeds.

|   | TREATMENT | % Emergence | Yield (Bu/Acre) | Yield Increase Over CHEM CONTROL (Bu/Acre) |
|---|-----------|-------------|-----------------|-----|
| 1 | UTC | 36 | 49.3 | −10.1 |
| 2 | CHEM CONTROL | 49 | 59.4 | — |
| 3 | VIBRANCE | 56 | 60.8 | 1.4 |
| 4 | CHEM CONTROL + RTI301 + RTI477 | 65 | 72.7 | 13.3 |

Example 11

Effects of Drip Irrigation with *Bacillus velezensis* Isolate RTI301 Plus *Bacillus subtilis* Isolate RTI477 on Fruit and Vegetables Field trial experiments were performed to determine the effect of drip irrigation with spores of *Bacillus velezensis* RTI301 plus *Bacillus subtilis* RTI477 on squash, tomato and pepper. Disease pressure caused by soil-borne fungi was not recorded for any of the trails. The effects on plant yield were determined according to the experiments described below.

A field trial was performed for pepper plants (jalapeno pepper) where spores were applied at a rate of $1.25 \times 10^{12}$ CFU/hectare per strain of both *Bacillus velezensis* RTI301 and *Bacillus subtilis* RTI477 at the time of planting via a root-zone drench, followed by two drip applications of the same rate at 17 and 35 days after transplanting. ACCOMPLISH LM (LOVELAND PRODUCTS) was used as the commercial control and was applied in the same manner as described for the RTI301+RTI477 combination at a rate of 2340 ml/Ha. This product contains a blend of Acidovorax *facilis* ($1 \times 10^3$ cfu/ml), *Bacillus licheniformis* ($1 \times 10^3$ cfu/ml), *Bacillus subtilis* ($1 \times 10^3$ cfu/ml), *Bacillus oleronius* ($1 \times 10^3$ cfu/ml), *Bacillus marinus* ($1 \times 10^3$ cfu/ml), *Bacillus megaterium* ($1 \times 10^3$ cfu/ml), and *Rhodococcus rhodochrous* ($1 \times 10^3$ cfu/ml).

The addition of the RTI301 plus RTI477 spores resulted in an increase in yield for jalapeno peppers as compared to untreated control plants in which bacterial spores were not applied, as well as in comparison to the commercial control plants. Specifically, RTI301+RTI477 treated plants resulted in a total of 4154 kg/Ha marketable peppers, as compared to 3455 kg/Ha and 3930 kg/Ha for the untreated control plants and the plants treated with ACCOMPLISH, respectively, representing a 20% and a 5.7% respective increase in weight of marketable peppers. The substantial increase in marketable pepper weight of the plants treated with *Bacillus velezensis* RTI301 plus *Bacillus subtilis* RTI477 spores relative to the untreated control plants and the plants treated with the commercial standard demonstrates the positive growth effect provided by this treatment.

A similar field trial was performed for tomato plants where spores were applied at a rate of $0.625 \times 10^{12}$ CFU/hectare for *Bacillus velezensis* RTI301 and at a rate of $3.75 \times 10^{12}$ CFU/hectare for *Bacillus subtilis* RTI477 at the time of planting via a root-zone drench, followed by two drip applications of the same rate at 17 and 35 days after transplanting. ACCOMPLISH LM was used as the commercial control and applied in the same manner as described for the RTI301+RTI477 combination at a rate of 2340 ml/Ha.

The addition of the RTI301 plus RTI477 spores resulted in an increase in both total and marketable yield for tomatoes compared to untreated control plants in which bacterial spores were not included in the drench and the irrigation, as well as in comparison to the commercial control plants. Specifically, RTI301+RTI477 treated plants resulted in a total of 21,824 kg/Ha marketable tomatoes, as compared to 16,765 kg/Ha and 21,420 kg/Ha for the untreated control plants and the plants treated with ACCOMPLISH, respectively, representing a 30.2% and 1.9% respective increase in weight of marketable tomatoes. The substantial increase in marketable tomato weight of the plants treated with *Bacillus velezensis* RTI301 plus *Bacillus subtilis* RTI477 spores, especially compared to the untreated control plants, demonstrates the positive growth effect provided by this treatment.

A similar field trial was performed for squash plants where spores were applied at a rate of $3.75 \times 10^{12}$ CFU/hectare for *Bacillus velezensis* RTI301 and at a rate of $0.625 \times 10^{12}$ CFU/hectare for *Bacillus subtilis* RTI477 at the time of planting via a root-zone drench, without further application via drip irrigation. ACCOMPLISH LM was used as the commercial control and applied in the same manner as described for the RTI301+RTI477 combination at a rate of 2340 ml/Ha.

The addition of the RTI301 plus RTI477 spores resulted in an increase in both total and marketable yield for squash compared to untreated control plants in which bacterial spores were not included in the drench, as well as in comparison to the commercial control plants. Specifically, RTI301+RTI477 treated plants resulted in a total of 873.4 kg/Ha squash, as compared to 838.3 kg/Ha and 836.1 kg/Ha for the untreated control plants and the plants treated with ACCOMPLISH, respectively, representing a 4.2% and 4.5% respective increase in weight of total squash. The increase in total squash weight of the plants treated with *Bacillus velezensis* RTI301 plus *Bacillus subtilis* RTI477 spores relative to the untreated control plants and the plants treated with the commercial standard demonstrates the positive growth effect provided by this treatment.

Example 12

Identification of New Metabolites Produced by *Bacillus Subtilis* RTI477 and *Bacillus* Velezensis RTI301 Isolates It has been previously reported that five classes of Fengycin-type metabolites and Dehydroxyfengycin-type metabolites are produced by microbial species including *Bacillus subtilis* and *Bacillus amyloliquefaciens* (see, for example, Li, Xing-Yu, et al., 2013, *J. Microbiol. Biotechnol.* 23(3), 313-321; Pecci Y, et al. 2010, *Mass Spectrom.*, 45(7):772-77). These metabolites are cyclic peptide molecules that also contain a fatty acid group. The five classes of Fengycin- and Dehydroxyfengycin-type metabolites are referred to as A, B, C, D and S. The backbone structure of these metabolites as well as the specific amino acid sequence for each of the five classes is shown in FIG. 6. In *Bacillus subtilis* the Fengycin-type compounds are referred to as Plipastatins. Plipastatin A and B are similar in molecular weight to Fengycin A and B, and only differ in the aspect that the Tyrosine residue at position 3 of the peptide ring is the D-form in the Fengycins and the L-form in the Plipastatins, and the Tyrosine residue at position 9 of the peptide ring is the L-form in the Fengycins and the D-form in the Plipastatins. (Marc Ongena and Philippe Jacques, 2007, *Trends in Microbiology* Vol. 16, No. 3: 115-125). For the purposes of this specification and claims, the term "Fengycin" will be used to refer to both Plipastatin metabolites and Fengycin metabolites. Similarly, for the purposes of this specification and claims, the term "Dehydroxyfengycin" will be used to refer to both Dehydroxyplipastatin metabolites and Dehydroxyfengycin metabolites.

The Fengycin- and Dehydroxyfengycin-type metabolites produced by *Bacillus subtilis* RTI477 and *Bacillus velezensis* RTI301 were analyzed using UHPLC-TOF MS. The molecular weights of the these metabolites produced by the strains after 6 days growth in 869 medium or 2×SG medium at 30° C. were compared to the theoretical molecular weights expected for the Fengycin- and Dehydroxyfengycin-type metabolites. In addition, to determine the amino acid composition of the various Fengycin-type metabolites produced by the strains, peptide sequencing using LC-MS-MS was performed on each of the Fengycin-type metabolites previously identified via UHPLC-TOF MS. In this manner, it was determined that the strains produce Fengycin A, B, C, D, and S and Dehydroxyfengycin A, B, C, D, and S. Surprisingly, in addition to these known compounds, it was determined that the strains also produce previously unidentified derivatives of these compounds.

For example, it was determined that the *Bacillus velezensis* RTI301 strain produces Fengycin-like and Dehydroxyfengycin-like compounds where the L-isoleucine at position 8 of the cyclic peptide chain (referred to as $X_3$ in FIG. 6) is replaced by L-methionine. The new classes of Fengycin and Dehydroxyfengycin are referred to herein as MA, MB and MC, referring to derivatives of classes A, B and C in which the L-isoleucine at $X_3$ in FIG. 6 has been replaced by L-methionine. The newly identified molecules are shown in FIG. 6 and in Table IX below. The newly identified Fengycin MA, MB and MC compounds were also observed for the RTI477 strain, however the corresponding Dehydroxyfengycin MA, MB and MC compounds were not observed for the RTI477 strain (Table IX).

It was further determined that the RTI301 strain produces an additional class of Fengycin and Dehydroxyfengycin that has not been previously identified. In this class, the L-isoleucine of Fengycin B and Dehydroxyfengycin B (position $X_3$ in FIG. 6) is replaced by L-homo-cysteine (Hcy). These previously unidentified Fengycin and Dehydroxyfengycin metabolites are referred to herein as Fengycin H and Dehydroxyfengycin H and are shown in in FIG. 6 and Table IX. The newly identified Fengycin H compound was also observed for the RTI477 strain, however the corresponding Dehydroxyfengycin H compound was not observed for the RTI477 strain (Table IX).

It was further determined that the RTI301 strain produces an additional class of previously unidentified Fengycin and Dehydroxyfengycin metabolites. In this class, the amino acid at position 4 of the cyclic peptide backbone structure (position $X_1$ in FIG. 6) is replaced by L-isoleucine. These previously unidentified metabolites are referred to herein as Fengicin I and Dehydroxyfengicin I and are shown in FIG. 6 and in Table IX. Both the newly identified Fengycin I and Dehydroxyfengycin I compounds were also observed for the RTI477 strain (Table IX).

A summary of the amino acid sequences for the previously reported Fengycin- and Dehydroxyfengycin-type metabolites and the newly identified metabolites is provided in Table IX below.

TABLE IX

Summary of MS/MS identification of Fengycin-type metabolites in *Bacillus subtilis* RTI477 and *Bacillus velezensis* RTI301 isolates.

| Homolog | $X_1$ | $X_2$ | $X_3$ | R | Ring Mass | Theoretical C16 Molecular Formula | Theoretical C16 $[M+H]^+$ | Observed RTI301 | Observed RTI477 |
|---|---|---|---|---|---|---|---|---|---|
| Fengycin A | Ala | Thr | Ile | OH | 1080.6 | $C_{72}H_{110}N_{12}O_{20}$ | 1463.8 | C15, C16, C17 | C14, C15, C16, C17 |
| Fengycin B | Val | Thr | Ile | OH | 1108.7 | $C_{74}H_{114}N_{12}O_{20}$ | 1491.8 | C14, C15, C16, C17 | C14, C15, C16, C17 |
| Fengycin C | Aba | Thr | Ile | OH | 1094.6 | $C_{73}H_{112}N_{12}O_{20}$ | 1477.8 | C14, C15, C16, C17 | C14, C15, C16, C17 |
| Fengycin D | Val | Thr | Val | OH | 1094.6 | $C_{73}H_{112}N_{12}O_{20}$ | 1477.8 | C14, C15, C16, C17 | C14, C15, C16, C17 |
| Fengycin S | Val | Ser | Ile | OH | 1094.6 | $C_{73}H_{112}N_{12}O_{20}$ | 1477.8 | C14, C15, C16, C17 | C14, C15, C16, C17 |
| Fengycin MA | Ala | Thr | Met | OH | 1098.7 | $C_{71}H_{108}N_{12}O_{20}S$ | 1481.8 | C15, C16, C17 | C15, C16, C17 |
| Fengycin MB | Val | Thr | Met | OH | 1126.8 | $C_{73}H_{112}N_{12}O_{20}S$ | 1509.8 | C14, C15, C16 | C14, C15, C16, C17 |
| Fengycin MC | Aba | Thr | Met | OH | 1112.7 | $C_{72}H_{110}N_{12}O_{20}S$ | 1495.8 | C14, C15, C16, C17 | C14, C15, C16, C17 |
| Fengycin H | Val | Thr | Hcy | OH | 1112.7 | $C_{72}H_{110}N_{12}O_{20}S$ | 1495.8 | C14, C15, C16, C17 | C14, C15, C16, C17 |
| Fengycin I | Ile | Thr | Ile | OH | 1122.8 | $C_{75}H_{116}N_{12}O_{20}$ | 1505.8 | C16, C17 | C16 |
| Dehydroxyfengycin A | Ala | Thr | Ile | H | 1080.6 | $C_{72}H_{110}N_{12}O_{19}$ | 1447.8 | C15, C16, C17 | C14, C15, C16, C17 |
| Dehydroxyfengycin B | Val | Thr | Ile | H | 1108.7 | $C_{74}H_{114}N_{12}O_{19}$ | 1475.8 | C14, C15, C16, C17 | C14, C15, C16, C17 |
| Dehydroxyfengycin C | Aba | Thr | Ile | H | 1094.6 | $C_{73}H_{112}N_{12}O_{19}$ | 1461.8 | C14, C15, C16, C17 | C14, C15, C16, C17 |
| Dehydroxyfengycin D | Val | Thr | Val | H | 1094.6 | $C_{73}H_{112}N_{12}O_{19}$ | 1461.8 | C14, C15, C16, C17 | C14, C15, C16, C17 |
| Dehydroxyfengycin S | Val | Ser | Ile | H | 1094.6 | $C_{73}H_{112}N_{12}O_{19}$ | 1461.8 | C14, C15, C16, C17 | C14, C15, C16, C17 |
| Dehydroxyfengycin MA | Ala | Thr | Met | H | 1098.7 | $C_{71}H_{108}N_{12}O_{19}S$ | 1465.7 | C14 | Not observed |
| Dehydroxyfengycin MB | Val | Thr | Met | H | 1126.8 | $C_{73}H_{112}N_{12}O_{19}S$ | 1493.8 | C15 | Not observed |
| Dehydroxyfengycin MC | Aba | Thr | Met | H | 1112.7 | $C_{72}H_{110}N_{12}O_{19}S$ | 1479.8 | C15 | Not observed |
| Dehydroxyfengycin H | Val | Thr | Hcy | H | 1112.7 | $C_{72}H_{110}N_{12}O_{19}S$ | 1479.8 | C14, C15, C16 | Not observed |
| Dehydroxyfengycin I | Ile | Thr | Ile | H | 1122.8 | $C_{75}H_{116}N_{12}O_{19}$ | 1489.9 | C14, C15, C16 | C14, C15, C16 |

REFERENCES

All publications, patent applications, patents, and other references cited herein are incorporated herein by reference in their entireties. Although the foregoing subject matter has been described in some detail by way of illustration and example for purposes of clarity of understanding, it will be understood by those skilled in the art that certain changes and modifications can be practiced within the scope of the claims.

That which is claimed:

1. A method for benefiting plant growth and/or plant health, the method comprising:
   delivering to seed of a plant, roots of a plant, or soil surrounding a plant a composition comprising:
   a biologically pure culture of a *Bacillus velezensis* RTI301 deposited as ATCC No. PTA-121165, or a mutant thereof having all the identifying characteristics thereof; and
   a biologically pure culture of a *Bacillus subtilis* RTI477 deposited as ATCC No. PTA-121167, or a mutant thereof having all the identifying characteristics thereof, wherein delivery of the composition benefits plant growth and/or plant health.

2. The method of claim 1, wherein the benefits to plant growth and/or plant health comprise increased yield, improved seedling vigor, improved root development, improved plant growth, improved plant health, improved appearance, improved resistance to plant pathogens, reduced pathogenic infection, or a combination thereof.

3. The method of claim 2, wherein the plant pathogen comprises one or a combination of insects, nematodes, plant pathogenic fungi, or plant pathogenic bacteria, or
   wherein the plant pathogen comprises one or more of a plant fungal pathogen, a plant bacterial pathogen, a rust fungus, a *Botrytis* spp., a *Botrytis cinerea*, a *Botrytis squamosa*, an *Erwinia* spp., an *Erwinia carotovora*, an *Erwinia amylovora*, a *Dickeya* spp., a *Dickeya dadantii*, a *Dickeya solani*, an *Agrobacterium* spp., a *Agrobacterium tumefaciens*, a *Xanthomonas* spp., a *Xanthomonas axonopodis*, a *Xanthomonas campestris* pv. *carotae*, a *Xanthomonas pruni*, a *Xanthomonas arboricola*, a *Xanthomonas oryzae* pv. *oryzae*, a *Xylella* spp., a *Xylella fastidiosa*, a *Candidatus* spp., a *Candidatus liberibacter*, a *Fusarium* spp., a *Fusarium colmorum*, a *Fusarium graminearum*, a *Fusarium oxysporum*, a *Fusarium oxysporum* f sp. *Cubense*, a *Fusarium oxysporum* f sp. *Lycopersici*, a *Fusarium virguliforme*, a *Sclerotinia* spp., a *Sclerotinia sclerotiorum*, a *Sclerotinia minor*, *Sclerotinia homeocarpa*, a *Cercospora/Cercosporidium* spp., an *Uncinula* spp., an *Uncinula necator* (Powdery Mildew), a *Podosphaera* spp. (Powdery Mildew), a *Podosphaera leucotricha*, a *Podosphaera clandestine*, a *Phomopsis* spp., a *Phomopsis viticola*, an *Alternaria* spp., an *Alternaria tenuissima*, an *Alternaria porri*, an *Alternaria alternate*, an *Alternaria solani*, an *Alternaria tenuis*, a ispp., a *Pseudomonas syringae* pv. Tomato, a *Phytophthora* spp., a *Phytophthora infestans*, a *Phytophthora parasitica*, a *Phytophthora sojae*, a *Phytophthora capsici*, a *Phytophthora cinnamon*, a *Phytophthora fragariae*, a *Phytophthora* spp., a *Phytophthora ramorum*, a *Phytophthora palmivara*, a *Phytophthora nicotianae*, a *Phakopsora* spp., a *Phakopsora pachyrhizi*, a *Phakopsora meibomiae*, an *Aspergillus* spp., an *Aspergillus flavus*, an *Aspergillus niger*, a *Uromyces* spp., a *Uromyces appendiculatus*, a *Cladosporium* spp., a *Cladosporium herbarum*, a *Rhizopus* spp., a *Rhizopus arrhizus*, a *Penicillium* spp., a *Rhizoctonia* spp., a *Rhizoctonia solani*, a *Rhizoctonia zeae*, a *Rhizoctonia oryzae*, a *Rhizoctonia caritae*, a *Rhizoctonia cerealis*, a *Rhizoctonia crocorum*, a *Rhizoctonia fragariae*, a *Rhizoctonia ramicola*, a *Rhizoctonia rubi*, a *Rhizoctonia leguminicola*, a *Macrophomina phaseolina*, a *Magnaorthe oryzae*, a *Mycosphaerella* spp., *Mycosphaerella* graminocola, a *Mycosphaerella fijiensis* (Black sigatoga), a *Mycosphaerella pomi*, a *Mycosphaerella citri*, a *Magnaporthe* spp., a *Magnaporthe grisea*, a *Monilinia* spp., a *Monilinia fruticola*, a *Monilinia vacciniicorymbosi*, a *Monilinia laxa*, a *Colletotrichum* spp., a *Colletotrichum gloeosporiodes*, a *Colletotrichum acutatum*, a *Colletotrichum Candidum*, a *Dia-*

*porthe* spp., a *Diaporthe citri*, a *Corynespora* spp., a *Corynespora Cassiicola*, a *Gymnosporangium* spp., a *Gymnosporangium juniperi-virginianae*, a *Schizothyrium* spp., a *Schizothyrium pomi*, a *Gloeodes* spp., a *Gloeodes pomigena*, a *Botryosphaeria* spp., a *Botryosphaeria dothidea*, a *Neofabraea* spp., a *Wilsonomyces* spp., a *Wilsonomyces carpophilus*, a *Sphaerotheca* spp., a *Sphaerotheca macularis*, a *Sphaerotheca pannosa*, a *Erysiphe* spp., a *Stagonospora* spp., a *Stagonospora nodorum*, a *Pythium* spp., a *Pythium ultimum*, a *Pythium aphanidermatum*, a *Pythium irregularum*, a *Pythium ulosum*, a *Pythium lutriarium*, a *Pythium sylvatium*, a *Venturia* spp, a *Venturia inaequalis*, a *Verticillium* spp., a *Ustilago* spp., a *Ustilago nuda*, a *Ustilago maydis*, a *Ustilago scitaminea*, a *Claviceps* spp., a *Claviceps puprrea*, a *Tilletia* spp., a *Tilletia tritici*, a *Tilletia laevis*, a *Tilletia horrid*, a *Tilletia controversa*, a *Phoma* spp., a *Phoma glycinicola*, a *Phoma exigua*, a *Phoma lingam*, a *Cocliobolus sativus*, a *Gaeumanomyces gaminis*, a *Colleototricum* spp., a *Rhychosporium* spp., *Rhychosporium secalis*, a *Biopolaris* spp., a *Helminthosporium* spp., a *Helminthosporium secalis*, a *Helminthosporium maydis*, a *Helminthosporium solai*, or a *Helminthosporium tritici-repentis*.

4. The method of claim 1, wherein the composition is in the form of a liquid, an oil dispersion, a dust, a dry wettable powder, a spreadable granule, or a dry wettable granule, or
wherein the composition is in the form of a liquid and each of the *Bacillus subtilis* RTI477 and the *Bacillus velezensis* RTI301 are present at a concentration of from about $1.0 \times 10^8$ CFU/ml to about $1.0 \times 10^{12}$ CFU/ml, or
wherein the composition is in the form of a dust, a dry wettable powder, a spreadable granule, or a dry wettable granule and each of the *Bacillus subtilis* RTI477 and the *Bacillus velezensis* RTI301 are present in an amount of from about $1.0 \times 10^8$ CFU/g to about $1.0 \times 10^{12}$ CFU/g, or
wherein the composition is in the form of an oil dispersion and each of the *Bacillus subtilis* RTI477 and the *Bacillus velezensis* RTI301 are present at a concentration of from about $1.0 \times 10^8$ CFU/ml to about $1.0 \times 10^{12}$ CFU/ml, or
wherein the *Bacillus subtilis* RTI477 and the *Bacillus velezensis* RTI301 are present in the form of spores or vegetative cells.

5. The method of claim 1, wherein the composition further comprises one or a combination of a carrier, a dispersant or a yeast extract.

6. The method of claim 1, wherein the plant comprises monocots, dicots, Cereals, Corn, Sweet Corn, Popcorn, Seed Corn, Silage Corn, Field Corn, Rice, Wheat, Barley, Sorghum, Asparagus, Berry, Blueberry, Blackberry, Raspberry, Loganberry, Huckleberry, Cranberry, Gooseberry, Elderberry, Currant, Caneberry, Bushberry, Brassica Vegetables, Broccoli, Cabbage, Cauliflower, Brussels Sprouts, Collards, Kale, Mustard Greens, Kohlrabi, Cucurbit Vegetables, Cucumber, Cantaloupe, Melon, Muskmelon, Squash, Watermelon, Pumpkin, Eggplant, Bulb Vegetables, Onion, Garlic, Shallots, Citrus, Orange, Grapefruit, Lemon, Tangerine, Tangelo, Pummelo, Fruiting Vegetables, Pepper, Tomato, Ground Cherry, Tomatillo, Okra, Grape, Herbs/Spices, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Coconut, Cotton, Flax, Oil Palm, Olive, Peanut, Rapeseed, Safflower, Sesame, Sunflower, Soybean, Pome Fruit, Apple, Crabapple, Pear, Quince, Mayhaw, Root/Tuber and Corn Vegetables, Carrot, Potato, Sweet Potato, Cassave, Beets, Ginger, Horseradish, Radish, Ginseng, Turnip, Stone Fruit, Apricot, Cherry, Nectarine, Peach, Plum, Prune, Strawberry, Tree Nuts, Almond, Pistachio, Peca n, Walnut, Filberts, Chestnut, Cashew, Beechnut, Butternut, Macadamia, Kiwi, Banana, (Blue) Agave, Grass, Turf grass, Ornamental plants, Poinsettia, Hardwood cuttings, Chestnuts, Oak, Maple, sugarcane, or sugarbeet.

7. The method of claim 1, wherein the plant comprises soybean or corn and the plant growth benefit is exhibited by increased yield.

8. The method of claim 1, wherein the composition further comprises one or a combination of a microbial, a biological, or a chemical insecticide, fungicide, nematicide, bacteriocide, herbicide, plant extract, plant growth regulator, or fertilizer present in an amount suitable to benefit plant growth and/or to confer protection against a pathogenic infection in the plant.

9. The method of claim 8, wherein the insecticide comprises bifenthrin.

10. The method of claim 9, wherein the composition is in a formulation compatible with a liquid fertilizer, or
wherein the composition further comprises a hydrated aluminum-magnesium silicate and at least one dispersant, or
wherein the bifenthrin insecticide is present at a concentration ranging from 0.1 g/ml to 0.2 g/ml, or
wherein the bifenthrin insecticide is present at a concentration of about 0.1715 g/ml.

11. A method for benefiting plant growth and/or plant health, the method comprising:
delivering to seed of a plant, roots of a plant, or soil surrounding a plant a combination of:
a first composition comprising a biologically pure culture of a *Bacillus velezensis* RTI301 deposited as ATCC No. PTA-121165, or a mutant thereof having all the identifying characteristics thereof; and
a second composition comprising a biologically pure culture of a *Bacillus subtilis* RTI477 deposited as ATCC No. PTA-121167, or a mutant thereof having all the identifying characteristics thereof,
wherein delivery of the combination benefits the plant growth and/or plant health.

12. The method of claim 11, wherein the benefits to plant growth and/or plant health comprise increased yield, improved seedling vigor, improved root development, improved plant growth, improved plant health, improved appearance, improved resistance to plant pathogens, reduced pathogenic infection, or a combination thereof.

13. The method of claim 12, wherein the plant pathogen comprises one or a combination of insects, nematodes, plant pathogenic fungi, or plant pathogenic bacteria, or
wherein the plant pathogen comprises one or more of a plant fungal pathogen, a plant bacterial pathogen, a rust fungus, a *Botrytis* spp., a *Botrytis cinerea*, a *Botrytis squamosa*, an *Erwinia* spp., an *Erwinia carotovora*, an *Erwinia amylovora*, a *Dickeya* spp., a *Dickeya dadantii*, a *Dickeya solani*, an *Agrobacterium* spp., a *Agrobacterium tumefaciens*, a *Xanthomonas* spp., a *Xanthomonas axonopodis*, a *Xanthomonas campestris* pv. *carotae*, a *Xanthomonas pruni*, a *Xanthomonas arboricola*, a *Xanthomonas oryzae* pv. *oryzae*, a *Xylella* spp., a *Xylella fastidiosa*, a *Candidatus* spp., a *Candidatus liberibacter*, a *Fusarium* spp., a *Fusarium col-* morum, a *Fusarium graminearum*, a *Fusarium oxysporum*, a *Fusarium oxysporum* f sp. *Cubense*, a *Fusarium oxysporum* f sp. *Lycopersici*, a *Fusarium virguliforme*, a *Sclerotinia* spp., a *Sclerotinia sclerotiorum*, a *Sclerotinia minor*, *Sclerotinia homeocarpa*, a *Cercospora/Cercosporidium* spp., an *Uncinula* spp., an *Uncinula necator* (Powdery Mildew), a *Podosphaera* spp. (Powdery Mildew), a *Podosphaera leucotricha*, a *Podosphaera clandestine*, a *Phomopsis* spp., a *Phomopsis viticola*, an *Alternaria* spp., an *Alternaria tenuissima*, an *Alternaria porfi*, an *Alternaria alternate*, an *Alternaria solani*, an *Alternaria tenuis*, a *Pseudomonas* spp., a *Pseudomonas syringae* pv. Tomato, a *Phytophthora* spp., a *Phytophthora infestans*, a *Phytophthora parasitica*, a *Phytophthora sojae*, a *Phytophthora capsici*, a *Phytophthora cinnamon*, a *Phytophthora fragariae*, a *Phytophthora* spp., a *Phytophthora ramorum*, a *Phytophthora palmivara*, a *Phytophthora nicotianae*, a *Phakopsora* spp., a *Phakopsora pachyrhizi*, a *Phakopsora meibomiae*, an *Aspergillus* spp., an *Aspergillus flavus*, an *Aspergillus niger*, a *Uromyces* spp., a *Uromyces appendiculatus*, a *Cladosporium* spp., a *Cladosporium herbarum*, a *Rhizopus* spp., a *Rhizopus arrhizus*, a *Penicillium* spp., a *Rhizoctonia* spp., a *Rhizoctonia solani*, a *Rhizoctonia zeae*, a *Rhizoctonia oryzae*, a *Rhizoctonia caritae*, a *Rhizoctonia cerealis*, a *Rhizoctonia crocorum*, a *Rhizoctonia fragariae*, a *Rhizoctonia ramicola*, a *Rhizoctonia rubi*, a *Rhizoctonia leguminicola*, a *Macrophomina phaseolina*, a *Magnaorthe oryzae*, a *Mycosphaerella* spp., *Mycosphaerella graminocola*, a *Mycosphaerella fyiensis* (Black sigatoga), a *Mycosphaerella pomi*, a *Mycosphaerella citri*, a *Magnaporthe* spp., a *Magnaporthe grisea*, a *Monilinia* spp., a *Monilinia fruticola*, a *Monilinia vacciniicorymbosi*, a *Monilinia laxa*, a *Colletotrichum* spp., a *Colletotrichum gloeosporiodes*, a *Colletotrichum acutatum*, a *Colletotrichum Candidum*, a *Diaporthe* spp., a *Diaporthe citri*, a *Corynespora* spp., a *Corynespora Cassiicola*, a *Gymnosporangium* spp., a *Gymnosporangium juniperi-virginianae*, a *Schizothyrium* spp., a *Schizothyrium pomi*, a *Gloeodes* spp., a *Gloeodes pomigena*, a *Botryosphaeria* spp., a *Botryosphaeria dothidea*, a *Neofabraea* spp., a *Wilsonomyces* spp., a *Wilsonomyces carpophilus*, a *Sphaerotheca* spp., a *Sphaerotheca macularis*, a *Sphaerotheca pannosa*, a *Erysiphe* spp., a *Stagonospora* spp., a *Stagonospora nodorum*, a *Pythium* spp., a *Pythium ultimum*, a *Pythium aphanidermatum*, a *Pythium irregularum*, a *Pythium ulosum*, a *Pythium lutriarium*, a *Pythium sylvatium*, a *Venturia* spp, a *Venturia inaequalis*, a *Verticillium* spp., a *Ustilago* spp., a *Ustilago nuda*, a *Ustilago maydis*, a *Ustilago scitaminea*, a *Claviceps* spp., a *Claviceps puprrea*, a *Tilletia* spp., a *Tilletia tritici*, a *Tilletia laevis*, a *Tilletia horrid*, a *Tilletia controversa*, a *Phoma* spp., a *Phoma glycinicola*, a *Phoma exigua*, a *Phoma lingam*, a *Cocliobolus sativus*, a *Gaeumanomyces gaminis*, a *Colleototricum* spp., a *Rhychosporium* spp., *Rhychosporium secalis*, a *Biopolaris* spp., a *Helminthosporium* spp., a *Helminthosporium secalis*, a *Helminthosporium maydis*, a *Helminthosporium solai*, or a *Helminthosporium tritici-repentis*.

14. The method of claim 11, wherein the first and second compositions are in the form of a liquid, an oil dispersion, a dust, a dry wettable powder, a spreadable granule, or a dry wettable granule, or wherein the first and second compositions are in the form of a liquid and each of the *Bacillus subtilis* RTI477 and the *Bacillus velezensis* RTI301 are present at a concentration of from about $1.0 \times 10^8$ CFU/ml to about $1.0 \times 10^{12}$ CFU/ml, or wherein the first and second compositions are in the form of a dust, a dry wettable powder, a spreadable granule, or a dry wettable granule and each of the *Bacillus subtilis* RTI477 and the *Bacillus* velezensis RTI301 are present in an amount of from about $1.0 \times 10^8$ CFU/g to about $1.0 \times 10^{12}$ CFU/g, or wherein the first and second compositions are in the form of an oil dispersion and each of the *Bacillus subtilis* RTI477 and the *Bacillus* velezensis RTI301 are present at a concentration of from about $1.0 \times 10^8$ CFU/ml to about $1.0 \times 10^{12}$ CFU/ml, or wherein the *Bacillus subtilis* RTI477 and the *Bacillus* velezensis RTI301 are present in the form of spores or vegetative cells.

15. The method of claim 11, wherein the first and second compositions further comprise one or a combination of a carrier, a dispersant or a yeast extract.

16. The method of claim 11, wherein the plant comprises monocots, dicots, Cereals, Corn, Sweet Corn, Popcorn, Seed Corn, Silage Corn, Field Corn, Rice, Wheat, Barley, Sorghum, Asparagus, Berry, Blueberry, Blackberry, Raspberry, Loganberry, Huckleberry, Cranberry, Gooseberry, Elderberry, Currant, Caneberry, Bushberry, Brassica Vegetables, Broccoli, Cabbage, Cauliflower, Brussels Sprouts, Collards, Kale, Mustard Greens, Kohlrabi, Cucurbit Vegetables, Cucumber, Cantaloupe, Melon, Muskmelon, Squash, Watermelon, Pumpkin, Eggplant, Bulb Vegetables, Onion, Garlic, Shallots, Citrus, Orange, Grapefruit, Lemon, Tangerine, Tangelo, Pummelo, Fruiting Vegetables, Pepper, Tomato, Ground Cherry, Tomatillo, Okra, Grape, Herbs/Spices, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Coconut, Cotton, Flax, Oil Palm, Olive, Peanut, Rapeseed, Safflower, Sesame, Sunflower, Soybean, Pome Fruit, Apple, Crabapple, Pear, Quince, Mayhaw, Root/Tuber and Corn Vegetables, Carrot, Potato, Sweet Potato, Cassave, Beets, Ginger, Horseradish, Radish, Ginseng, Turnip, Stone Fruit, Apricot, Cherry, Nectarine, Peach, Plum, Prune, Strawberry, Tree Nuts, Almond, Pistachio, Peca n, Walnut, Filberts, Chestnut, Cashew, Beechnut, Butternut, Macadamia, Kiwi, Banana, (Blue) Agave, Grass, Turf grass, Ornamental plants, Poinsettia, Hardwood cuttings, Chestnuts, Oak, Maple, sugarcane, or sugarbeet.

17. The method of claim 11, wherein the plant comprises soybean or corn and the plant growth benefit is exhibited by increased yield.

18. The method of claim 11, wherein one or both of the first and second compositions further comprises one or a combination of a microbial, a biological, or a chemical insecticide, fungicide, nematicide, bacteriocide, herbicide, plant extract, plant growth regulator, or fertilizer present in an a mount suitable to benefit plant growth and/or to confer protection against a pathogenic infection in the plant.

19. The method of claim 18, wherein the insecticide comprises bifenthrin.

20. The method of claim 19, wherein the composition is in a formulation compatible with a liquid fertilizer, or wherein the composition further comprises a hydrated aluminum-magnesium silicate and at least one dispersant, or wherein the bifenthrin insecticide is present at a concentration ranging from 0.1 g/ml to 0.2 g/ml, or wherein the bifenthrin insecticide is present at a concentration of about 0.1715 g/ml.

21. A method for benefiting plant growth and/or plant health, the method comprising:
    planting a seed of a plant in a suitable growth medium, wherein the seed has been coated with a composition comprising:
    spores of a biologically pure culture of *Bacillus* velezensis RTI301 deposited as ATCC No. PTA-121165, or a mutant thereof having all the identifying characteristics thereof; and
    spores of a biologically pure culture of *Bacillus subtilis* RTI477 deposited as ATCC No. PTA-121167, or a mutant thereof having all the identifying characteristics thereof,
    wherein the *Bacillus* velezensis RTI301 and the *Bacillus subtilis* RTI477 are present in an amount suitable to benefit the plant growth and/or plant health.

22. The method of claim 21, wherein the benefit to plant growth and/or plant health comprises increased yield, improved seedling vigor, improved root development, improved plant growth, improved plant health, improved appearance, improved resistance to plant pathogens, reduced pathogenic infection, or a combination thereof.

23. The method of claim 22, wherein the plant pathogen comprises one or a combination of insects, nematodes, plant pathogenic fungi, or plant pathogenic bacteria, or
    wherein the plant pathogen comprises one or more of a plant fungal pathogen, a plant bacterial pathogen, a rust fungus, a *Botrytis* spp., a *Botrytis cinerea*, a *Botrytis squamosa*, an *Erwinia* spp., an *Erwinia carotovora*, an *Erwinia amylovora*, a *Fusarium* spp., a *Fusarium colmorum*, a *Fusarium graminearum*, a *Fusarium oxysporum*, a *Fusarium oxysporum* f sp. *Cubense*, a *Fusarium oxysporum* f sp. *Lycopersici*, a *Fusarium virguliforme*, a *Xanthomonas* spp., a *Xanthomonas axonopodis*, a *Xanthomonas campestris* pv. *carotae*, a *Xanthomonas pruni*, a *Xanthomonas arboricola*, a *Xanthomonas oryzae* pv. *oryzae*, a *Pseudomonas* spp., a *Pseudomonas syringae* pv. Tomato, a *Phytophthora* spp., a *Phytophthora infestans*, a *Phytophthora parasitica*, a *Phytophthora sojae*, a *Phytophthora capsici*, a *Phytophthora cinnamon*, a *Phytophthora fragariae*, a *Phytophthora* spp., a *Phytophthora ramorum*, a *Phytophthora palmivara*, a *Phytophthora nicotianae*, a *Rhizoctonia* spp., a *Rhizoctonia solani*, a *Rhizoctonia zeae*, a *Rhizoctonia oryzae*, a *Rhizoctonia caritae*, a *Rhizoctonia cerealis*, a *Rhizoctonia crocorum*, a *Rhizoctonia fragariae*, a *Rhizoctonia ramicola*, a *Rhizoctonia rubi*, a *Rhizoctonia leguminicola*, a *Macrophomina phaseolina*, a *Magnaorthe oryzae*, a *Pythium* spp., a *Pythium ultimum*, a *Pythium aphanidermatum*, a *Pythium irregularum*, a *Pythium ulosum*, a *Pythium lutriarium*, a *Pythium sylvatium*, a *Ustilago* spp., a *Ustilago nuda*, a *Ustilago maydis*, a *Ustilago scitaminea*, a *Claviceps* spp., a *Claviceps puprrea*, a *Tilletia* spp., a *Tilletia tritici*, a *Tilletia laevis*, a *Tilletia horrid*, a *Tilletia controversa*, a *Phoma* spp., a *Phoma glycinicola*, a *Phoma exigua*, a *Phoma lingam*, a *Cocliobolus sativus*, a *Gaeumanomyces gaminis*, or a *Colleototricum* spp.

24. The method of claim 21, wherein the composition further comprises one or a combination of a microbial, a biological, or a chemical insecticide, fungicide, nematicide, bacteriocide, herbicide, plant extract, plant growth regulator, or fertilizer present in an amount suitable to benefit plant growth and/or to confer protection against a pathogenic infection in the susceptible plant.

25. The method of claim 24, wherein the insecticide comprises bifenthrin.

26. The method of claim 21, wherein each of the *Bacillus subtilis* RTI477 and the *Bacillus velezensis* RTI301 are present in an amount ranging from about $1.0 \times 10^2$ CFU/seed to about $1.0 \times 10$ CFU/seed.

27. The method of claim 21, wherein the seed of the plant comprises the seed of monocots, dicots, Cereals, Corn, Sweet Corn, Popcorn, Seed Corn, Silage Corn, Field Corn, Rice, Wheat, Barley, Sorghum, Brassica Vegetables, Broccoli, Cabbage, Cauliflower, Brussels Sprouts, Collards, Kale, Mustard Greens, Kohlrabi, Bulb Vegetables, Onion, Garlic, Shallots, Fruiting Vegetables, Pepper, Tomato, Ground Cherry, Tomatillo, Okra, Grape, Herbs/Spices, Cucurbit Vegetables, Cucumber, Cantaloupe, Melon, Muskmelon, Squash, Watermelon, Pumpkin, Eggplant, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Cotton, Flax, Peanut, Rapeseed, Safflower, Sesame, Sunflower, Soybean, Root/Tuber and Corn Vegetables, Carrot, Potato, Sweet Potato, Beets, Ginger, Horseradish, Radish, Ginseng, Turnip, sugarcane, sugarbeet, Grass, or Turf grass.

28. The method of claim 21, wherein the seed of the plant comprises soybean or corn and the plant growth benefit is exhibited by increased yield.

* * * * *